US009523130B2

(12) United States Patent
Rikova et al.

(10) Patent No.: US 9,523,130 B2
(45) Date of Patent: *Dec. 20, 2016

(54) METHODS OF TREATING NON-SMALL CELL LUNG CARCINOMA (NSCLC)

(71) Applicant: Cell Signaling Technology, Inc., Danvers, MA (US)

(72) Inventors: Klarisa Rikova, Reading, MA (US); Herbert Haack, South Hamilton, MA (US); Laura Sullivan, Shrewsbury, MA (US); Ailan Guo, Lexington, MA (US); Anthony Possemato, Worcester, MA (US); Joan MacNeill, Litchfield, NH (US); Ting-Lei Gu, Woburn, MA (US); Jian Yu, Hamilton, MA (US)

(73) Assignee: CELL SIGNALING TECHNOLOGY, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,998

(22) Filed: Aug. 2, 2016

(65) Prior Publication Data

US 2016/0333425 A1 Nov. 17, 2016

Related U.S. Application Data

(60) Continuation of application No. 14/870,154, filed on Sep. 30, 2015, which is a division of application No. 13/618,400, filed on Sep. 14, 2012, now abandoned, which is a continuation of application No. 12/891,987, filed on Sep. 28, 2010, now Pat. No. 8,377,642, which is a continuation of application No. 12/714,457, filed on Feb. 27, 2010, now Pat. No. 8,288,102, which is a continuation of application No. 11/787,132, filed on Apr. 13, 2007, now Pat. No. 7,700,339.

(60) Provisional application No. 60/792,364, filed on Apr. 14, 2006.

(51) Int. Cl.
| | |
|---|---|
| C12Q 1/48 | (2006.01) |
| A61K 31/00 | (2006.01) |
| C12Q 1/68 | (2006.01) |
| G01N 33/574 | (2006.01) |
| C12N 9/12 | (2006.01) |

(52) U.S. Cl.
CPC ..... *C12Q 1/6886* (2013.01); *C12Y 207/10001* (2013.01); *G01N 33/57423* (2013.01); *C12Q 2600/112* (2013.01); *C12Q 2600/158* (2013.01); *G01N 2333/912* (2013.01)

(58) Field of Classification Search
CPC ... A61K 38/00; C07K 2319/00; C12N 9/1205; C12Q 1/6886; C12Q 2600/136; C12Q 2600/156; G01N 2333/9121; G01N 33/574; G01N 33/57484; Y10T 436/117497

See application file for complete search history.

(56) References Cited

U.S. PATENT DOCUMENTS

| | | | |
|---|---|---|---|
| 5,529,925 | A | 6/1996 | Morris et al. |
| 7,230,098 | B2 | 6/2007 | Cui et al. |
| 7,605,131 | B2 | 10/2009 | Mano et al. |
| 7,700,339 | B2 | 4/2010 | Rikova et al. |
| 7,728,120 | B2 | 6/2010 | Mano et al. |
| 7,825,137 | B2 | 11/2010 | Christensen et al. |
| 7,858,643 | B2 | 12/2010 | Cui et al. |
| 8,168,383 | B2 | 5/2012 | Rikova et al. |
| 8,232,060 | B2 | 7/2012 | Rikova et al. |
| 8,288,102 | B2 | 10/2012 | Rikova et al. |
| 8,377,642 | B2 | 2/2013 | Rikova et al. |
| 8,481,279 | B2 | 7/2013 | Rikova et al. |
| 8,486,645 | B2 | 7/2013 | Rikova et al. |
| 2003/0099974 | A1 | 5/2003 | Lillie et al. |
| 2005/0009840 | A1 | 1/2005 | Cui et al. |
| 2006/0046991 | A1 | 3/2006 | Cui et al. |
| 2008/0090776 | A1 | 4/2008 | Mano et al. |

(Continued)

FOREIGN PATENT DOCUMENTS

| | | |
|---|---|---|
| EP | 1 914 240 A1 | 4/2008 |
| EP | 2 116 553 A1 | 11/2009 |

(Continued)

OTHER PUBLICATIONS

Barreca A. et al., "Anaplastic Lymphoma Kinase in Human Cancer", Journal of Molecular Endocrinology 47:R11-R23 (2011).

(Continued)

*Primary Examiner* — Delia Ramirez
(74) *Attorney, Agent, or Firm* — Scully, Scott, Murphy & Presser, P.C.

(57) ABSTRACT

Novel gene deletions and translocations involving chromosome 2 resulting in fusion proteins combining part of Anaplastic Lymphoma Kinase (ALK) kinase with part of a secondary protein have been identified herein in human solid tumors, e.g. non-small cell lung carcinoma (NSCLC). Secondary proteins include Echinoderm Microtubule-Associated Protein-Like 4 (EML-4) and TRK-Fusion Gene (TFG). The EML4-ALK fusion protein, which retains ALK tyrosine kinase activity, was confirmed to drive the proliferation and survival of NSCLC characterized by this mutation. The invention therefore provides, in part, isolated polynucleotides and vectors encoding the disclosed mutant ALK kinase polypeptides, probes for detecting it, isolated mutant polypeptides, recombinant polypeptides, and reagents for detecting the fusion and truncated polypeptides. The disclosed identification of this new fusion protein enables methods for screening for compounds that inhibit the proteins, and methods for inhibiting the progression of a cancer characterized by the mutant polynucleotides or polypeptides.

29 Claims, 17 Drawing Sheets

(56) References Cited

U.S. PATENT DOCUMENTS

| | | |
|---|---|---|
| 2008/0300273 A1 | 12/2008 | Christensen et al. |
| 2009/0099193 A1 | 4/2009 | Mano et al. |
| 2013/0209452 A1 | 8/2013 | Rikova et al. |
| 2016/0186268 A1 | 6/2016 | Rikova et al. |

FOREIGN PATENT DOCUMENTS

| | | |
|---|---|---|
| JP | 2008295444 A | 12/2008 |
| WO | 2005/026158 A1 | 3/2003 |
| WO | 2004/050681 A2 | 6/2004 |
| WO | 2004/079326 A2 | 9/2004 |
| WO | 2004/080980 A1 | 9/2004 |
| WO | 2005/009389 A2 | 2/2005 |
| WO | 2005/016894 A1 | 2/2005 |
| WO | 2005/026130 A1 | 3/2005 |
| WO | 2005/054237 A1 | 6/2005 |
| WO | 2005/056752 A2 | 6/2005 |
| WO | 2005/080393 A1 | 9/2005 |
| WO | 2005/083439 A1 | 9/2005 |
| WO | 2005/097765 A1 | 10/2005 |
| WO | 2006/021454 A2 | 3/2006 |
| WO | 2006/021457 A2 | 3/2006 |
| WO | 2009/102446 A2 | 8/2009 |
| WO | 2010/132888 A2 | 11/2010 |

OTHER PUBLICATIONS

Bischof D. et al., "Role of the Nucleophosmin (NPM) Portion of the Non-Hodgkin's Lymphoma-Associated NPM-Anaplastic Lymphoma Kinase Fusion Protein in Oncogenesis", Molecular and Cellular Biology 17(4):2312-2325 (Apr. 1997).

Boyle M.B., "Voltage-Dependent Sodium Channel Alpha Subunit", Medline [online], Medline Accession No. Q80WH9 http://www.ncbi.nlm.nih.gov/protein/q80wh9 (Oct. 31, 2006).

Bridge R.S. et al., "Molecular Diagnosis of Ewing Sarcoma/Primitive Neuroectodermal Tumor in Routinely Processes Tissue: a Comparison of Two FISH Strategies and RT-PCR in Malignant Round Cell Tumors", Modern Pathology 19:1-8 (2006).

Bridge J. et al., "Fusion of the ALK Gene to the Clathrin Heavy Chain Gene, CLTC, in Inflammatory Myofibroblastic Tumor", American Journal of Pathology 159(2):411-415 (Aug. 2001).

Buno I. et al., "Lymphoma Associated Chromosomal Abnormalities can Easily be Detected by FISH on Tissue Imprints. An Underused Diagnostic Alternative", Journal of Clinical Pathology 58:629-633 (2005).

Butrynski J.E. et al., "Crizotinib in ALK-Rearranged Inflammatory Myofibroblastic Tumor", The New England Journal of Medicine 363(18):1727-1733 (Oct. 28, 2010).

Choi Y. et al., "Identification of Novel Isoforms of the EML4-ALK Transforming Gene in Non-Small Cell Lung Cancer", Cancer Research 68(13):4971-4976 (Jul. 1, 2008).

Dang T.P. et al.,"Cromosome 19 Translocation, Over expression of Notch3, and Human Lung Cancer", Journal of the National Cancer Institute 92(16):1355-1357 (Aug. 16, 2000).

Dirks W.G. et al., "Expression and Functional Analysis of the Anaplastic Lymphoma Kinase (Alk) Gene in Tumor Cell Lines", Int. J. Cancer 100:49-56 (2002).

Drabkin H.A. et al., "DEF-3(916/NT-LU-12), an RNA Binding Protein From the 3p21.3 Homozygous Deletion Region in SCLC", Oncogene 18(16):2589-2597 (1999).

Falini B. et al., "Proteins Encoded by Genes Involved in Chromosomal Alterations in Lymphoma and Leukemia: Clinical Value of Their Detection by Immunocytochemistry", Blood 99(2):409-426 (Jan. 2002).

Falini B. et al., "ALK Expression Defines a Distinct Group of T/Null Lymphomas ("ALK Lymphomas") with a wide Morphological Spectrum", American Journal of Pathology 153(3):875-886 (Sep. 1998).

Galkin A.V. et al., "Identification of NVP-TAE684, a Potent, Selective, and Efficacious Inhibitor of NPM-ALK", PNAS 104(1):270-275 (Jan. 2, 2007).

Garklik R. et al., "Vectors and Delivery Systems in Gene Therapy", Med Sci Monit 11(4):RA110-121 (2005).

Gerber S.A. et al., "Absolute Quantification of Proteins and Phosphoproteins from Cell Lysates by Tandem MS", PNAS 100(12):6940-6945 (Jun. 10, 2003).

Hernandez L. et al., "Diversity of Genomic Breakpoints in TFG-ALK Translocations in Anaplastic Large Cell Lymphomas: Identification of a New TFG-ALKxL Chimeric Gene with Transforming Activity", American Journal of Pathology 160(4):1487-1494 (Apr. 2002).

Hernandez L. et al., "TRK-Fused Gene (TFG) is a New Partner of ALK in Anaplastic Large Cell Lymphoma Producing Two Structurally Different TFG-ALK Translocations", Blood 94(9):3265-3268 (Nov. 1, 1999).

Horn L. et al., "EML4-ALK: Honing in on a New Target in Non-Small-Cell Lung Cancer", Journal of Clinical Oncology 27(26):4232-4235 (Sep. 10, 2009).

Iwahara T. et al., "Molecular Characterization of ALK, a Receptor Tyrosine Kinase Expressed Specifically in the Nervous System", Oncogene 14:439-449 (1997).

Just P-A. et al., "Histologic Subtypes, Immunohistochemistry, FISH or Molecular Screening for the Accurate Diagnosis of ALK-Rearrangement in Lung Cancer: A Comprehensive Study of Caucasian Non-Smokers", Lung Cancer 3963:1-7 (Dec. 6, 2011).

Kijima T. et al., "Favorable Response to Crizotinib in Three Patients With Echinoderm Microtubule-Associated Protein-Like 4-Anaplastic Lymphoma Kinase Fusion-Type Oncogene-Positive Non-Small Cell Lung Cancer", 102 (8):1602-1604 (Aug. 2011).

Koivunen J.P. et al., "EML4-ALK Fusion Gene and Efficacy of an ALK Kinase Inhibitor in Lung Cancer", Clin Cancer Res 14(13):4275-4283 (Jul. 1, 2008).

Kurzrock R. et al., "The Molecular Genetics of Philadelphia Chromosome-Positive Leukemias", The New England Journal of Medicine 319(15):990-998 (1988).

Kwak E.L. et al., "Anaplastic Lymphoma Kinase Inhibition in Non-Small-Cell Lung Cancer", The New England Journal of Medicine 363(18):1693-1703 (Oct. 28, 2010).

Lamant L. et al., "A New Fusion Gene TPM3-ALK in Anaplastic Large Cell Lymphoma Created by a (1;2) (q25;p. 23) Translocation", Blood 93(9):3088-3095 (May 1, 2009).

Lawrence B. et al., "TPM3-ALK and TPM4-ALK Oncogenes in Inflammatory Myofibroblastic Tumors", American Journal of Pathology 157(2):377-384 (Aug. 2000).

Li R. et al., "Design and Synthesis of 5-Aryl-Pyridone-Carboxamides as Inhibitors of Anaplastic Lymphoma Kinase", Journal of Medicinal Chemistry 49(3):1006-1015 (2006).

Marzec M. et al., Inhibition of ALK Enzymatic Activity in T-Cell Lymphoma Cells Induces Apoptosis and Suppresses Proliferation and STAT3 Phosphorylation Independently of Jak3:, Laboratory Investigation 85:1544-1554 (2005).

McDermott U. et al., "Genomic Alterations of Anaplastic Lymphoma Kinase May Sensitize Tumors to Anaplastic Lymphoma Kinase Inhibitors", Cancer Research 68(9):3389-3395 (May 1, 2008).

Morris S. et al., "ALK, the Chromosome 2 Gene Locus Altered by the t(2;5) in Non-Hodgkin's Lymphoma, Encodes a Novel Neural Receptor Tyrosine Kinase That is Highly Related to Leukocyte Tyrosine Kinase (LTK)", Oncogene 14 18):2175-2188 (1997).

Morris S.W. et al., Fusion of a Kinase Gene, ALK, to a Nucleolar Protein Gene, NPM, in Non-Hodgkin's Lymphoma:, Science 263:1281-1284 (Mar. 4, 1994).

Osajima-Hakomori Y. et al., "Biological Role of Anaplastic Lymphoma Kinase in Neuroblastoma", American Journal of Pathology 167(1):213-222 (Jul. 2005).

Oyama et al., Molecular Genetic Tumor Markers in Non-small Cell Lung Cancer:, Anticancer Research 25:1193-1196 (2005).

Patel R.M. et al., "Dual-color, Break-Apart Fluorescence in situ Hybridization for EWS Gene Rearrangement Distinguishes Clear Cell Sarcoma of Soft Tissue From Malignant Melanoma", Modern Pathology 18:1585-1590 (2005).

(56) References Cited

OTHER PUBLICATIONS

Phillips A.J., "The Challenge of Gene Therapy and DNA Delivery" Journal of Pharm. Pharmacology 53:1169-1174 (2001).
Pulford K. et al., "Anaplastic Lymphoma Kinase Proteins in Growth Control and Cancer", Journal of Cellular Physiology 199(3):330-358 (2004).
Pulford K. et al., "Detection of Anaplastic Lymphoma Kinase (ALK) and Nucleolar Protein Nucleophosmin (NPM)-ALK Proteins in Normal and Neoplastic Cells With the Monoclonal Antibody ALK1", Blood 89(4):1394-1404 (Feb. 15, 1997).
Sasaki T. et al., "The Biology and Treatment of EML4-ALK Non-Small Cell Lung Cancer", European Journal of Cancer 46:1773-1780 (2010).
Shinmura K. et al., "EML4-ALK Fusion Transcripts, But No NPM-, TPM3-, CLTC-, ATIC-, or TFG-Alk Fusion Transcripts, in Non-Small Cell Lung Carcinomas", Lung Cancer 61:163-169 (2008).
Shiota M. et al., "Diagnosis of t(2;5) (p23;q35)-Associated Ki-1 Lymphoma With Immunohistochemistry", Blood 84 (11):3648-3652 (Dec. 1, 1994).
Soda M. et al., "A Mouse Model for EML4-ALK-Positive Lung Cancer", PNAS 105(50):19893-19897 (Dec. 16, 2008).
Soda M. et al., "Identification of the Transforming EML-4_ALK Fusion Gene in Non-small Lung Cancer", Nature 448:561-566 (2007).
Takeuchi K. et al., "KIF5B-ALK, a Novel Fusion Oncokinase Identified by an Immunohistochemistry-Based Diagnostic System for ALK-positive Lung Cancer", Clinical Cancer Research 15(9):3143-3149 (May 1, 2009).
Takeuchi K. et al., "RET, ROS1 and ALK Fusions in Lung Cancer", Nature Medicine 18(3):378-381 (Feb. 12, 2012).
Tartari C.J. et al., "Characterization of Some Molecular Mechanisms Governing Autoactivation of the Catalytic Domain of the Anaplastic Lymphoma Kinase", The Journal of Biology Chemistry 283(7):3743-3750 (Feb. 15, 2008).
Tort F. et al., "Molecular Characterization of a New ALK Translocation Involving Moesin (MSN-ALK) in Anaplastic Large Cell Lymphoma", Laboratory Investigation 81(3):419-426 (Mar. 2001).
Touriol C. et al., "Further Demonstration of the Diversity of Chromosomal Changes Involving 2p23 in ALK-Positive Lymphoma: 2 Cases Expressing ALK Kinase Fused to CLTCL (clathrin chain polypeptide-like)", Blood 95 10):3204-3207 (May 15, 2000).
Wan W. et al., "Anaplastic Lymphoma Kinase Activity is Essential for the Proliferation and Survival of Anaplastic Large-Cell Lymphoma Cells", Blood 107(4):1617-1623 (Feb. 15, 2006).
Wong D.W-S. et al., "The EML4-ALK Fusion Gene is Involoved in Various Histologic Types of Lung Cancers from Nonsmokers with Wild-Type EGFR and KRAS", Cancer 115:1723-1733 (Apr. 2009).
Yamaguchi U. et al., "A Practical Approach to the Clinical Diagnosis of Ewing's Sarcoma/Primitive Neuroectodermal Tumour and Other Small Round Cell Tumours Sharing EWS Rearrangement Using New Fluorescence in situ Hybridisation Probes for EWSR1 on Formalin Fixed, Paraffin Wax Embedded Tissue", Journal of Clinical Pathology 58:1051-1056 (2005).
"Vysis LSI (Locus Specific Identifier) DNA Probes", (5 pages) (2007).
"LSI ALK Dual Color, Break Apart Rearrangement Probe", Abbot Laboratories Online, Vysis Inc., Downers Grove, IL, Revision Date: ID No: 30-622809 (1 page) (Oct. 10, 2004).
"Vysis ALK Break Apart FISH Probe Kit", Abbot Laboratories, Ref: 06N38-020, (10 pages) (Aug. 2011).
"ProbeChek ALK Negative Control Slides", Abbot Laboratories Ref: 06N38-005 (1 page) (Jul. 2011).
"ProbeChek ALK Positive Control Slides", Abbot Laboratories Ref: 06N38-010 (1 page) (Jul. 2011).
Vysis Paraffin Pretreatment IV & Post-Hybridization Wash Buffer Kit:, Abbot Laboratories Ref: 01N31-005 (3 pages) (Aug. 2011).
Database Uniport "SubName: Full=Voltage-dependent Sodium Channel Alpha Subunit; Flags: Fragments", [online] (Jun. 1, 2003).
Database Geneseq "Rice Abiotic Stress Responsive Polypeptide SEQ ID No. 7811", [online] (Jun. 2, 2005).
UniProt Database, EBI Accession No. Q80WH9 (Jun. 1, 2003).
Senebank database, Accession No. U55187.1 (Jun. 27, 1996).
International Search Report dated Aug. 29, 2008 received from International Application No. PCT/US07/09273.
Japanese Notification of Reason for Refusal dated Nov. 15, 2011 received from Application No. 2009-525538, together with an English-language translation.
Canadian Office Action dated Mar. 24, 2011 received from Application No. 2,648,864.
Pfizer Labs, "XALKORI (crizotinib) Capsules, Oral" (Aug. 2011) Reference ID: 3007054 (17 pages).
Third Party Observation for European Patent Application No. 12150525.9, dated Sep. 29, 2015.
Third Party Observation for European Patent Application No. 12150524.2, dated Sep. 29, 2015.
European Office Action dated Apr. 1, 2014 received from Application No. 12 150 525.9.
Chinese Office Action dated Jun. 16, 2014 received from Application No. 2013103093450, together with an English-language translation.
Juco J. et al., "Immunophenotypic Analysis of Anaplastic Large Cell Lymphoma by Flow Cytometry", American Journal of Clinical Pathology 119:205-212 (2003).
Ochs K. et al., "Case Report-Inflammatory Myofibroblastic Tumour of the Lung in a Five-Year-Old Girl", Interactive Cardiovascular and Thoracic Surgery 10:805-807 (2010).

Figure 2A

MDGFAGSLDDSISAASTSDVQDRLSALESRVQQQEDEITVLKAALADVLRRLAISEDHVASVKK
SVSSKGQPSPRAVIPMSCITNGSGANRKPSHTSAVSIAGKETLSSAAKSGTEKKKEKPQGQRE
KKEESHSNDQSPQIRASPSPQPSSQPLQIHRQTPESKNATPTKSIKRPSPAEKSHNSWENSDD
SRNKLSKIPSTPKLIPKVTKTADKHKDVIINQAKMSTREKNSQVYRRKHQELQAMQMELQSPEY
KLSKLRTSTIMTDYNPNYCFAGKTSSISDLKEVPRK**NITLIRGLGHGAFGEVYEGQVSGMPN
DPSPLQVAVKTLPEVCSEQDELDFLMEALIISKFNHQNIVRCIGVSLQSLPRFILLELM
AGGDLKSFLRETRPRPSQPSSLAMLDLLHVARDIACGCQYLEENHFIHRDIAARNCLL
TCPGPGRVAKIGDFGMARDIYRASYYRKGGCAMLPVKWMPPEAFMEGIFTSKTDTW
SFGVLLWEIFSLGYMPYPSKSNQEVLEFVTSGGRMDPPKNCPGPVYRIMTQCWQHQ
PEDRPNFAIILERIEYCTQDPD**VINTALPIEYGPLVEEEEKVPVRPKDPEGVPPLLVSQQAKRE
EERSPAAPPPLPTTSSGKAAKKPTAAEVSVRVPRGPAVEGGHVNMAFSQSNPPSELHKVHGSR
NKPTSLWNPTYGSWFTEKPTKKNNPIAKKEPHDRGNLGLEGSCTVPPNVATGRLPGASLLLEPS
SLTANMKEVPLFRLRHFPCGNVNYGYQQQGLPLEAATAPGAGHIEDTILKSKNSMNQPGP atggacggtttcgccggcagtctcgatgatagtatttctgctgcaagtacttctgatgttcaagatcgcctgtcagctc
ttgagtcacgagttcagcaacaagaagatgaaatcactgtgctaaaggcggctttggctgatgttttgagg
cgtcttgcaatctctgaagatcatgtggcctcagtgaaaaaatcagtctcaagtaaaggccaaccaagccctcgag
cagttattcccatgtcctgtataaccaatggaagtggtgcaaacagaaaaccaagtcataccagtgctgtctca
attgcaggaaaagaaactctttcatctgctgctaaaagtggtacagaaaaaaagaaagaaaaaccacaaggacag
agagaaaaaaagaggaatctcattctaatgatcaaagtccacaaattcgagcatcaccttctccccagccctct
tcacaacctctccaaatacacagacaaactccagaaagcaagaatgctactccaccaaagcataaaacgaccat
caccagctgaaaagtcacataattcttgggaaaattcagatgatagccgtaataaattgtcgaaaataccttca
acacccaaattaataccaaaagttaccaaaactgcagacaagcataaagatgtcatcatcaaccaag
caaaaatgtcaactcgcgaaaaaaacagccaag
tgtaccgccggaagcaccaggagctgcaagccatgcagatggagctgcagagccctgagtacaagctgagcaagct
ccgcacctcgaccatcatgaccgactacaaccccaactactgctttgctggcaagacctcctccatcagtgacc
tgaaggaggtgccgcggaaaaacatcaccctcattcggggtctgggccatggcgcctttggggaggtgtatg
aaggccaggtgtccggaatgcccaacgacccaagccccctgcaagtggctgtgaagacgctgcctgaag
tgtgctctgaacaggacgaactggatttcctcatggaagccctgatcatcagcaaattcaaccaccagaac
attgttcgctgcattggggtgagcctgcaatccctgccccggttcatcctgctggagctcatggcgggggg
agacctcaagtccttcctccgagagacccgccctcgcccgagccagccctcctccctggccatgctggacc
ttctgcacgtggctcgggacattgctgtggctgtcagtatttggaggaaaaaccacttcatccaccgagac
attgctgccagaaactgcctcttgacctgtccaggccctggaagagtggccaagattggagacttcggga
tggcccgagacatctacagggcgagctactatagaaagggaggctgtgccatgctgccagttaagtgga
tgccccagaggccttcatggaaggaatattcacttctaaaacagacacatggtcctttggagtgctgctat
gggaaatcttttctcttggatatatgccataccccagcaaaagcaaccaggaagttctggagtttgtcacca
gtggaggccggatggacccacccaagaactgccctgggcctgtataccggataatgactcagtgctggc
aacatcagcctgaagacaggcccaactttgccatcattttggagaggattgaatactgcacccaggaccc
ggatgtaatcaacaccgctttgccgatagaatatggtccacttgtggaagaggaagagaaagtgcctgtgaggccca
aggaccctgagggggttcctcctctcctggtctctcaacaggcaaaacggaggaggagcgcagcccagctgccccac
cacctctgcctaccacctcctctggcaaggctgcaaagaaacccacagctgcagaggtctctgttcgagtcctagaggg
ccggccgtggaaggggacacgtgaatatggcattctctcagtccaaccctccttcggagttgcacaaggtccacggat
ccagaaacaagcccaccagcttgtggaacccaacgtacggctcctggtttacagagaaacccaccaaaagaataatc
ctatagcaaagaaggagccacacgacaggggtaacctggggctggagggaagctgtactgtcccacctaacgttgca
actgggagacttccggggcctcactgctcctagagccctcttcgctgactgccaatatgaaggaggtacctctgttcag
gctacgtcacttcccttgtgggaatgtcaattacggctaccagcaacagggcttgcccttagaagccgctactgcccctgg
agctggtcattacgaggataccattctgaaaagcaagaatagcatgaaccagcctgggccctga

Figure 2B

MDGFAGSLDDSISAASTSDVQDRLSALESRVQQQEDEITVLKAALADVLRRLAISEDHVASVKKSVSSKGQ
PSPRAVIPMSCITNGSGANRKPSHTSAVSIAGKETLSSAAKSGTEKKKEKPQGQREKKEESHSNDQSPQIR
ASPSPQPSSQPLQIHRQTPESKNATPTKSIKRPSPAEKSHNSWENSDDSRNKLSKIPSTPKLIPKVTKTADK
HKDVIINQEGEYIKMFMRGRPITMFIPSDVDNYDDIRTELPPEKLKLEWAYGYRGKDCRANVYLLPTGEJ
VYFIASVVVLFNYEERTQRHYLGHTDCVKCLAIHPDKIRIATGQIAGVDKDGRPLQPHVRVWDSVTLSTL
QIIGLGTFERGVGCLDFSKADSGVHLCIIDDSNEHMLTVWDWQKKAKGAEIKTTNEVVLAVEFHPTDAN
TIITCGKSHIFFWTWSGNSLTRKQGIFGKYEKPKFVQCLAFLGNGDVLTGDSGGVMLIWSKTTVEPTPG
KGPKVYRRKHQELQAMQMELQSPEYKLSKLRTSTIMTDYNPNYCFAGKTSSISDLKEVPRKNITLI
RGLGHGAFGEVYEGQVSGMPNDPSPLQVAVKTLPEVCSEQDELDFLMEALIISKFNHQNIVR
CIGVSLQSLPRFILLELMAGGDLKSFLRETRPRPSQPSSLAMLDLLHVARDIACGCQYLEENH
FIHRDIAARNCLLTCPGPGRVAKIGDFGMARDIYRASYYRKGGCAMLPVKWMPPEAFMEGI
FTSKTDTWSFGVLLWEIFSLGYMPYPSKSNQEVLEFVTSGGRMDPPKNCPGPVYRIMTQCW
QHQPEDRPNFAIILERIEYCTQDPDVINTALPIEYGPLVEEEEKVPVRPKDPEGVPPLLVSQQAKR
EEERSPAAPPPLPTTSSGKAAKKPTAAEISVRVPRGPAVEGGHVNMAFSQSNPPSELHKVHGSRNK
PTSLWNPTYGSWFTEKPTKKNNPIAKKEPHDRGNLGLEGSCTVPPNVATGRLPGASLLLEPSSLTA
NMKEVPLFRLRHFPCGNVNYGYQQQGLPLEAATAPGAGHYEDTILKSKNSMNQPGP

ATGGACGGTTTCGCCGGCAGTCTCGATGATAGTATTTCTGCTGCAAGTACTTCTGATGTTCAAGATCG
CCTGTCAGCTCTTGAGTCACGAGTTCAGCAACAAGAAGATGAAATCACTGTGCTAAAGGCGGCTTTG
GCTGATGTTTTGAGGCGTCTTGCAATCTCTGAAGATCATGTGGCCTCAGTGAAAAAATCAGTCTCAAG
TAAAGGCCAACCAAGCCCTCGAGCAGTTATTCCCATGTCCTGTATAACCAATGGAAGTGGTGCAAAC
AGAAAACCAAGTCATACCAGTGCTGTCTCAATTGCAGGAAAAGAAACTCTTTCATCTGCTGCTAAAAG
TGGTACAGAAAAAAAGAAAGAAAAACCACAAGGACAGAGAGAAAAAAAGAGGAATCTCATTCTAATG
ATCAAAGTCCACAAATTCGAGCATCACCTTCTCCCCAGCCCTCTTCACAACCTCTCCAAATACACAGA
CAAACTCCAGAAAGCAAGAATGCTACTCCCACCAAAAGCATAAAACGACCATCACCAGCTGAAAAGT
CACATAATTCTTGGGAAAATTCAGATGATAGCCGTAATAAATTGTCGAAAATACCTTCAACACCCAAAT
TAATACCAAAAGTTACCAAAACTGCAGACAAGCATAAAGATGTCATCATCAACCAAGAAGGAGAATAT
ATTAAAATGTTTATGCGCGGTCGGCCAATTACCATGTTCATTCCTTCCGATGTTGACAACTATGATGAC
ATCAGAACGGAACTGCCTCCTGAGAAGCTCAAACTGGAGTGGGCATATGGTTATCGAGGAAAGGACT
GTAGAGCTAATGTTTACCTTCTTCCGACCGGGGAAATAGTTTATTTCATTGCATCAGTAGTAGTACTAT
TTAATTATGAGGAGAGAACTCAGCGACACTACCTGGGCCATACAGACTGTGTGAAATGCCTTGCTATA
CATCCTGACAAAATTAGGATTGCAACTGGACAGATAGCTGGCGTGGATAAAGATGGAAGGCCTCTAC
AACCCCACGTCAGAGTGTGGGATTCTGTTACTCTATCCACACTGCAGATTATTGGACTTGGCACTTTT
GAGCGTGGAGTAGGATGCCTGGATTTTTCAAAAGCAGATTCAGGTGTTCATTTATGTATTATTGATGA
CTCCAATGAGCATATGCTTACTGTATGGGACTGGCAGAAGAAAGCAAAAGGAGCAGAAATAAAGACA
ACAAATGAAGTTGTTTTGGCTGTGGAGTTTCACCCAACAGATGCAAATACCATAATTACATGCGGTAA
ATCTCATATTTTCTTCTGGACCTGGAGCGGCAATTCACTAACAAGAAAACAGGGAATTTTTGGGAAAT
ATGAAAAGCCAAAATTTGTGCAGTGTTTAGCATTCTTGGGGAATGGAGATGTTCTTACTGGAGACTCA
GGTGGAGTCATGCTTATATGGAGCAAAACTACTGTAGAGCCCACACCTGGGAAAGGACCTAAAGTGT
ACCGCCGGAAGCACCAGGAGCTGCAAGCCATGCAGATGGAGCTGCAGAGCCCTGAGTACAAG
CTGAGCAAGCTCCGCACCTCGACCATCATGACCGACTACAACCCCAACTACTGCTTTGCTGGC
AAGACCTCCTCCATCAGTGACCTGAAGGAGGTGCCGCGGAAAAACATCACCCTCATTCGGG
GTCTGGGCCATGGCGCCTTTGGGGAGGTGTATGAAGGCCAGGTGTCCGGAATGCCCAA
CGACCCAAGCCCCCTGCAAGTGGCTGTGAAGACGCTGCCTGAAGTGTGCTCTGAACAGG
ACGAACTGGATTTCCTCATGGAAGCCCTGATCATCAGCAAATTCAACCACCAGAACATTG
TTCGCTGCATTGGGGTGAGCCTGCAATCCCTGCCCCGGTTCATCCTGCTGGAGCTCATG
GCGGGGGGAGACCTCAAGTCCTTCCTCCGAGAGACCCGCCCTCGCCCGAGCCAGCCCTC
CTCCCTGGCCATGCTGGACCTTCTGCACGTGGCTCGGGACATTGCCTGTGGCTGTCAGT
ATTTGGAGGAAAACCACTTCATCCACCGAGACATTGCTGCCAGAAACTGCCTCTTGACCT

Figure 2B continued

GTCCAGGCCCTGGAAGAGTGGCCAAGATTGGAGACTTCGGGATGGCCCGAGACATCTAC
AGGGCGAGCTACTATAGAAAGGGAGGCTGTGCCATGCTGCCAGTTAAGTGGATGCCCCC
AGAGGCCTTCATGGAAGGAATATTCACTTCTAAAACAGACACATGGTCCTTTGGAGTGC
TGCTATGGGAAATCTTTTCTCTTGGATATATGCCATACCCCAGCAAAAGCAACCAGGAAG
TTCTGGAGTTTGTCACCAGTGGAGGCCGGATGGACCCACCCAAGAACTGCCCTGGGCCT
GTATACCGGATAATGACTCAGTGCTGGCAACATCAGCCTGAAGACAGGCCCAACTTTGC
CATCATTTTGGAGAGGATTGAATACTGCACCCAGGACCCGGATGTAATCAACACCGCTTT
GCCGATAGAATATGGTCCACTTGTGGAAGAGGAAGAGAAAGTGCCTGTGAGGCCCAAGGACC
CTGAGGGGGTTCCTCCTCTCCTGGTCTCTCAACAGGCAAAACGGGAGGAGGAGCGCAGCCCA
GCTGCCCCACCACCTCTGCCTACCACCTCCTCTGGCAAGGCTGCAAAGAAACCCACAGCTGCA
GAGATCTCTGTTCGAGTCCCTAGAGGGCCGGCCGTGGAAGGGGGACACGTGAATATGGCATT
CTCTCAGTCCAACCCTCCTTCGGAGTTGCACAAGGTCCACGGATCCAGAAACAAGCCCACCAG
CTTGTGGAACCCAACGTACGGCTCCTGGTTTACAGAGAAACCCACCAAAAAGAATAATCCTAT
AGCAAAGAAGGAGCCACACGACAGGGGTAACCTGGGGCTGGAGGGAAGCTGTACTGTCCCAC
CTAACGTTGCAACTGGGAGACTTCCGGGGGCCTCACTGCTCCTAGAGCCCTCTTCGCTGACTG
CCAATATGAAGGAGGTACCTCTGTTCAGGCTACGTCACTTCCCTTGTGGGAATGTCAATTACG
GCTACCAGCAACAGGGCTTGCCCTTAGAAGCCGCTACTGCCCCTGGAGCTGGTCATTACGAGG
ATACCATTCTGAAAAGCAAGAATAGCATGAACCAGCCTGGGCCCTGA

Figure 2C

*MNGQLDLSGKLIIKAQLGEDIRRIPIHNEDITYDELVLMMQRVFRGKLLSNDEVTIKYKDEDGDLI
TIFDSSDLSFAIQCSRILKLTLFVNGQPRPLESSQVKYLRRELIELRNKVNRLLDSLEPPGEPGPSTN
IPENVYRRKHQELQAMQMELQSPEYKLSKLRTSTIMTDYNPNYCFAGKTSSISDLKEVPRKNITLI
RGLGHGAFGEVYEGQVSGMPNDPSPLQVAVKTLPEVCSEQDELDFLMEALIISKFNHQNIVR
CIGVSLQSLPRFILLELMAGGDLKSFLRETRPRPSQPSSLAMLDLLHVARDIACGCQYLEENH
FIHRDIAARNCLLTCPGPGRVAKIGDFGMARDIYRASYYRKGGCAMLPVKWMPPEAFMEGI
FTSKTDTWSFGVLLWEIFSLGYMPYPSKSNQEVLEFVTSGGRMDPPKNCPGPVYRIMTQCW
QHQPEDRPNFAIILERIEYCTQDPDVINTALPIEYGPLVEEEEKVPVRPKDPEGVPPLLVSQQAKR,
EEERSPAAPPPLPTTSSGKAAKKPTAAEISVRVPRGPAVEGGHVNMAFSQSNPPSELHKVHGSRNK
PTSLWNPTYGSWFTEKPTKKNNPIAKKEPHDRGNLGLEGSCTVPPNVATGRLPGASLLLEPSSLTA
NMKEVPLFRLRHFPCGNVNYGYQQQGLPLEAATAPGAGHYEDTILKSKNSMNQPGP*

*ATGAACGGACAGTTGGATCTAAGTGGGAAGCTAATCATCAAAGCTCAACTTGGGGAGGATATTC
GGCGAATTCCTATTCATAATGAAGATATTACTTATGATGAATTAGTGCTAATGATGCAACGAGTT
TTCAGAGGAAAACTTCTGAGTAATGATGAAGTAACAATAAAGTATAAAGATGAAGATGGAGATC
TTATAACAATTTTTGATAGTTCTGACCTTTCCTTTGCAATTCAGTGCAGTAGGATACTGAAACTG
ACATTATTTGTTAATGGCCAGCCAAGACCCCTTGAATCAAGTCAGGTGAAATATCTCCGTCGAGA
ACTGATAGAACTTCGAAATAAAGTGAATCGTTTATTGGATAGCTTGGAACCACCTGGAGAACCA
GGACCTTCCACCAATATTCCTGAAAATGTGTACCGCCGGAAGCACCAGGAGCTGCAAGCCATG
CAGATGGAGCTGCAGAGCCCTGAGTACAAGCTGAGCAAGCTCCGCACCTCGACCATCATGAC
CGACTACAACCCCAACTACTGCTTTGCTGGCAAGACCTCCTCCATCAGTGACCTGAAGGAGGT
GCCGCGGAAAAACATCACCCTCATTCGGGGTCTGGGCCATGGCGCCTTTGGGGAGGTGT
ATGAAGGCCAGGTGTCCGGAATGCCCAACGACCCAAGCCCCCTGCAAGTGGCTGTGAAG
ACGCTGCCTGAAGTGTGCTCTGAACAGGACGAACTGGATTTCCTCATGGAAGCCCTGAT
CATCAGCAAATTCAACCACCAGAACATTGTTCGCTGCATTGGGGTGAGCCTGCAATCCC
TGCCCCGGTTCATCCTGCTGGAGCTCATGGCGGGGGGAGACCTCAAGTCCTTCCTCCGA
GAGACCCGCCCTCGCCCGAGCCAGCCCTCCTCCCTGGCCATGCTGGACCTTCTGCACGT
GGCTCGGGACATTGCCTGTGGCTGTCAGTATTTGGAGGAAAACCACTTCATCCACCGAG
ACATTGCTGCCAGAAACTGCCTCTTGACCTGTCCAGGCCCTGGAAGAGTGGCCAAGATT
GGAGACTTCGGGATGGCCCGAGACATCTACAGGGCGAGCTACTATAGAAAGGGAGGCT
GTGCCATGCTGCCAGTTAAGTGGATGCCCCAGAGGCCTTCATGGAAGGAATATTCACT
TCTAAAACAGACACATGGTCCTTTGGAGTGCTGCTATGGGAAATCTTTTCTCTTGGATAT
ATGCCATACCCCAGCAAAAGCAACCAGGAAGTTCTGGAGTTTGTCACCAGTGGAGGCCG
GATGGACCCACCCAAGAACTGCCCTGGGCCTGTATACCGGATAATGACTCAGTGCTGGC
AACATCAGCCTGAAGACAGGCCCAACTTTGCCATCATTTTGGAGAGGATTGAATACTGC
ACCCAGGACCCGGATGTAATCAACACCGCTTTGCCGATAGAATATGGTCCACTTGTGGAAGA
GGAAGAGAAAGTGCCTGTGAGGCCCAAGGACCCTGAGGGGGTTCCTCCTCTCCTGGTCTCTCA
ACAGGCAAAACGGGAGGAGGAGCGCAGCCCAGCTGCCCCACCACCTCTGCCTACCACCTCCT
CTGGCAAGGCTGCAAAGAAACCCACAGCTGCAGAGATCTCTGTTCGAGTCCCTAGAGGGCCG
GCCGTGGAAGGGGGACACGTGAATATGGCATTCTCTCAGTCCAACCCTCCTTCGGAGTTGCAC
AAGGTCCACGGATCCAGAAACAAGCCCACCAGCTTGTGGAACCCAACGTACGGCTCCTGGTTT
ACAGAGAAACCCACCAAAAAGAATAATCCTATAGCAAAGAAGGAGCCACACGACAGGGGTA*

Figure 2C continued

ACCTGGGGCTGGAGGGAAGCTGTACTGTCCCACCTAACGTTGCAACTGGGAGACTTCCGGGG
GCCTCACTGCTCCTAGAGCCCTCTTCGCTGACTGCCAATATGAAGGAGGTACCTCTGTTCAGG
CTACGTCACTTCCCTTGTGGGAATGTCAATTACGGCTACCAGCAACAGGGCTTGCCCTTAGAA
GCCGCTACTGCCCCTGGAGCTGGTCATTACGAGGATACCATTCTGAAAAGCAAGAATAGCATG
AACCAGCCTGGGCCCTGA

Figure 3A mdqfaqslddsisaastsdvqdrlsalesrvqqqedeitvlkaaladvlr
rlaisedhvasvkksvsskqqpspravipmscitngsqanrkpshtsavs
iaqketlssaaksqtekkkekpqqgrekkeeshsndqspqiraspspqps
sqplqihrqtpesknatptksikrpspaekshnswensddsrnklskips
tpklipkvtktadkhkdviinqegeyikmfmrgrpitmfi
psdvdnyddirtelppeklklewaygyrgkdcranvyllptgeivyfias
vvvlfnyeertqrhylghtdcvkclaihpdkiriatqqiaqvdkdgrplq
phvrvwdsvtlstlqiiqlgtfergvqcldfskadsgvhlcviddsnehm
ltvwdwqkkakgaeikttnevvlavefhptdantiitcqkshiffwtwsg
nsltrkqgifgkyekpkfvgclaflqnqdvltqdsqqvmliwsktttvept
pgkgpkgvyqiskqikahdgsvftlcqmrngmlltgggkdrkiilwdhdl
npereievpdqygtiravaeqkadqflvgtsrnfilrgtfndgfqievqg
htdelwglathpfkdllltcaqdrqvclwnsmehrlewtrlvdepghcad
fhpsgtvvaigthsgrwfvldaetrdlvsihtdgneqlsvmrysidgtfl
avgshdnfiylyvvsengrkysrygrctghssyithldwspdnkyimsns
gdyeilywdipngcklirnrsdckdidwttytcvlgfqvfgvwpegsdgt
dinalvrshnrkviavaddfckvhlfqypcskakapshkysahsshvtnv
sfthndshlistggkdmsiiqwklveklslpqnetvadttltkapvsste
sviqsntptpppsqplnetaeeesrissspptllensleqtvepsedhsee
eseegsqdlgeplyeepcneiskeqakatlledqqdpspss

Figure 3B atggacggttcgccggcagtctcgatgatagtatttctgctgcaagtacttctgatgttcaagatcgcctg
tcagctcttgagtcacgagtcagcaacaagaagatgaaatcactgtgctaaaggcggctttggctgat
gttttgaggcgtcttgcaatctctgaagatcatgtggcctcagtgaaaaaatcagtctcaagtaaaggcc
aaccaagccctcgagcagttattccatgtcctgtataaccaatggaagtggtgcaaacagaaaacca
agtcataccagtgctgtctcaattgcaggaaaagaaactcttcatctgctgctaaaagtggtacagaa
aaaaagaaagaaaaaccacaaggacagagagaaaaaaagaggaatctcattctaatgatcaaa
gtccacaaattcgagcatcaccttctcccagccctcttcacaacctctccaaatacacagacaaactc
cagaaagcaagaatgctactccaccaaaagcataaaacgaccatcaccagctgaaaagtcacat
aattcttgggaaaattcagatgatagccgtaataaaattgtcgaaaatacctttcaacac
ccaaattaataccaaaagttaccaaaactgcagacaagcataaagatgtcatcatcaaccaagaag
gagaatatattaaaatgttatgcgcggtcggccaattaccatgttcattcctccgatgttgacaactatg
atgacatcgaacggaactgcctcctgagaagctcaaactggagtgggcatatggttatcgaggaaa
ggactgtagagctaatgtttaccttcttccgaccggggaaatagtttatttcattgcatcagtagtaggact
atttaattatgaggagagaactcagcgacactaccttgggccatacagactgtgtgaaatgccttgctat
acatcctgacaaaattaggattgcaactggacagatagctggcgtggataaagatggaaggcctcta
caacccacgtcagagtgtgggattctgttactctatccacactgcagattattggacttggcactttgag
cgtggagtaggatgcctggattttttcaaaagcagattcaggtgttcatttatgtgttattgatgactccaat
gagcatatgcttactgtatgggactggcagaagaaagcaaaaggagcagaaataaagacaacaaa
tgaagttgttttggctgtggagtttcacccaacagatgcaaataccataattacatgcggtaaatctcata
tttcttctggacctggagcggcaattcactaacaagaaaacagggaatttttggqgaaatatgaaaagc
caaaattgtgcagtgttagcattcttggggaatggagatgttcttactggagactcaggtggagtcatg
cttatatggagcaaaactactgtagagcccacacctgggaaaggacctaaaggtgtatatcaaatcag
caaacaaatcaaagctcatgatggcagtgtgttcacactttgtcagatgagaaatgggatgttattaactgga
ggagggaaagacagaaaaataattctgtgggatcatgatctgaatcctgaaagagaaatagaggttcctga
tcagtatggcacaatcagagctgtagcagaaggaaaggcagatcaattttagtaggcacatcacgaaact
ttatttacgaggaacatttaatgatggcttccaaatagaagtacagggtcatacagatgagctttggggtctt
gccacacatccttcaaagatttgctcttgacatgtgctcaggacaggcaggtgtgcctgtggaactcaatg
gaacacaggctggaatggaccaggctggtagatgaaccaggacactgtgcagattttcatccaagtggca

Figure 3B continued cagtggtggccataggaacgcactcaggcaggtggttgttctggatgcagaaaccagagatctagtttct
atccacacagacgggaatgaacagctctctgtgatgcgctactcaatagatggtaccttcctggctgtagga
tctcatgacaactttatttacctctatgtagtctctgaaaatggaagaaaatatagcagatatggaaggtgcac
tggacattccagctacatcacacaccttgactggtccccagacaacaagtatataatgtctaactcgggaga
ctatgaaatattgtactgggacattccaaatggctgcaaactaatcaggaatcgatcggattgtaaggacatt
gattggacgacatatacctgtgtgctaggatttcaagtatttggtgtctggccagaaggatctgatgggaca
gatatcaatgcactggtgcgatcccacaatagaaaggtgatagctgttgccgatgactttgtaaagtccatc
tgtttcagtatccctgctccaaagcaaaggctcccagtcacaagtacagtgcccacagcagccatgtcacc
aatgtcagttttactcacaatgacagtcacctgatatcaactggtggaaaagacatgagcatcattcagtgga
aacttgtggaaaagttatctttgcctcagaatgagactgtagcggatactactctaaccaaagcccccgtctc
ttccactgaaagtgtcatccaatctaatactcccacaccgcctccttctcagcccttaaatgagacagctgaa
gaggaaagtagaataagcagttctcccacacttctggagaacagcctggaacaaactgtgggccaagtga
agaccacagcgaggaggagagtgaagagggcagcggagaccttggtgagcctcttatgaagagccat
gcaacgagataagcaaggagcaggccaaagccacccttctggaggaccagcaagacccttcgccctcg
tcctaacaccctggcttcagtgcaactcttttccttcagctgcatgtgattttgtgataaagttcaggtaacagg
atgggcagtgatggagaatcactgttgattgagattttggtttccatgtgatttgttttcttcaatagtcttattttc
agtctctcaaatacagccaacttaaagttttagtttggtgtttattgaaaattaaccaaacttaatactaggaga
agactgaatcattaatgatgtctcacaaattactgtgtacctaagtggtgtgatgtagatactggaaacaaaaa
cagcagttgcattgatttgaaaacaaaccccccttgttatctgaacatgttttcttcaggaacaaccagaggta
tcacaaacactgttactcatctactggctcagactgtactactttttttttttttttttcctgaaaaagaaaccagaa
aaaaatgtactcttactgagataccctctcaccccaaatgtgtaatggaaaattttaattaagaaaaacttcag
tttgccaagtgcaatggtgttgccttctttaaaaaatgccgtttttcttacactaccagtggatgtccagacatg
ctcttagtctactagagaggtgctgcctttctaagtcataatgaggaacagtcccttaattcttgtgtgcaact
ctgttttatcctagaactaagagagcattggtttgttaaagagctttcaatgtatattaaaaccttcaatactcag
aaatgatggattcctccaaggagtcctttactagcctaa acattctcaaatgtttgagattcaagtgaatggaaggaaaaccacatgcctttaaaactaaactgtaata
attacctggctaatttcagctaagccttcatcataatttgttccctcagtaataggagaaatatataaatac
agtaagtttagattattgaattggtgcttgaaatttattggttttgttgtaattttatacagattatatgagggataa
gatactcatcaaattgcaaattcttttttttacagaagtgtgggtaacagtcacagcagttttttttaccaacagc
atacttaacagacttgctgtgtagcagttttttttctggtggagttgctgtaagtcttgtaagtctaatgtggctat
cctactcttttgggcaatgcatgtattatgcattggaaaggtatttttttttaagttctgttggctagctatggttttc
agtacattcctactttaagagtaattactgacaaatatgtatttcctatatgtttatactttgattataaaaaagtat
tttgttttgattttttaacttgctgcattgttttgatactttctatttttttggtcaaatcatgtttagaaactttggatga
gttaagaagtcttaagtatgcaggcgtttacgtgattgtgccattccaaagtgcatcagaactgtcattcccft
ctaatatcttctcaggagtaatacaaatcaggtatttcatcatcatttggtaatatgaaaactccagtgaactcc
caaggacatttacaacatttatattcacacgctgtatggaagggtgtgggtgtgtgtgaagggggcgagtgg
agacactgtgtgtatctctagataagaagatatgcaccacgttgaaaatactcagtgtagatctctatgtgtat
aggtatctgtatatcttttcctttttgtttacaactgttaaaaaacctcaaaatagttctcttcaaaagaagagagatt
ccaagcaacccatctttcttcagtatgtatgttctgtacatactttatcggagcgcgccagtaagtatcaggcat
atatatctgtctgttagcaatgattattacatcatcagatcagcatgtgctatactccctgcaagaaatatactg
acatgaacaggcagttcttggagaagaaagagcatttctttaagtacctggggaatacagctctcagtgat
cagcagggagtttatttgaggacatcagtcacctttggggttgccatgtacaatgagatttataatcatgatac
tcttcggtggtagtttcaaaagacactactaatacgcaggaagcgtccagctatttaatgctggcaactactg
ttaatggtcagttaaatctgtgataatggttggaagtgggtgggggtatgaaattgtagatgttttagaaaaa
cttgtgaatgaaaatgaatccaagtgtttcatgtgaagatgttgagccattgctatcatgcattcctgtctcatg
gcagaaaatttgaagattaaaaaataaaataatcaaaatgtttcctctttctaaaaaaaaaaaaaaaaaa

Figure 4A

MGAIGLLWLLPLLLSTAAVGSGMGTGQRAGSPAAGSPLQPREPLSYSRLQ
RKSLAVDFVVPSLFRVYARDLLLPPSSSELKAGRPEARGSLALDCAPLLR
LLGPAPGVSWTAGSPAPAEARTLSRVLKGGSVRKLRRAKQLVLELGEEAI
LEGCVGPPGEAAVGLLQFNLSELFSWWIRQGEGRLRIRLMPEKKASEVGR
EGRLSAAIRASQPRLLFQIFGTGHSSLESPTNMPSPSPDYFTWNLTWIMK
DSFPFLSHRSRYGLECSFDFPCELEYSPPLHDLRNQSWSWRRIPSEEASQ
MDLLDGPGAERSKEMPRGSFLLLNTSADSKHTILSPWMRSSSEHCTLAVS
VHRHLQPSGRYIAQLLPHNEAAREILLMPTPGKHGWTVLQGRIGRPDNPF
RVALEYISSGNRSLSAVDFFALKNCSEGTSPGSKMALQSSFTCWNGTVLQ
NFEDGFCGWTQGTLSPHTPQWQVRTLKDARFQDHQDHALLLSTTDVPASE
SATVTSATFPAPIKSSPCELRMSWLIRGVLRGNVSLVLVENKTGKEQGRM
VWHVAAYEGLSLWQWMVLPLLDVSDRFWLQMVAWWGQGSRAIVAFDNISI
SLDCYLTISGEDKILQNTAPKSRNLFERNPNKELKPGENSPRQTPIFDPT
VHWLFTTCGASGPHGPTQAQCNNAYQNSNLSVEVGSEGPLKGIQIWKVPA
TDTYSISGYGAAGGKGGKNTMMRSHGVSVLGIFNLEKDDMLYILVGQQGE
DACPSTNQLIQKVCIGENNVIEEEIRVNRSVHEWAGGGGGGGGATYVFKM
KDGVPVPLIIAAGGGGRAYGAKTDTFHPERLENNSSVLGLNGNSGAAGGG
GGWNDNTSLLWAGKSLQEGATGGHSCPQAMKKWGWETRGGFGGGGGGCSS
GGGGGGGYIGGNAASNNDPEMDGEDGVSFISPLGILYTPALKVMEGHGEVN
IKHYLNCSHCEVDECHMDPESHKVICFCDHGTVLAEDGVSCIVSPTPEPH
LPLSLILSVVTSALVAALVLAFSGIMI<u>VYRRKHQELQAMQMELQSPEYKL
SKLRTSTIMTDYNPNYCFAGKTSSISDLKEVPRKNITLIRGLGHGAFGEV
YEGQVSGMPNDPSPLQVAVKTLPEVCSEQDELDFLMEALIISKFNHQNIV
RCIGVSLQSLPRFILLELMAGGDLKSFLRETRPRPSQPSSLAMLDLLHVA
RDIACGCQYLEENHFIHRDIAARNCLLTCPGPGRVAKIGDFGMARDIYRA
SYYRKGGCAMLPVKWMPPEAFMEGIFTSKTDWSFGVLLWEIFSLGYMPY
PSKSNQEVLEFVTSGGRMDPPKNCPGPVYRIMTQCWQHQPEDRPNFAIIL
ERIEYCTQDPDVINTALPIEYGPLVEEEEKVPVRPKDPEGVPPLLVSQQA</u>
KREEERSPAAPPPLPTTSSGKAAKKPTAAEVSVRVPRGPAVEGGHVNMAF
SQSNPPSELHKVHGSRNKPTSLWNPTYGSWFTEKPTKKNNPIAKKEPHDR
GNLGLEGSCTVPPNVATGRLPGASLLLEPSSLTANMKEVPLFRLRHFPCG
NVNYGYQQQGLPLEAATAPGAGHYEDTILKSKNSMNQPGP

Figure 4B

```
   1 agagacttgc gcgcacgcac agtcctctgg agatcaggtg gaaggagccg ctgggtacca
  61 aggactgttc agagcctctt cccatctcgg ggagagcgaa gggtgaggct gggcccggag
 121 agcagtgtaa acggcctcct ccggcgggat gggagccatc gggctcctgt ggctgctgcc
 181 gctgctgctt tccacggcag ctgtgggctc cgggatgggg accggccagc gcgcgggctc
 241 cccagctgcg gggccgccgc tgcagccccg agctactcgc gcctgcagag
 301 gaagagtctg gcagttgact tcgtggtgcc ctcgctcttc cgtgtctacg cccgggacct
 361 actgctgcca ccatcctcct cggagctgaa ggctggcagg cccgaggccc gcggctcgct
 421 agctctggac tgcgccccgc tgctcaggtt gctggggccg gcgccggggg tctcctggac
 481 cgccggttca ccagccccgg cagaggcccg gacgctgtcc agggtgctga agggcggctc
 541 cgtgcgcaag ctccgcgtg ccaagcagtt ggtgctggag ctggcgagg aggcgatctt
 601 ggagggttgc gtcgggcccc ccggggaggc ggctgtgggg ctgctccagt tcaatctcag
 661 cgagctgttc agttggtgga ttcgccaagg cgaagggcga ctgaggatcc gcctgatgcc
 721 cgagaagaag gcgtcggaag tgggcagaga gggaagctg tccgcggcaa ttcgcgcctc
 781 ccagccccgc cttctcttcc agatcttcgg gactggtcat agctccttgg aatcaccaac
 841 aaacatgcct tctccttctc ctgattattt tacatggaat ctcacctgga taatgaaaga
 901 ctccttccct ttcctgtctc atcgcagccg atatggtctg gagtgcagct ttgacttccc
 961 ctgtgagctg gagtattccc ctccactgca tgacctcagg aaccagagct ggtcctggcg
1021 ccgcatcccc tccgaggagg cctcccagat ggacttgctg gatgggcctg gggcagagcg
1081 ttctaaggag atgccagag gctcctttct cctttctcaac acctcagctg actccaagca
1141 caccatcctc agtccgtgga tgaggagca cagtgagcac tgcacctgg ccgtctcggt
1201 gcacaggcac ctgcagccct ctggaaggta cattgcccag ctgctgcccc acaacgaggc
1261 tgcaagagag atcctcctga tgccactcc agggaagcat ggttggacag tgctccaggg
1321 aagaatcggg cgtccagaca acccatttcg agtggccctg aatacatct ccagtggaaa
1381 ccgcagcttg tctgcagtgg acttcttgc ctgaagaac tgcagtgaag gaacatcccc
1441 aggctccaag atggcctgc agagctcctt cacttgttgg aatgggacag tcctccagct
```

Figure 4B continued

```
1501 tgggcaggcc tgtgacttcc accaggactg tgcccaggga gaagatgaga gccagatgtg
1561 ccggaaactg cctgtgggtt tttactgcaa ctttgaagat ggcttctgtg gctggaccca
1621 aggcacactg tcaccccaca ctcctcagtg gcaggtcagg accctaaagg atgcccggtt
1681 ccaggaccac caagaccatg ctctattgct cagtaccact gatgtccccg cttctgaaag
1741 tgctacagtg accagtgcta cgtttcctgc accgatcaag agctctccat gtgagctccg
1801 aatgtcctgg ctcattcgtg gagtcttgag gggaaacgtg tccttggtgc tagtggagaa
1861 caaaaccggg aaggagcaag gcaggatggt ctggcatgtc gccgcctatg aaggcttgag
1921 cctgtggcag tggatggtgt tgcctctcct cgatgtgtct gacaggttct ggctgcagat
1981 ggtcgcatgg tggggacaag gatccagagc catcgtggct tttgacaata tctccatcag
2041 cctggactgc tacctcacca ttagcggaga ggacaagatc ctgcagaata cagcacccaa
2101 atcaagaaac ctgtttgaga gaaacccaaa caaggagctg aaacccgggg aaaattcacc
2161 aagacagacc cccatctttg accctacagt tcattggctg ttcaccacat gtggggccag
2221 cgggccccat ggccccaccc aggcacagtg caacaacgcc taccagaact ccaacctgag
2281 cgtggaggtg gggagcgagg gccccctgaa aggcatccag atctggaagg tgccagccac
2341 cgacacctac agcatctcgg gctacggagc tgctggcggg aaaggcggga agaacaccat
2401 gatgcggtcc cacggggtgt ctgtgctggg catcttcaac ctggagaagg atgacatgct
2461 gtacatcctg gttgggcagc agggagagga cgcctgcccc agtacaaacc agttaatcca
2521 gaaagtctgc attggagaga acaatgtgat agaagaagaa atccgtgtga acagaagcgt
2581 gcatgagtgg gcaggaggcg gaggaggagg gggtggagcc acctacgtat ttaagatgaa
2641 ggatggagtg ccggtgcccc tgatcattgc agccggaggt ggtggcaggg cctacggggc
2701 caagacagac acgttccacc cagagagact ggagaataac tcctcggttc tagggctaaa
2761 cggcaattcc ggagccgcag gtggtggagg tggctggaat gataacactt ccttgctctg
2821 ggccggaaaa tctttgcagg agggtgccac cggaggacat tcctgcccccc aggccatgaa
2881 gaagtggggg tgggagacaa gaggggggttt cggaggggggt ggagggggggt gctcctcagg
2941 tggaggaggc ggaggatata taggcggcaa tgcagcctca aacaatgacc ccgaaatgga
3001 tggggaagat ggggtttcct tcatcagtcc actgggcatc ctgtacaccc cagctttaaa
3061 agtgatgaa ggccacgggg aagtgaatat taagctattat ctaaactgca gtcactgtga
3121 ggtagacgaa tgtcacatgg accctgaaag ccacaaggtc atctgcttct gtgaccacgg
3181 gacggtgctg gctgaggatg gcgtctcctg cattgtgtca cccacccgg agccacacct
3241 gccactctcg ctgatcctct ctgtggtgac ctctgccctc gtggccgccc tggtcctggc
3301 tttctccggc atcatgattg tgtaccgccg gaagcaccag gagctgcaag ccatgcagat
3361 ggagctgcag agccctgagt acaagctgag caagctccgc acctcgacca tcatgaccga
3421 ctacaacccc aactactgct ttgctggcaa gacctcctcc atcagtgacc tgaaggaggt
3481 gccgcggaaa aacatcaccc tcattcgggg tctgggccat ggcgccttttg gggaggtgta
3541 tgaaggccag gtgtccggaa tgcccaacga cccaagcccc ctgcaagtgg ctgtgaagac
3601 gctgcctgaa gtgtgctctg aacaggacga actggatttc ctcatggaag ccctgatcat
3661 cagcaaattc aaccaccaga acattgttcg ctgcattggg gtgagcctgc aatccctgcc
3721 ccggttcatc ctgctggagc tcatggcggg gggagacctc aagttcctcc tccgagagac
3781 ccgcccgcac caggagccac cctcctccct ggccatgctg gaccttctgc acgtgcctcg
3841 ggacattgcc tgtggctgtc agtatttgga ggaaaaccac ttcatccacc gagacattgc
3901 tgccagaaac tgcctcttga cctgtccagg ccctggaaga gtggccaaga ttggagactt
3961 cgggatggcc cgagacatct acaggggcga gctactataga aagggaggct gtgccatgct
4021 gccagttaag tggatgcccc cagaggcctt catggaagga atattcactt ctaaaacaga
4081 cacatggtcc tttggagtgc tgctatggga aatctttttct cttggatata tgccataccc
4141 cagcaaaagc aaccaggaag ttctggagtt tgtcaccagt ggaggccgga tggacccacc
4201 caagaactgc cctgggcctg tataccggat aatgactcag tgctggcaac atcagcctga
4261 agacaggccc aactttgcca tcattttgga gaggattgaa tactgcaccc aggacccgga
4321 tgtaatcaac accgctttgc cgatagaata tggtccactt gtggaagagg aagagaaagt
4381 gcctgtgagg cccaaggacc ctgaggggt tcctcctctc ctggtctctc aacaggcaaa
4441 acgggaggag gagcgcagcc cagctgcccc accacctctg cctaccacct cctctggcaa
4501 ggctgcaaag gaaacccacag ctgcagaggt ctctgttcga gtccctagag ggccggccgt
4561 ggaaggggga cacgtgaata tggcattctc tcagtccaac cctccttcgg agttgcacag
4621 ggtccacgga tccagaaata agcccaccag cttgtggaac ccaacgtacg gctcctggtt
4681 tacagagaaa cccaccaaaa agaataatcc tatagcaaag aaggagccac acgagagggg
4741 taacctgggg ctggagggaa gctgtactgt cccacctaac gttgcaactg ggagacttcc
4801 gggggcctca ctgctcctag agccctcttc gctgactgcc aatatgaagg aggtacctct
4861 gttcaggcta cgtcacttcc cttgtgggaa tgtcaattac ggctaccagc aacagggctt
4921 gcccttagaa gccgctactg cccctggagc tggtcattac gaggatacca ttctgaaaag
4981 caagaatagc atgaaccagc ctgggccctg agctcggtcg cacactcact tctcttcctt
5041 gggatcccta agaccgtgga ggagagagag gcaatcaatg gctcctttca caaaccagag
5101 accaaatgtc acgttttgtt ttgtgccaac ctattttgaa gtaccaccaa aaaagctgta
5161 ttttgaaaat gctttagaaa ggttttgaa atgggttcat cctattcttt cgaaagaaga
5221 aaatatcatc aaaatgagtg ataaatacaa ggccagatgt ggttgcataa ggttttatg
5281 catgtttgtt gta
```

Figure 4C

MNGQLDLSGKLIVKAQLGEDIRRIPIHNEDITYDELVLMMQRVFRGKLLS
NDEVTIKYKDEDGDLITIFDSSDLSFAIQCSRILKLTLFVNGQPRPLESS
QVKYLRRELIELRNKVNRLLDSLEPPGEPGPSTNIPENDTVDGREEKSAS
DSSGKQSTQVMAASMSAFDPLKNQDEINKNVMSAFGLTDDQVSGPPSAPA
EDRSGTPDSIASSSSAAHPPGVQPQQPPYTGAQTQAGQIEGQMYQQYQQQ
AGYGAQQPQAPPQQPQQYGIQYSASYSQQTGPQQPQQFQGYGQQPTSQAP
APAFSGQPQQLPAQPPQQYQASNYPAQTYTAQTSQPTNYTVAPASQPGMA
PSQPGAYQPRPGFTSLPGSTMTPPPSGPNPYARNRPPFGQGYTQPGPGYR

Figure 4D

ATGAACGGACAGTTGGATCTAAGTGGGAAGCTAATCATCAAAGCTCAACTTGGGG
AGGATATTCGGCGAATTCCTATTCATAATGAAGATATTACTTATGATGAATTAGT
GCTAATGATGCAACGAGTTTTCAGAGGAAAACTTCTGAGTAATGATGAAGTAACA
ATAAAGTATAAAGATGAAGATGGAGATCTTATAACAATTTTTGATAGTTCTGACC
TTTCCTTTGCAATTCAGTGCAGTAGGATACTGAAACTGACATTATTTGTTAATGG
CCAGCCAAGACCCCTTGAATCAAGTCAGGTGAAATATCTCCGTCGAGAACTGATA
GAACTTCGAAATAAAGTGAATCGTTTATTGGATAGCTTGGAACCACCTGGAGAAC
CAGGACCTTCCACCAATATTCCTGAAAATGATACTGTGGATGGTAGGGAAGAAAA
GTCTGCTTCTGATTCTTCTGGAAAACAGTCTACTCAGGTTATGGCAGCAAGTATG
TCTGCTTTTGATCCTTTAAAAAACCAAGATGAAATCAATAAAAATGTTATGTCAG
CGTTTGGCTTAACAGATGATCAGGTTTCAGGGCCACCCAGTGCTCCTGCAGAAGA
TCGTTCAGGAACACCCGACAGCATTGCTTCCTCCTCCTCAGCAGCTCACCCACCA
GGCGTTCAGCCACAGCAGCCACCATATACAGGAGCTCAGACTCAAGCAGGTCAGA
TTGAAGGTCAGATGTACCAACAGTACCAGCAACAGGCCGGCTATGGTGCACAGCA
GCCGCAGGCTCCACCTCAGCAGCCTCAACAGTATGGTATTCAGTATTCAGCAAGC
TATAGTCAGCAGACTGGACCTCAACAACCTCAGCAGTTCCAGGGATATGGCCAGC
AACCAACTTCCCAGGCACCAGCTCCTGCCTTTCTGGTCAGCCTCAACAACTGCC

Figure 4D continued

```
TGCTCAGCCGCCACAGCAGTACCAGGCGAGCAATTATCCTGCACAAACTTACACT
GCCCAAACTTCTCAGCCTACTAATTATACTGTGGCTCCTGCCTCTCAACCTGGAA
TGGCTCCAAGCCAACCTGGGGCCTATCAACCAAGACCAGGTTTTACTTCACTTCC
TGGAAGTACCATGACCCCTCCTCCAAGTGGGCCTAATCCTTATGCGCGTAACCGT
CCTCCCTTTGGTCAGGGCTATACCCAACCTGGACCTGGTTATCGATAAGGAGGCT
CCTCTACACCAATTAATGTAGCTGCTAGCTATTGGCCTCCCAAAAGACTCCAGTA
CTATTTTAATTTGTATTGAAGAAGTTCAGAAATTTAAAAGCAGAGCATTTTTTAT
GATATCATTGTTGGTGTTAATTGAAAGTATAATTTGCTGGAACACAAAGACCAAA
ATGAAAGTTTTTTCCTCCCTGCTTAAAAATGTAGCAGCTTCTTAGTTACTTTGGA
ACACTACTCTTACATGTATAAAGTGATTGACTTGACTTTCTAGCTTCCCTTGTCC
GGAGGATATTAAAATGCTAGGGTGAGGTTTAGCCATCTTACTTGGCTTTTACTAT
TAACATGATGTACTAAAGTAGAGCCCTTTGAGAATACAAGATATTATGTATAAAA
TGTAACACTGATGATAGGTTAATAAAGATGATTGAATCCATTAAAAAAAAAAA
```

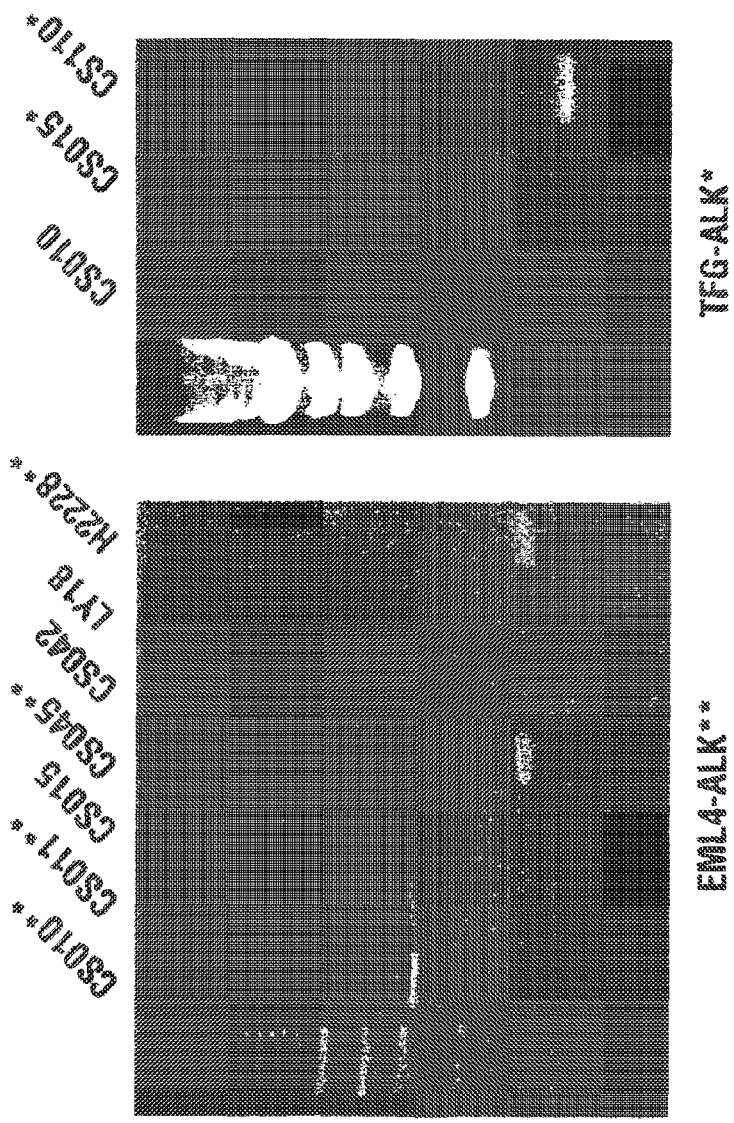

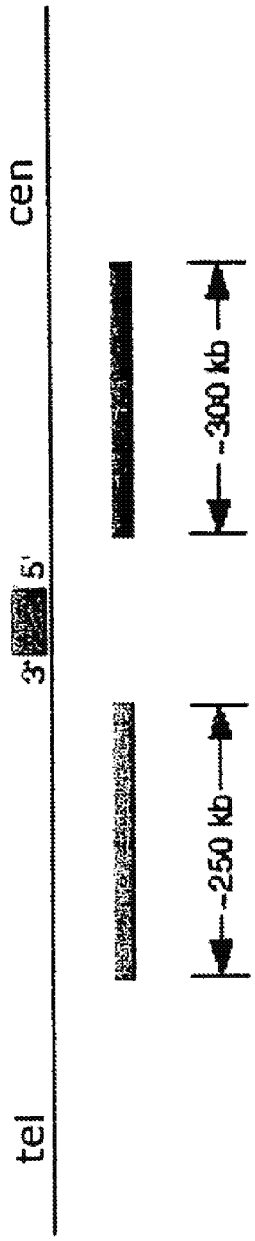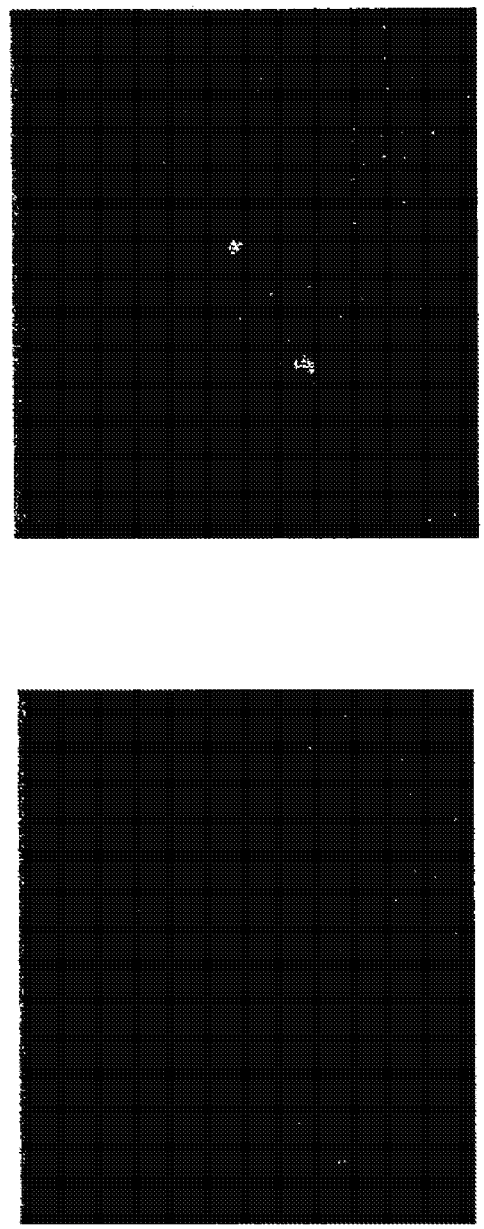
Figure 6

METHODS OF TREATING NON-SMALL CELL LUNG CARCINOMA (NSCLC)

RELATED APPLICATIONS

This application is a continuation of U.S. Ser. No. 14/870, 154, filed Sep. 30, 2015, which is a divisional of U.S. Ser No. 13/618,400, filed Sep. 14, 2012, which is a continuation of U.S. Ser. No. 12/891,987, filed Sep. 28, 2010, now U.S. Pat. No. 8,377,642, which is a continuation of U.S. Ser. No. 12/714,457, filed Feb. 27, 2010, now U.S. Pat. No. 8,288, 102, which is a continuation of U.S. Ser. No. 11/787,132, filed Apr. 13, 2007, now U.S. Pat. No. 7,700,339, which claims priority to, and the benefit of, U.S. Ser. No. 60/792, 364, filed Apr. 14, 2006, the disclosures of which are hereby incorporated herein in their entirety by reference.

FIELD OF THE INVENTION

The invention relates generally to proteins and genes involved in cancer, and to the detection, diagnosis and treatment of cancer.

BACKGROUND OF THE INVENTION

Many cancers are characterized by disruptions in cellular signaling pathways that lead to aberrant control of cellular processes, or to uncontrolled growth and proliferation of cells. These disruptions are often caused by changes in the activity of particular signaling proteins, such as kinases. Among these cancers are solid tumors, like non-small cell lung carcinoma (NSCLC). NSCLC is the leading cause of cancer death in the United States, and accounts for about 87% of all lung cancers. There are about 151,000 new cases of NSCLC in the United States annually, and it is estimated that over 120,000 patients will die annually from the disease in the United States alone. See "Cancer Facts and Figures 2005," American Cancer Society. NSCLC, which comprises three distinct subtypes, is often only detected after it has metastasized, and thus the mortality rate is 75% within two years of diagnosis.

It is known that gene deletions and/or translocations resulting in kinase fusion proteins with aberrant signaling activity can directly lead to certain cancers. For example, it has been directly demonstrated that the BCR-ABL oncoprotein, a tyrosine kinase fusion protein, is the causative agent in human chronic myelogenous leukemia (CML). The BCR-ABL oncoprotein, which is found in at least 90-95% of CML cases, is generated by the translocation of gene sequences from the c-ABL protein tyrosine kinase on chromosome 9 into BCR sequences on chromosome 22, producing the so-called Philadelphia chromosome. See, e.g. Kurzock et al., *N. Engl. J. Med.* 319: 990-998 (1988). The translocation is also observed in acute lymphocytic leukemia and NSCLC cases.

Gene translocations and deletions leading to mutant or fusion proteins implicated in a variety of other cancers have been described. For example, Falini et al., *Blood* 99(2): 409-426 (2002), review translocations known to occur in hematological cancers, including the NPM-ALK fusion found in ALCL. To date, only a limited number of gene translocations, deletions, and mutant proteins occurring in lung cancers have been described, including the t(15;19) translocation involving Notch3. See Dang et al., *J. Natl. Can. Instit.* 92(16): 1355-1357 (2000). Defects in RNA Binding Protein-6 (EML-4) expression and/or activity have been found in small cell and non-small cell lung carcinomas. See Drabkin et al., *Oncogene* 8(16): 2589-97 (1999). However, to date, no translocations or deletions in human NSCLC cancer that involve protein kinases have been described.

Defects in ALK kinase expression resulting from the fusion of NPM to ALK in large cell anaplastic lymphoma have been described. See Morris et al., 1994; Shiota et al., 1994. The fusion of ALK to moesin, non-muscle myosin heavy chain 9 (Tort et al. 2001), clarthrin heavy chain (Touriol et al., 2000; Bridge et al., 2001), tropomyosin 3 (TPM3) (Lamant et al., 1999), TRK-fused gene (TGF) (Hernandez et al., *Am. J. Path.* 160(4): 1487-1493 (2002)) and other genes have been described. In particular, the TGF-ALK fusion was reported in non-solid lymphoma, but to date this fusion has not been described in solid tumors. The general role of ALK in cancer has been described. See Pulford et al., *J. Cell Physiol.* 199(3): 330-358 (2004). However, to date, no defects in EML-4 expression and/or activation have been described.

Identifying mutations in human cancers is highly desirable because it can lead to the development of new therapeutics that target such fusion or mutant proteins, and to new diagnostics for identifying patients that have such gene mutations. For example, BCR-ABL has become a target for the development of therapeutics to treat leukemia. Most recently, Gleevec® (Imatinib mesylate, STI-571), a small molecule inhibitor of the ABL kinase, has been approved for the treatment of CML. This drug is the first of a new class of anti-proliferative agents designed to interfere with the signaling pathways that drive the growth of tumor cells. The development of this drug represents a significant advance over the conventional therapies for CML and ALL, chemotherapy and radiation, which are plagued by well known side-effects and are often of limited effect since they fail to specifically target the underlying causes of the malignancies. Likewise, reagents and methods for specifically detecting BCR-ABL fusion protein in patients, in order to identify patients most likely to respond to targeted inhibitors like Gleevec®, have been described.

Accordingly, there remains a need for the identification of novel gene mutations, such as translocations or deletions, resulting in fusion or mutant proteins implicated in the progression of human cancers, particularly solid tumors, including lung cancers like NSCLC, and the development of new reagents and methods for the study and detection of such fusion proteins. Identification of such fusion proteins will, among other things, desirably enable new methods for selecting patients for targeted therapies, as well as for the screening of new drugs that inhibit such mutant/fusion proteins.

SUMMARY OF THE INVENTION

In accordance with the invention, novel gene deletion mutations occurring in human chromosome 2 that result in fusion proteins combining part of Anaplastic Lymphoma Kinase (ALK) with a secondary protein have now been identified in the human solid tumor non-small cell lung carcinoma (NSCLC). Secondary proteins involved in the ALK fusions include Echinoderm Microtubule-Associated Protein-Like 4 (EML-4) and TRK-Fused Gene (TFG). The mutant/fusion ALK kinases have presently been observed in non-small cell lung carcinoma patient samples.

The invention therefore provides, in part, isolated polynucleotides and vectors encoding the disclosed mutant/fusion ALK polypeptides, probes and assays for detecting them, isolated mutant/fusion ALK polypeptides, recombinant mutant polypeptides, and reagents for detecting the mutant ALK polynucleotides and polypeptides. The disclosed identification of these new mutant ALK kinases and translocations/deletions enables new methods for determining the presence of mutant ALK polynucleotides or polypeptides in a biological sample, methods for screening for compounds that inhibit the mutant kinase protein, and methods for inhibiting the progression of a cancer characterized by the expression of mutant ALK polynucleotides or polypeptides, which are also provided by the invention. The aspects and embodiments of the invention are described in more detail below.

BRIEF DESCRIPTION OF THE DRAWINGS

FIG. 2A—is the amino acid sequence (1 letter code) of human EML4-ALK fusion protein (short variant) (SEQ ID NO: 1) (top panel) with coding DNA sequence also indicated (SEQ ID NO: 2) (bottom panel); the residues of the EML-4 moiety are in italics, while the residues of the kinase domain of ALK are in bold.

FIG. 2B—is the amino acid sequence (1 letter code) of human EML4-ALK fusion protein (long variant) (SEQ ID NO: 18) (top panel) with coding DNA sequence also indicated (SEQ ID NO: 19) (bottom panel); the residues of the EML-4 moiety are in italics, while the residues of the kinase domain of ALK are in bold.

FIG. 2C—is the amino acid sequence (1 letter code) of human TFG-ALK fusion protein (SEQ ID NO: 20) (top panel) with coding DNA sequence also indicated (SEQ ID NO: 21) (bottom panel); the residues of the TFG moiety are in italics, while the residues of the kinase domain of ALK are in bold.

FIGS. 3A-3B—is the amino acid sequence (1 letter code) of human EML-4 protein (SEQ ID NO: 3) (SwissProt Accession No. 061936) with coding DNA sequence also indicated (SEQ ID NO: 4) (GeneBank Accession No. NM019063); the residues retained in the short variant deletion mutant are underlined, while the residues retained in long variant and italicized.

FIGS. 4A-4B—is the amino acid sequence (1 letter code) of human ALK kinase (SEQ ID NO: 5) (SwissProt Accession No. Q9UM73) with coding DNA sequence also indicated (SEQ ID NO: 6) (GeneBank Accession No. HSU66559); the residues retained in the deletion mutants are underlined, while the residues of the kinase domain are in bold.

FIGS. 4C-4D—is the amino acid sequence (1 letter code) of human TFG protein (SEQ ID NO: 22) (SwissProt Accession No. Q92734) with coding DNA sequence also indicated (SEQ ID NO: 23) (GeneBank Accession No. NM006070); the residues retained in the deletion mutant are underlined.

FIG. 5A-5D—are gels depicting (5A) detection of ALK via the 5' RACE product with ALK primers after 2 rounds of PCR; UAP stands for Universal Amplification Primer, GSP for Gene Specific Primer, (5B) detection of the fusion gene formed by the EML-4 and ALK deletion mutant by RT-PCR, (5C) detection of the EML4-ALK fusion gene (short and long variants) in human NSCLC tumor samples by 5' RACE, and (5D) detection of the TFG-ALK fusion gene in human NSCLC tumor samples by 5' RACE.

FIG. 6—is an image depicting the detection of the fusion gene formed by the EML-4 and ALK translocation in H2228 cells by FISH assay employing a dual-color (orange/green) break-apart probe comprising probes to opposite sides of the ALK gene breakpoint 2p23; probe sizes and locations are shown in the upper panel.

DETAILED DESCRIPTION OF THE INVENTION

Figure 1A:
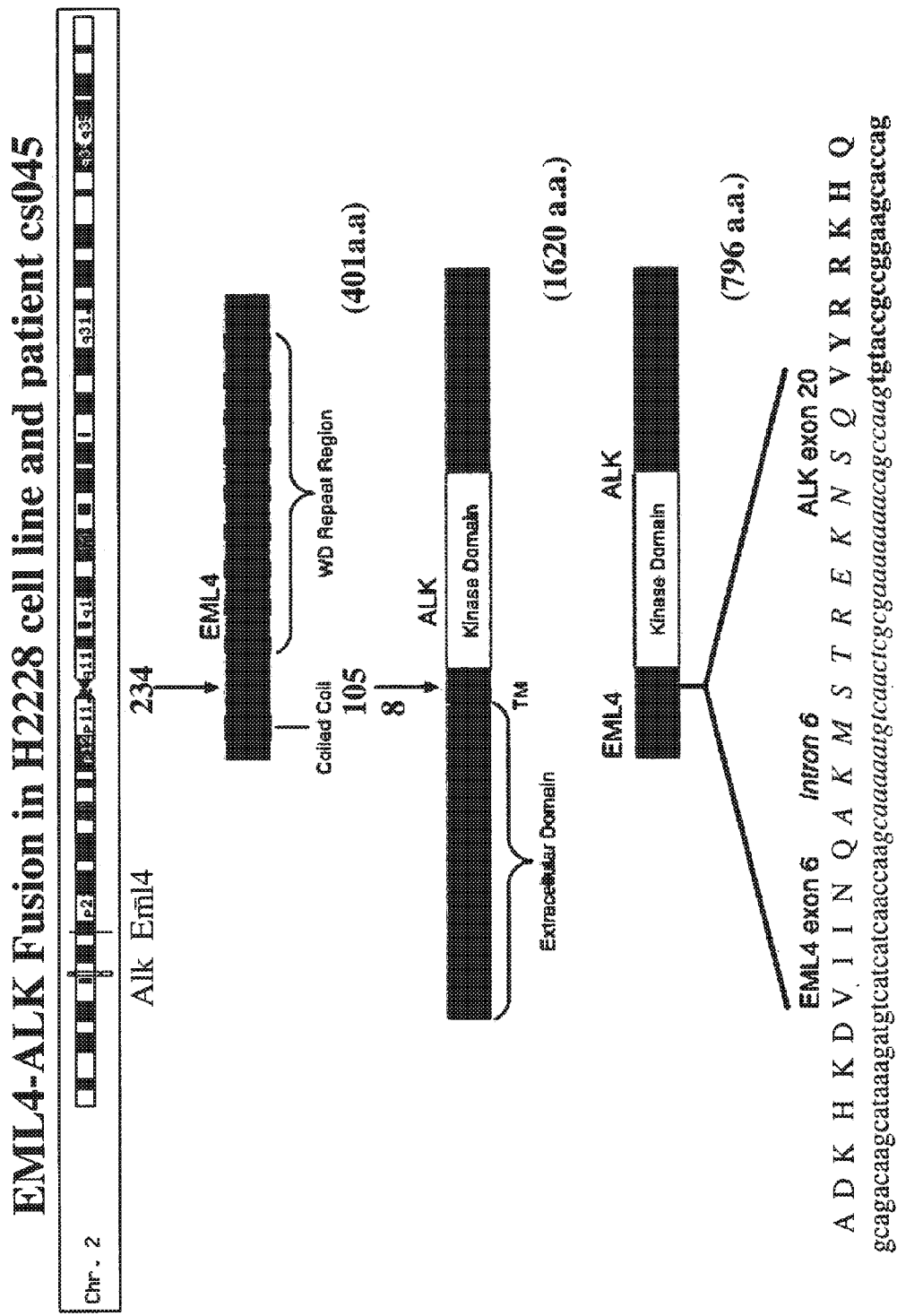
FIG. 1A—shows the locations of the EML-4 gene and ALK gene on chromosome 2 (panel A), and the domain locations of full-length EML-4 and ALK proteins as well as those of EML4-ALK fusion protein (short variant) (panel B); the fusion junction occurs at amino acids 233-234, and the fusion protein includes the kinase domain (but not the transmembrane and extracellular domains) of ALK. Also shown (in panel B) the DNA (and protein) sequence of the EML4 exon 6/intron6/ALK exon 20 fusion junction region (SEQ ID NO: 7 and SEQ ID NO: 8, respectively).

In accordance with the invention, previously unknown gene deletions and translocations that result in mutant kinase fusion proteins, combining part of Anaplastic Lymphoma Kinase (ALK) with a portion of a secondary protein, have now been identified in the human solid tumor non-small cell lung carcinoma (NSCLC). Secondary proteins involved in the discovered ALK fusions include Echinoderm Microtubule-Associated Protein-Like 4 (EML-4) and TRK-Fused Gene (TFG).

The two disclosed deletions, which occurs between the EML4 and ALK genes on chromosome 2, produce fusion proteins that combines the N-terminus of EML-4, a 401 amino acid microtubule binding protein, with the kinase domain and c-terminus of ALK, a 1620 amino acid membrane tyrosine kinase. The resulting EML4-ALK fusion proteins, which are 796 amino acids (short variant) and 1059 amino acids (long variant) respectively, and retain ALK kinase activity, are expected to drive the proliferation and survival of a subset of human solid tumors, including NSCLC.

The disclosed translocation, which occurs between the TFG gene on chromosome 6 and the ALK gene on chromosome 2, produces a fusion protein that combines the N-terminus of TFG, a 400 amino acid protein, with the kinase domain and c-terminus of ALK, a 1620 amino acid membrane tyrosine kinase. The resulting TFG-ALK fusion protein, which is 701 amino acids, has previously been observed in non-solid human lymphoma (Hemandez et al. (2002), supra.), but has not previously been described in solid tumors. The TFG-ALK fusion protein retains ALK kinase activity, and is expected to drive the proliferation and survival of a subset of human solid tumors, including NSCLC.

Although a few gene translocations or deletions that result in aberrant fusion proteins have been described in NSCLC, including the t(15;19) translocation involving Notch3 (see Dang et al., supra.), the presently disclosed EML4-ALK deletion mutants and fusion protein are novel. Similarly, the TFG-ALK translocation mutant and fusion protein, though known in non-solid tumors like lymphoma, is novel in the solid tumor NSCLC. EML-4 is a microtubule-associated protein that is expressed in most human tissues. To date, no defects in EML-4 expression and/or activity have been reported. ALK is a membrane tyrosine kinase, and is expressed, in humans, in brain and CNS tissues, also small intestine and testis, but not in normal lymphoid cells. It plays an important role in the normal development and function of the nervous system (Iwahara et al., 1997).

Defects in ALK expression and/or activation have been found in large cell anaplastic lymphoma and neuroblastoma (see Morris et al., 1994, Osajima-Hakomori et al., 2005). The fusion of ALK to moesin, non-muscle myosin heavy chain 9, clarthrin heavy chain, tropomyosin 3 (TPM3), TRK-fused gene (TFG), and other genes has been described. See Tort et al.; Touriol et al., Hemandez et al., supra.). Interestingly, the disclosed fusion of EML-4 to ALK (short variant) occurs at precisely the same point in wild type ALK (amino acid 1058) as previously described for other ALK fusion mutants.

As further described below, the EML4-ALK deletion mutants and the expressed fusion proteins have presently been isolated and sequenced, and cDNAs for expressing the fusion proteins produced. Accordingly, the invention provides, in part, isolated polynucleotides that encode EML4-ALK fusion polypeptides, nucleic acid probes that hybridize to such polynucleotides, and methods, vectors, and host cells for utilizing such polynucleotides to produce recombinant mutant ALK polypeptides. The invention also provides, in part, isolated polypeptides comprising amino acid sequences encoding EML4-ALK fusion polypeptides, recombinant mutant polypeptides, and isolated reagents that specifically bind to and/or detect EML4-ALK fusion polypeptides, but do not bind to or detect either wild type EML-4 or wild type ALK. These aspects of the invention, which are described in further detail below, will be useful, inter alia, in further studying the mechanisms of cancers driven by mutant ALK kinase expression/activity, for identifying solid tumors (e.g. carcinomas including lung carcinomas and sarcomas) and other cancers characterized by the disclosed ALK deletion and translocation mutations and/or fusion protein, or expression/activity of mutant ALK kinase, and in practicing methods of the invention as further described below.

The identification of the novel ALK kinase mutants and gene deletion and translocation mutations has important implications for the potential diagnosis and treatment of solid tumors, such as NSCLC, that are characterized by one or more of these fusion proteins. NSCLC, for example, is often only detected after it has metastasized, and thus the mortality rate is 75% within two years of diagnosis. Accordingly, the ability to identify, as early as possible, patients having gene mutations that may lead to NSCLC, would be highly desirable.

Therefore, the discovery of the EML4-ALK fusion proteins (short and long variants) resulting from gene deletion and the TFG-ALK fusion protein resulting from gene translocation, which are expected to drive proliferation and survival of a solid tumor, NSCLC, enables important new methods for accurately identifying mammalian solid tumors, including lung cancers (such as NSCLC), as well as other cancers, in which an ALK fusion protein (such as EML4-ALK or TFG-ALK) is expressed. These tumors are most likely to respond to inhibitors of the kinase activity of the mutant ALK protein, such as WHI-131 or WHI-154. The ability to identify, as early as possible, cancers that are driven by a mutant ALK kinase will greatly assist in clinically determining which therapeutic, or combination of therapeutics, will be most appropriate for a particular patient, thus helping to avoid prescription of inhibitors targeting other kinases that are not, in fact, the primary signaling molecule driving the cancer.

Accordingly, the invention provides, in part, methods for detecting the presence of an ALK mutant polynucleotide and/or fusion polypeptide in a cancer using fusion-specific and mutant-specific reagents of the invention. Such methods may be practiced, for example, to identify a solid tumor, such as NSCLC, that is likely to respond to an inhibitor of the ALK kinase activity of the mutant protein. The invention also provides, in part, methods for determining whether a compound inhibits the progression of a cancer characterized by an EML4-ALK fusion polypeptide. Further provided by the invention is a method for inhibiting the progression of a solid tumor that expresses an EML4-ALK fusion polypeptide or a TFG-ALK fusion polypeptide by inhibiting the expression and/or activity of the mutant polypeptide. Such methods are described in further detail below.

The further aspects, advantages, and embodiments of the invention are described in more detail below. All references cited herein are hereby incorporated by reference in their entirety.

DEFINITIONS

As used herein, the following terms have the meanings indicated.

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "humanized antibody", as used herein, refers to antibody molecules in which amino acids have been replaced in the non-antigen binding regions in order to more closely resemble a human antibody, while still retaining the original binding ability.

The term "biologically active" refers to a protein having structural, regulatory, or biochemical functions of a naturally occurring molecule. Likewise, "immunologically active" refers to the capability of the natural, recombinant, or synthetic EML4-ALK or TFG-ALK fusion polypeptide, or any oligopeptide thereof, to induce a specific immune response in appropriate animals or cells and to bind with specific antibodies.

The term "biological sample" is used in its broadest sense, and means any biological sample suspected of containing ALK fusion polynucleotides or polypeptides or fragments thereof (including EML4-ALK and TFG-ALK fusion polynucleotides and polypeptides), and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells, blood, urine, marrow, or a tissue, and the like.

"Characterized by" with respect to a cancer and mutant ALK polynucleotide and polypeptide is meant a cancer in which a gene deletion or translocation and/or expressed fusion polypeptide involving ALK are present as compared to a cancer in which such gene deletion and/or fusion polypeptide are not present. The presence of mutant polypeptide may drive, in whole or in part, the growth and survival of such cancer.

"Consensus" refers to a nucleic acid sequence which has been re-sequenced to resolve uncalled bases, or which has been extended using XL-PCR™ (Perkin Elmer, Norwalk, Conn.) in the 5' and/or the 3' direction and re-sequenced, or which has been assembled from the overlapping sequences of more than one Incyte clone using the GELVIEW™ Fragment Assembly system (GCG, Madison, Wis.), or which has been both extended and assembled.

"ALK kinase-inhibiting therapeutic" means any composition comprising one or more compounds, chemical or biological, which inhibits, either directly or indirectly, the expression and/or activity of wild type or truncated ALK kinase, either alone and/or as part of a fusion protein (such as EML4-ALK fusion proteins and TFG-ALK fusion protein).

"Derivative" refers to the chemical modification of a nucleic acid sequence encoding a disclosed fusion polynucleotide or the encoded polypeptide itself. Illustrative of such modifications would be replacement of hydrogen by an alkyl, acyl, or amino group. A nucleic acid derivative would encode a polypeptide that retains essential biological characteristics of the natural molecule.

"Detectable label" with respect to a polypeptide, polynucleotide, or reagent disclosed herein means a chemical, biological, or other modification, including but not limited to fluorescence, mass, residue, dye, radioisotope, label, or tag modifications, etc., by which the presence of the molecule of interest may be detected.

"Expression" or "expressed" with respect to an ALK fusion polypeptide in a biological sample means significantly expressed as compared to control sample in which this fusion polypeptide is not significantly expressed.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below. The term "specifically detects" with respect to such an AQUA peptide means the peptide will only detect and quantify polypeptides and proteins that contain the AQUA peptide sequence and will not substantially detect polypeptides and proteins that do not contain the AQUA peptide sequence.

"Isolated" (or "substantially purified") refers to nucleic or amino acid sequences that are removed from their natural environment, isolated or separated. They preferably are at least 60% free, more preferably 75% free, and most preferably 90% or more free from other components with which they are naturally associated.

"Mimetic" refers to a molecule, the structure of which is developed from knowledge of the structure of an ALK fusion polypeptide or portions thereof and, as such, is able to effect some or all of the actions of translocation associated protein-like molecules.

"Mutant ALK" or "fusion" polynucleotide or polypeptide means a fusion polynucleotide or polypeptide involving ALK and a secondary protein (e.g. EML-4 or TFG), as described herein.

"Polynucleotide" (or "nucleotide sequence") refers to an oligonucleotide, nucleotide, or polynucleotide, and fragments or portions thereof, and to DNA or RNA of genomic or synthetic origin, which may be single- or double-stranded, and represent the sense or anti-sense strand.

"Polypeptide" (or "amino acid sequence") refers to an oligopeptide, peptide, polypeptide, or protein sequence, and fragments or portions thereof, and to naturally occurring or synthetic molecules. Where "amino acid sequence" is recited herein to refer to an amino acid sequence of a naturally occurring protein molecule, "amino acid sequence" and like terms, such as "polypeptide" or "protein", are not meant to limit the amino acid sequence to the complete, native amino acid sequence associated with the recited protein molecule.

"EML4-ALK fusion polynucleotide" refers to the nucleic acid sequence of a substantially purified EML4-ALK deletion mutant gene product or fusion polynucleotide (short or long variant) as described herein, obtained from any species, particularly mammalian, including bovine, ovine, porcine, murine, equine, and preferably human, from any source whether natural, synthetic, semi-synthetic, or recombinant.

"EML4-ALK fusion polypeptide" refers to the amino acid sequence of a substantially purified EML4-ALK fusion polypeptide (short or long variant) described herein, obtained from any species, particularly mammalian, including bovine, ovine, porcine, murine, equine, and preferably human, from any source whether natural, synthetic, semi-synthetic, or recombinant.

"TFG-ALK fusion polynucleotide" refers to the nucleic acid sequence of a substantially purified TFG-ALK translocation mutant gene product or fusion polynucleotide as described herein, obtained from any species, particularly mammalian, including bovine, ovine, porcine, murine, equine, and preferably human, from any source whether natural, synthetic, semi-synthetic, or recombinant.

"TFG-ALK fusion polypeptide" refers to the amino acid sequence of a substantially purified TFG-ALK fusion polypeptide described herein, obtained from any species, particularly mammalian, including bovine, ovine, porcine, murine, equine, and preferably human, from any source whether natural, synthetic, semi-synthetic, or recombinant.

The terms "specifically binds to" (or "specifically binding" or "specific binding") in reference to the interaction of an antibody and a protein or peptide, mean that the interaction is dependent upon the presence of a particular structure (i.e. the antigenic determinant or epitope) on the protein; in other words, the antibody is recognizing and binding to a specific protein structure rather than to proteins in general. The term "does not bind" with respect to an antibody's binding to sequences or antigenic determinants other than that for which it is specific means does not substantially react with as compared to the antibody's binding to antigenic determinant or sequence for which the antibody is specific.

The term "stringent conditions" with respect to sequence or probe hybridization conditions is the "stringency" that occurs within a range from about $T_m$ minus 5° C. (5° C. below the melting temperature ($T_m$) of the probe or sequence) to about 20° C. to 25° C. below $T_m$. Typical stringent conditions are: overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences.

A "variant" of a mutant ALK polypeptide refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A. Identification of Mutant ALK Kinases in Human Solid Tumors.

Figure 1B:
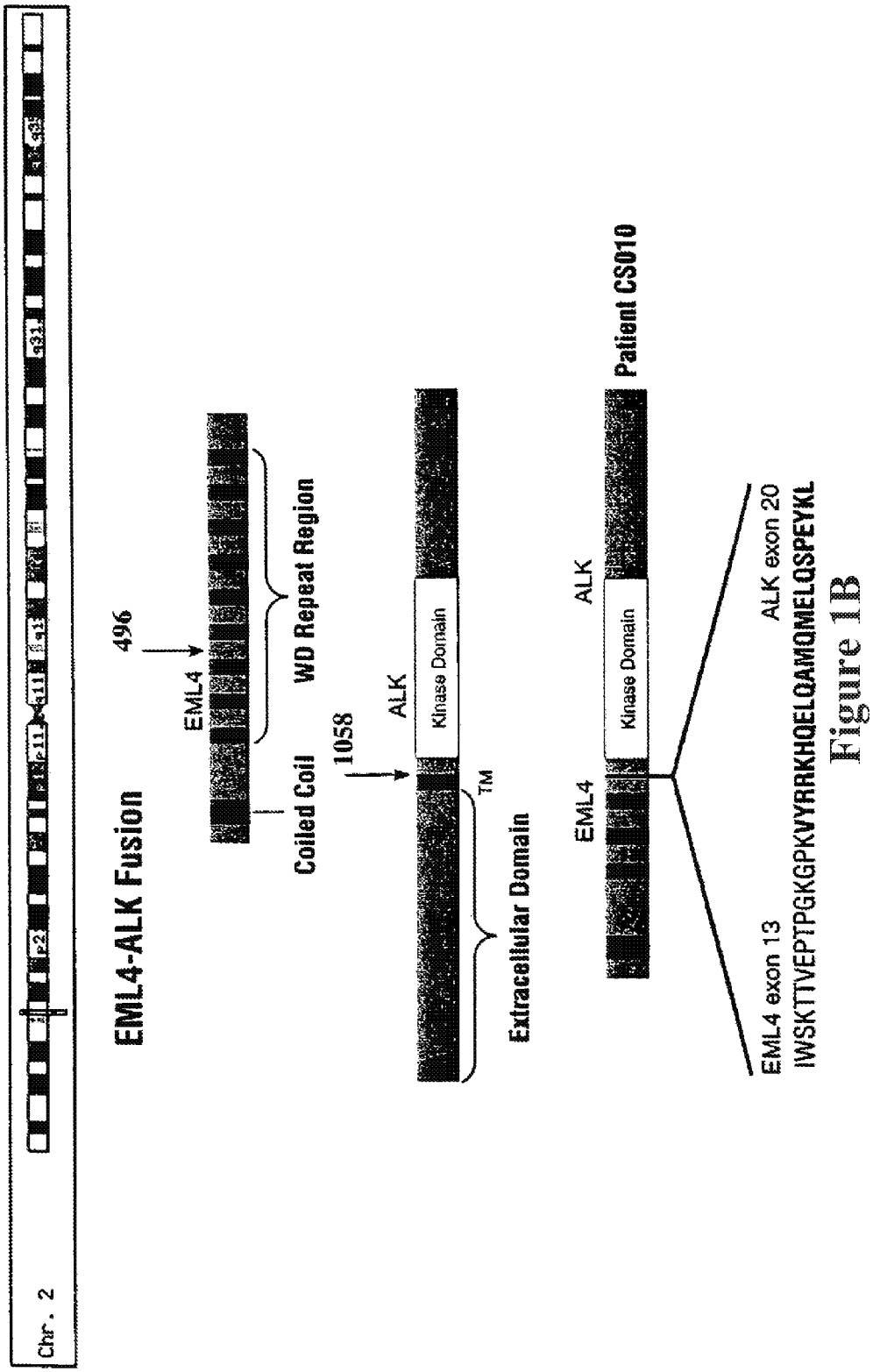
FIG. 1B—shows the locations of the EML-4 gene and ALK gene on chromosome 2 (panel A), and the domain locations of full-length EML-4 and ALK proteins as well as those of EML4-ALK fusion protein (long variant) (panel B); the fusion junction occurs at amino acids 495-496, and the fusion protein includes the kinase domain (but not the transmembrane and extracellular domains) of ALK. Also shown (in panel B) the DNA (and protein) sequence of the EML4 exon 13/ALK exon 20 fusion junction region (SEQ ID NO: 24 and SEQ ID NO: 25, respectively).

The novel human gene deletions disclosed herein, which occurs on chromosome 2 and result in expression of two fusion protein variants that combine the N-terminus of EML-4 with the kinase domain and C-terminus of ALK, were surprisingly identified during examination of global phosphorylated peptide profiles in extracts from non-small cell lung carcinoma (NSCLC) cell lines (including H2228) and solid tumors from patients. NSCLC, a solid tumor, is a subtype of lung cancer. The proteins involved in these deletion fusions are shown in FIGS. 1A-1B, panel A.

The phosphorylation profile of the H2228 cell line was first elucidated using a recently described technique for the isolation and mass spectrometric characterization of modified peptides from complex mixtures (see U.S. Patent Publication No. 20030044848, Rush et al., "Immunoaffinity Isolation of Modified Peptides from Complex Mixtures" (the "IAP" technique), as further described in Example 1 below. Application of the IAP technique using a phosphotyrosine-specific antibody (CELL SIGNAUNG TECHNOLOGY, INC., Beverly, Mass., 2003/04 Cat. #9411), identified that the H2228 cell line expresses ALK kinase, but that the protein was apparently truncated. The screen identified many other activated kinases in the cell line, including some that are known to be activated in lung cancer. Analysis of the sequence 5' to ALK by 5' RACE then identified that the kinase was fused to the N-terminus of EML-4 (see FIG. 6).

Subsequent examination of 154 tumor samples from NSCLC patients using the same global phospho-profiling approach not only confirmed the presence of the EML4-ALK (short variant) mutation in a population of those patients, but also revealed the presence of a second EML4-ALK (long variant) and the presence of the TFG-ALK mutation in other patient populations (see Example 1B and 1C).

Confirmation that the mutant ALK proteins are driving cell proliferation and survival in these NSCLC tumors may be established by inhibiting the cells using siRNA silencing (see Example 3).

The EML4-ALK fusion genes (short and long variants) and the TFG-ALK fusion gene were amplified by PCR, isolated, and sequenced (see Example 3). As shown in panel B of FIGS. 1A-1B, the EML4-ALK deletion combines the N-terminus of wild type EML-4 (either amino acids 1-233 in the short variant, or amino acids 1-495 in the long variant) with the kinase domain and C-terminus of wild type ALK (amino acids 1057-1620) (see also SEQ ID NOs: 3 and 5). The fusion junction occurs just C-terminus to the transmembrane domain of wild type ALK (see FIGS. 1A-1B). The EML4-ALK fusion polypeptides retain the N-terminal 233 or 495 amino acids of EML-4, respectively, which includes the coiled coil domain of this protein. The resulting EML4-ALK fusion proteins, which comprise 796 amino acids (short variant) or 1059 amino acids (long variant), respectively (see panel B of FIGS. 1A-1B and FIGS. 2A-2B (SEQ ID NOs: 1 and 18)), retain kinase activity of ALK. The exons involved and the fusion junction are shown in FIGS. 1A-1B (panel B). The fusion junction includes intron 6 from EML-4, which follows exon 6 (short variant) or exon 13 from EML-4 (long variant).

Figure 1C:
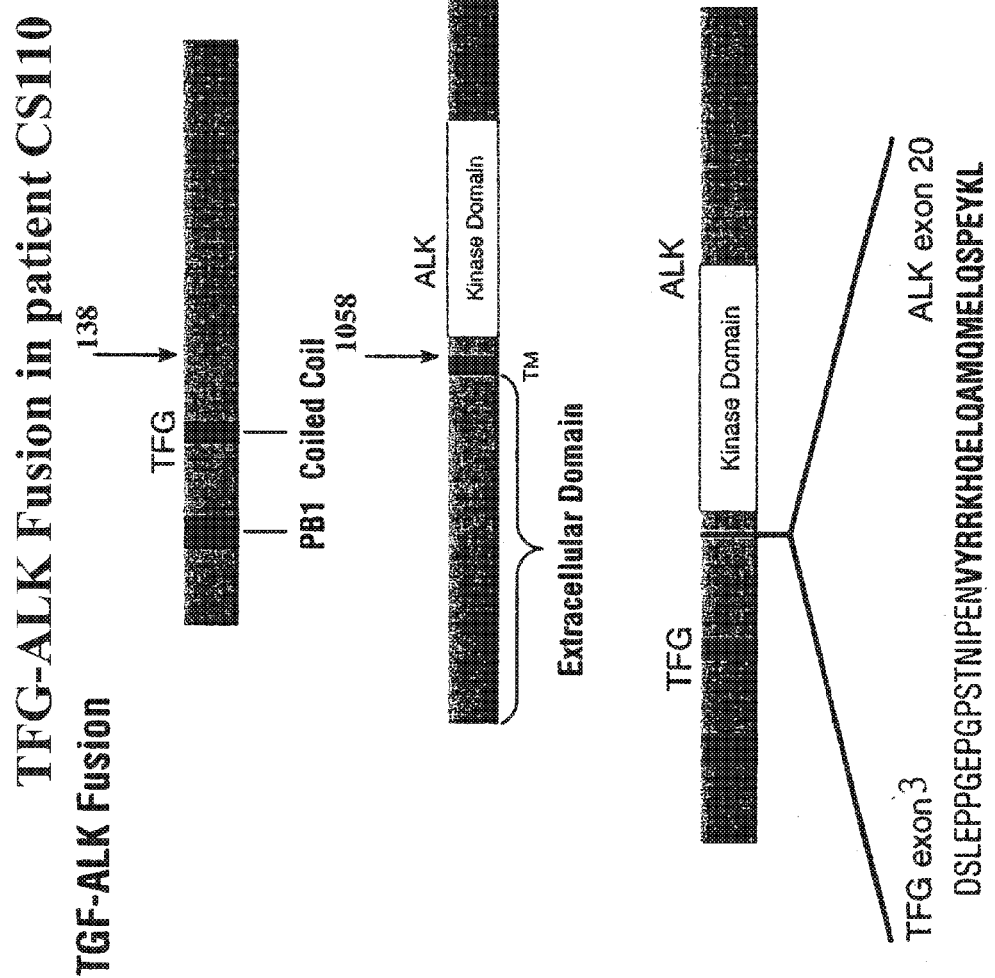
FIG. 1C—shows the locations of the TFG gene on chromosome 6 and ALK gene on chromosome 2 (panel A), and the domain locations of full-length TFG and ALK proteins as well as those of TFG-ALK fusion protein (panel B); the fusion junction occurs at amino acids 138-139, and the fusion protein includes the kinase domain (but not the transmembrane and extracellular domains) of ALK. Also shown (in panel B) the DNA (and protein) sequence of the TFG exon 3/ALK exon 20 fusion junction region (SEQ ID NO: 26 and SEQ ID NO: 27, respectively).

As shown in panel B of FIG. 1C, the TFG-ALK translocation combines the N-terminus of wild type TFG (amino acids 1-138) with the kinase domain and C-terminus of wild type ALK (amino acids 1057-1620) (see also SEQ ID NOs: 22 and 5; and panel B of FIG. 1C and FIG. 4C (SEQ ID NOs: 20 and 1)). The fusion junction occurs just C-terminus to the transmembrane domain of wild type ALK (see FIG. 1C) and retains kinase activity of ALK. The exons involved and the fusion junction are shown in FIG. 1C (panel B). The fusion junction includes exon 3 from TFG and exon 20 from ALK.

FISH probes were used to detect the presence of the EML4-ALK (short variant) fusion protein in a group of 400 paraffin-embedded human NSCLC tumor samples (see Examples 6 and 7; FIG. 6). The incidence of this short variant mutation in this sample size was very low. However, expression of the EML4-ALK fusion proteins (both short and long variants), as well as the TFG-ALK fusion protein, was detected in higher incidence using the LAP technique to examine global phosphorylation profiles in another group of 154 frozen human NSCLC tumor samples from patients (see Example 1B).

B. Isolated Polynucleotides.

The present invention provides, in part, isolated polynucleotides that encode EML4-ALK fusion polypeptides, nucleotide probes that hybridize to such polynucleotides, and methods, vectors, and host cells for utilizing such polynucleotides to produce recombinant fusion polypeptides.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were determined using an automated peptide sequencer (see Example 2). As is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each nucleotide sequence set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO: 2 set forth using deoxyribonucleotide abbreviations is intended to indicate an RNA molecule having a sequence in which each deoxyribonucleotide A, G or C of SEQ ID NO: 2 has been replaced by the corresponding ribonucleotide A, G or C, and each deoxyribonucleotide T has been replaced by a ribonucleotide U.

In one embodiment, the invention provides an isolated polynucleotide comprising a nucleotide sequence at least 95% identical to a sequence selected from the group consisting of:

(a) a nucleotide sequence encoding an Echinoderm Microtubule-Associated Protein-Like 4/Anaplastic Lymphoma Kinase (EML4-ALK) fusion polypeptide comprising the amino acid sequence of SEQ ID NO: 1 or SEQ ID NO: 18;

(b) a nucleotide sequence encoding an EML4-ALK fusion polypeptide, said nucleotide sequence comprising the nucleotide sequence of SEQ ID NO: 2 or SEQ ID NO: 19;

(c) a nucleotide sequence encoding an EML4-ALK fusion polypeptide comprising the N-terminal amino acid sequence of EML-4 (residues 1-222 of SEQ ID NO: 3 or residues 1-495 of SEQ ID NO: 3) and the kinase domain of ALK (residues 1116-1383 of SEQ ID NO: 5);

(d) a nucleotide sequence comprising the N-terminal nucleotide sequence of EML-4 (nucleotides 1-700 of SEQ ID NO: 4 or nucleotides 1-1486 of SEQ ID NO: 4) and the kinase domain nucleotide sequence of ALK (nucleotides 3348-4149 of SEQ ID NO: 6);

(e) a nucleotide sequence comprising at least six contiguous nucleotides encompassing the fusion junction (nucleotides 700-701 of SEQ ID NO: 2 or nucleotides 1486-1487 of SEQ ID NO: 19) of an EML4-ALK fusion polynucleotide;

(f) a nucleotide sequence encoding a polypeptide comprising at least six contiguous amino acids encompassing the fusion junction (residues 233-234 of SEQ ID NO: 1 or residues 495-496 of SEQ ID NO: 18) of an EML4-ALK fusion polypeptide; and (g) a nucleotide sequence complementary to any of the nucleotide sequences of (a)-(f).

Using the information provided herein, such as the nucleotide sequence in FIG. 2 (SEQ ID NO: 2), a nucleic acid molecule of the present invention encoding a mutant ALK polypeptide of the invention may be obtained using standard cloning and screening procedures, such as those for cloning cDNAs using mRNA as starting material. Illustrative of the invention, the EML4-ALK fusion polynucleotide (short variant) described in FIG. 2 (SEQ ID NO: 2) was isolated from genomic DNA from a human NSCLC cell line (as further described in Example 2 below). The fusion gene can also be identified in genomic DNA or cDNA libraries in other cancers, including solid tumors, in which a disclosed EML4-ALK gene deletion (chromosome 2) occurs.

The determined nucleotide sequences of the EML4-ALK fusion genes (SEQ ID NOs: 2 and 19) encode kinase fusion proteins of 796 amino acids (short variant) and 1059 amino acids (long variant), respectively (see FIGS. 2A-B (SEQ ID NOs: 1 and 18) and FIGS. 1A-B). The EML4-ALK fusion polynucleotides comprise the portion of the nucleotide sequence of wild type EML-4 (see FIG. 3 (SEQ ID NO: 4)) that encodes the N-terminus (amino acids 1-233 (short variant) or amino acids 1-495 (long variant)) of that protein with the portion of the nucleotide sequence of wild type ALK (see FIG. 4 (SEQ ID NO: 6)) that encodes the kinase domain and C-terminus of that protein. See FIGS. 1A-B. The kinase domain comprises residues 292-568 in the short variant fusion protein (encoded by nucleotides 874-1704 of the short variant fusion polynucleotide) or residues 555-831 in the long variant fusion protein (encoded by nucleotides 1663-2494 of the long variant fusion polynucleotide). See FIGS. 2A-2B.

As indicated, the present invention provides, in part, the mature form of the EML4-ALK fusion proteins. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide.

By the mature EML4-ALK polypeptide having the amino acid sequence encoded, e.g. by the deposited cDNA clone, is meant the mature form of this fusion protein produced by expression in a mammalian cell (e.g., 3T3 cells, as described below) of the complete open reading frame encoded by the human DNA sequence of the deposited clone or other done encoding mature fusion polypeptide.

As indicated, polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

Isolated polynucleotides of the invention are nucleic acid molecules, DNA or RNA, which have been removed from their native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated polynucleotides of the invention include the DNA molecule shown in FIGS. 2A-B (SEQ ID NOs: 2 and 19), DNA molecules comprising the coding sequence for the mature EML4-ALK fusion proteins shown in FIGS. 1A-B (SEQ ID NOs: 1 and 18), and DNA molecules that comprise a sequence substantially different from those described above but which, due to the degeneracy of the genetic code, still encode a ALK mutant polypeptide of the invention. The genetic code is well known in the art, thus, it would be routine for one skilled in the art to generate such degenerate variants.

In another embodiment, the invention provides an isolated polynucleotide encoding the EML4-ALK fusion polypeptide comprising the EML4-ALK fusion nucleotide sequence contained in the above-described deposited cDNA clone. Preferably, such nucleic acid molecule will encode the mature fusion polypeptide encoded by the deposited cDNA clone or another clone expressing a full length EML4-ALK fusion protein described herein. In another embodiment, the invention provides an isolated nucleotide sequence encoding an EML4-ALK fusion polypeptide comprising the N-terminal amino acid sequence of EML-4 (residues 1-222 of SEQ ID NO: 3 or residues 1-495 of SEQ ID NO: 3) and the kinase domain of ALK (residues 1116-1383 of SEQ ID NO: 5). In one embodiment, the polypeptide comprising the kinase domain of ALK comprises residues 1057-1620 of SEQ ID NO: 5 (see FIG. 1, panel B). In another embodiment, the aforementioned N-terminal amino acid sequence of EML-4 and kinase domain of ALK are encoded by nucleotide sequences comprising nucleotides 1-666 of SEQ ID NO: 4 or nucleotides 1-1486 of SEQ ID NO: 4 and nucleotides 3171-4860 of SEQ ID NO: 6, respectively.

The invention further provides isolated polynucleotides comprising nucleotide sequences having a sequence complementary to one of the mutant ALK polynucleotides of the invention. Such isolated molecules, particularly DNA molecules, are useful as probes for gene mapping, by in situ hybridization with chromosomes, and for detecting expression of a EML4-ALK fusion protein in human tissue, for instance, by Northern blot analysis, as further described in Section F below.

The present invention is further directed to fragments of the isolated nucleic acid molecules described herein. By a fragment of an isolated EML4-ALK polynucleotide of the invention is intended fragments at least about 15 nucleotides, and more preferably at least about 20 nucleotides, still more preferably at least about 30 nucleotides, and even more preferably, at least about 40 nucleotides in length, which are useful as diagnostic probes and primers as discussed herein. Of course, larger fragments of about 50-1500 nucleotides in length are also useful according to the present invention, as are fragments corresponding to most, if not all, of the mutant ALK nucleotide sequences of the deposited cDNAs or as shown in FIG. 2 (SEQ ID NO: 2) or other done expressing the a fusion polynucleotide as shown in FIGS. 2A-B (SEQ ID NOs: 2 or 19). By a fragment at least 20 nucleotides in length, for example, is intended fragments that include 20 or more contiguous bases from the respective nucleotide sequences from which the fragments are derived. Generation of such DNA fragments is routine to the skilled artisan, and may be accomplished, by way of example, by restriction endonuclease cleavage or shearing by sonication of DNA obtainable from the deposited cDNA clone or synthesized according to the sequence disclosed herein. Alternatively, such fragments can be directly generated synthetically.

Preferred nucleic acid fragments or probes of the present invention include nucleic acid molecules encoding the fusion junction of the EML4-ALK fusion gene products (see FIGS. 1A-B, panel B). For example, in certain preferred embodiments, an isolated polynucleotide of the invention comprises a nucleotide sequence/fragment comprising at least six contiguous nucleotides encompassing the fusion junction (nucleotides 700-701 of SEQ ID NO: 2 or nucleotides 1486-1487 of SEQ ID NO: 19) of an EML4-ALK fusion polynucleotide (see FIGS. 1A-B, panel B (SEQ ID NOs: 8 and 25)). In another preferred embodiment, an isolated polynucleotide of the invention comprises a nucleotide sequence/fragment that encodes a polypeptide comprising at least six contiguous amino adds encompassing the fusion junction (residues 233-234 of SEQ ID NO: 1 or residues 495-496 of SEQ ID NO: 18) of an EML4-ALK fusion polypeptide (see FIGS. 1A-B, bottom panel (SEQ ID NOs: 7 and 24)).

In another aspect, the invention provides an isolated polynucleotide that hybridizes under stringent hybridization conditions to a portion of a mutant ALK polynucleotide of the invention as described herein. By "stringent hybridization conditions" is intended overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C.

By a polynucleotide that hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

Of course, polynucleotides hybridizing to a larger portion of the reference polynucleotide (e.g. the mature EML4-ALK fusion polynucleotide described in FIG. 2 (SEQ ID NO: 2)), for instance, a portion 50-750 nt in length, or even to the entire length of the reference polynucleotide, are also useful as probes according to the present invention, as are polynucleotides corresponding to most, if not all, of the nucleotide sequences of the deposited cDNAs or the nucleotide sequences shown in FIGS. 2A-B (SEQ ID NOs: 2 or 19), or FIGS. 1A-B (panel B)) (SEQ ID NOs: 7 and 24).

By a portion of a polynucleotide of "at least 20 nucleotides in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in MOLECULAR CLONING, A LABORATORY MANUAL, $2^{nd}$ Ed., Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference. Of course, a polynucleotide which hybridizes only to a poly A sequence (such as the 3' terminal poly(A) tract of the EML4-ALK sequence shown in FIG. 2 (SEQ ID NO: 2)) or to a complementary stretch of T (or U) resides, would not be included in a polynucleotide of the invention used to hybridize to a portion of a nucleic acid of the invention, since such a polynucleotide would hybridize to any nucleic add molecule containing a poly (A) stretch or the complement thereof (e.g., practically any double-stranded cDNA clone).

As indicated, nucleic acid molecules of the present invention, which encode a mutant ALK polypeptide of the invention, may include but are not limited to those encoding the amino acid sequence of the mature polypeptide, by itself; the coding sequence for the mature polypeptide and additional sequences, such as those encoding the leader or secretory sequence, such as a pre-, or pro- or pre-pro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide that facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include a EML4-ALK fusion polypeptide itself fused to Fc at the N- or C-terminus.

The present invention further relates to variants of the nucleic acid molecules of the present invention, which encode portions, analogs or derivatives of an EML4-ALK fusion polypeptide disclosed herein. Variants may occur naturally, such as a natural allelic variant. By an "allelic variant" is intended one of several alternate forms of a gene occupying a given locus on a chromosome of an organism. See, e.g. GENES II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities (e.g. kinase activity) of the mutant ALK polypeptides disclosed herein. Also especially preferred in this regard are conservative substitutions.

Further embodiments of the invention include isolated polynucleotides comprising a nucleotide sequence at least 90% identical, and more preferably at least 95%, 96%, 97%, 98% or 99% identical, to a mutant ALK polynucleotide of the invention (for example, a nucleotide sequence encoding the EML4-ALK fusion polypeptide having the complete amino acid sequence shown in FIG. 2 (SEQ ID NO: 1; or a nucleotide sequence encoding the N-terminal of EML-4 and the kinase domain of ALK (see FIG. 1, panel B; and FIGS. 3 and 4); or a nucleotide complementary to such exemplary sequences).

By a polynucleotide having a nucleotide sequence at least, for example, 95% "identical" to a reference nucleotide sequence encoding a mutant ALK polypeptide is intended that the nucleotide sequence of the polynucleotide is identical to the reference sequence except that the polynucleotide sequence may include up to five point mutations per each 100 nucleotides of the reference nucleotide sequence encoding the mutant ALK polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequences shown in FIGS. 2A-B (SEQ ID NOs: 2 and 19) or to the nucleotide sequence of the deposited cDNA clones described above can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference EML4-ALK fusion polynucleotide sequence or truncated ALK polynucleotide sequence according to the present invention, the parameters are set, of course, such that the percentage of identity is calculated over the full length of the reference nucleotide sequence and that gaps in homology of up to 5% of the total number of nucleotides in the reference sequence are allowed.

The present invention includes in its scope nucleic acid molecules at least 90%, 95%, 96%, 97%, 98% or 99% identical to the nucleic acid sequence shown in FIG. 2 (SEQ ID NO: 2), or to the nucleic acid sequences of the deposited cDNAs, irrespective of whether they encode a polypeptide having ALK kinase activity. This is because even where a particular nucleic acid molecule does not encode a fusion polypeptide having ALK kinase activity, one of skill in the art would still know how to use the nucleic acid molecule, for instance, as a hybridization probe or a polymerase chain reaction (PCR) primer. Uses of the nucleic acid molecules of the present invention that do not encode a polypeptide having kinase include, inter alia, (1) isolating the EML4-ALK deletion gene, or truncated ALK gene, or allelic variants thereof in a cDNA library; (2) in situ hybridization (e.g., "FISH") to metaphase chromosomal spreads to provide precise chromosomal location of the EML4-ALK deletion gene or truncated ALK gene, as described in Verma et al., HUMAN CHROMOSOMES: A MANUAL OF BASIC TECHNIQUES, Pergamon Press, New York (1988); and Northern Blot analysis for detecting EML4-ALK fusion protein or truncated ALK kinase mRNA expression in specific tissues.

Preferred, however, are nucleic acid molecules having sequences at least 95% identical to a mutant ALK polypeptide of the invention or to the nucleic acid sequence of the deposited cDNAs that do, in fact, encode a fusion polypeptide having ALK kinase activity. Such activity may be similar, but not necessarily identical, to the activity of an EML4-ALK fusion protein disclosed herein (either the full-length protein, the mature protein, or a protein fragment that retains kinase activity), as measured in a particular biological assay. For example, the kinase activity of ALK can be examined by determining its ability to phosphorylate one or more tyrosine containing peptide substrates, for example, Insulin Receptor Substrate 1 or 2 (IRS1, IRS2), which are substrates for the ALK kinase.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNAs or the nucleic acid sequences shown in FIGS. 2A-B (SEQ ID NOs: 2 and 19) will encode a mutant polypeptide having ALK activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide that retains ALK kinase activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie et al., "Deciphering the Message in Protein Sequences: Tolerance to Amino Acid Substitutions," *Science* 247: 1306-1310 (1990), which describes two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. These studies have revealed that proteins are surprisingly tolerant of amino acid substitutions. Skilled artisans familiar with such techniques also appreciate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra., and the references cited therein.

Methods for DNA sequencing that are well known and generally available in the art may be used to practice any polynucleotide embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

Polynucleotide sequences encoding a mutant ALK polypeptide of the invention may be extended utilizing a partial nucleotide sequence and employing various methods known in the art to detect upstream sequences such as promoters and regulatory elements. For example, one method that may be employed, "restriction-site" PCR, uses universal primers to retrieve unknown sequence adjacent to a known locus (Sarkar, G., *PCR Methods Applic.* 2: 318-322 (1993)). In particular, genomic DNA is first amplified in the presence of primer to linker sequence and a primer specific to the known region. Exemplary primers are those described in Example 2 herein. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al., *Nucleic Acids Res.* 16: 8186 (1988)). The primers may be designed using OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al., *PCR Methods Applic.* 1: 111-119 (1991)). In this method, multiple restriction enzyme digestions and ligations may also be used to place an engineered double-stranded sequence into an unknown portion of the DNA molecule before performing PCR. Another method which may be used to retrieve unknown sequences is that described in Parker et al., *Nucleic Acids Res.* 19: 3055-3060 (1991)). Additionally, one may use PCR, nested primers, and PROMOTERFINDER® libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems, which are commercially available, may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA that might be present in limited amounts in a particular sample.

C. Vectors and Host Cells.

The present invention also provides recombinant vectors that comprise an isolated polynucleotide of the present invention, host cells which are genetically engineered with the recombinant vectors, and the production of recombinant EML4-ALK polypeptides or fragments thereof by recombinant techniques.

Recombinant constructs may be introduced into host cells using well-known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host. In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert comprising an EML4-ALK polynucleotide or of the invention should be operatively linked to an appropriate promoter, such as the phage lambda PL promoter, the *E. coli* lac, trp and tac promoters, the SV40 early and late promoters and promoters of retroviral LTRs, to name a few. Other suitable promoters are known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia.

Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast, *Saccharomyces cerevisiae*, a number of vectors containing constitutive or inducible promoters such as alpha factor, alcohol oxidase, and PGH may be used. For reviews, see Ausubel et al. (1989) CURRENT PROTOCOLS IN MOLECULAR BIOLOGY, John Wiley & Sons, New York, N.Y., and Grant et al., *Methods Enzymol.* 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY (1986).

Transcription of DNA encoding an EML4-ALK fusion polypeptide of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at basepairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein (e.g. a GST-fusion), and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins.

EML4-ALK fusion polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Accordingly, in one embodiment, the invention provides a method for producing a recombinant EML4-ALK fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art. See, e.g., CURRENT PROTOCOLS IN MOLECULAR BIOLOGY, Ausubel F M et al., eds., Volume 2, Chapter 16, Wiley Interscience.

D. Isolated Polypeptides.

The invention also provides, in part, isolated mutant ALK kinase polypeptides and fragments thereof. In one embodiment, the invention provides an isolated polypeptide comprising an amino acid sequence at least 95% identical to a sequence selected from the group consisting of:

(a) an amino acid sequence encoding an EML4-ALK fusion polypeptide comprising the amino acid sequence of SEQ ID NO: 1 or SEQ ID NO: 18;

(b) an amino acid sequence encoding an EML4-ALK fusion polypeptide comprising the N-terminal amino acid sequence of EML-4 (residues 1-222 of SEQ ID NO: 3 or residues 1-495 of SEQ ID NO: 3) and the kinase domain of ALK (residues 1116-1383 of SEQ ID NO: 5); and (c) an amino acid sequence encoding a polypeptide comprising at least six contiguous amino acids encompassing the fusion junction (residues 233-234 of SEQ ID NO: 1 or residues 495-496 of SEQ ID NO: 18) of an EML4-ALK fusion polypeptide.

In one preferred embodiment, recombinant mutant ALK polypeptides of the invention are provided, which may be produced using a recombinant vector or recombinant host cell as described above.

It will be recognized in the art that some amino acid sequences of an EML4-ALK fusion polypeptide or truncated active ALK kinase polypeptide can be varied without significant effect of the structure or function of the mutant protein. If such differences in sequence are contemplated, it should be remembered that there will be critical areas on the protein which determine activity (e.g. the kinase domain of ALK). In general, it is possible to replace residues that form the tertiary structure, provided that residues performing a similar function are used. In other instances, the type of residue may be completely unimportant if the alteration occurs at a non-critical region of the protein.

Thus, the invention further includes variations of an EML4-ALK fusion polypeptide that retain substantial ALK kinase activity or that include other regions of EML-4 or ALK proteins, such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Examples of conservative amino acid substitutions known to those skilled in the art are: Aromatic: phenylalanine tryptophan tyrosine; Hydrophobic: leucine isoleucine valine; Polar: glutamine asparagines; Basic: arginine lysine histidine; Acidic: aspartic acid glutamic acid; Small: alanine serine threonine methionine glycine. As indicated in detail above, further guidance concerning which amino acid changes are likely to be phenotypically silent (i.e., are not likely to have a significant deleterious effect on a function) can be found in Bowie et al., Science 247, supra.

The polypeptides of the present invention are preferably provided in an isolated form, and preferably are substantially purified. A recombinantly produced version of an EML4-ALK fusion polypeptide of the invention can be substantially purified by the one-step method described in Smith and Johnson, Gene 67: 31-40 (1988).

The polypeptides of the present invention include the EML4-ALK fusion polypeptides of FIGS. 2A-B (SEQ ID NOs: 1 and 18) (whether or not including a leader sequence), an amino acid sequence encoding an EML4-ALK fusion polypeptide comprising the N-terminal amino acid sequence of EML-4 (residues 1-222 of SEQ ID NO: 3 or residues 1-495 of SEQ ID NO: 3) and the kinase domain of ALK (residues 1116-1383 of SEQ ID NO: 5), and an amino acid sequence encoding a polypeptide comprising at least six contiguous amino acids encompassing the fusion junction (residues 233-234 of SEQ ID NO: 1 or residues 495-496 of SEQ ID NO: 18) of an EML4-ALK fusion polypeptide (see also FIGS. 1A-B, bottom panel), as well as polypeptides that have at least 90% similarity, preferably at least 95% similarity, and still more preferably at least 96%, 97%, 98% or 99% similarity to those described above.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482-489 (1981)) to find the best segment of similarity between two sequences.

By a polypeptide having an amino acid sequence at least, for example, 95% "identical" to a reference amino acid sequence of an EML4-ALK fusion polypeptide of the invention is intended that the amino acid sequence of the polypeptide is identical to the reference sequence except that the polypeptide sequence may include up to five amino acid alterations per each 100 amino acids of the reference amino acid sequence of the mutant ALK polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

An EML4-ALK fusion polypeptide of the present invention may be used as a molecular weight marker on SDS-PAGE gels or on molecular sieve gel filtration columns, for example, using methods well known to those of skill in the art.

As further described in detail below, the polypeptides of the present invention can also be used to generate fusion polypeptide specific reagents, such as polyclonal and monoclonal antibodies, or truncated polypeptide specific reagents, which are useful in assays for detecting mutant ALK polypeptide expression as described below, or as agonists and antagonists capable of enhancing or inhibiting the function/activity of the mutant ALK protein. Further, such polypeptides can be used in the yeast two-hybrid system to "capture" EML4-ALK fusion polypeptide or truncated ALK kinase polypeptide binding proteins, which are also candidate agonist and antagonist according to the present invention. The yeast two hybrid system is described in Fields and Song, *Nature* 340: 245-246 (1989).

In another aspect, the invention provides a peptide or polypeptide comprising an epitope-bearing portion of a polypeptide of the invention, for example, an epitope comprising the fusion junction of an EML4-ALK fusion polypeptide (see FIGS. 1A-B, bottom panel). The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Aced. Sci. USA* 81:3998-4002 (1983). The production of fusion polypeptide-specific antibodies of the invention is described in further detail below.

The antibodies raised by antigenic epitope-bearing peptides or polypeptides are useful to detect a mimicked protein, and antibodies to different peptides may be used for tracking the fate of various regions of a protein precursor that undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37: 767-778 (1984) at 777. The anti-peptide antibodies of the invention also are useful for purification of the mimicked protein, for instance, by adsorption chromatography using methods well known in the art. Immunological assay formats are described in further detail below.

Recombinant mutant ALK polypeptides are also within the scope of the present invention, and may be producing using polynucleotides of the invention, as described in Section B above. For example, the invention provides, in part, a method for producing a recombinant EML4-ALK fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art.

E. Mutant-Specific Reagents

Mutant ALK polypeptide-specific reagents useful in the practice of the disclosed methods include, among others, fusion polypeptide specific antibodies and AQUA peptides (heavy-isotope labeled peptides) corresponding to, and suitable for detection and quantification of, EML4-ALK fusion polypeptide expression in a biological sample from a cancer, such as a mammalian solid sarcoma or carcinoma tumor. Also useful are truncation-specific reagents, such as antibodies, AQUA peptides, or nucleic acid probes, suitable for detecting the presence or absence of a truncated ALK kinase polynucleotide or polypeptide of the invention. A fusion polypeptide-specific reagent is any reagent, biological or chemical, capable of specifically binding to, detecting and/or quantifying the presence/level of expressed EML4-ALK fusion polypeptide in a biological sample. The term includes, but is not limited to, the preferred antibody and AQUA peptide reagents discussed below, and equivalent reagents are within the scope of the present invention.

Antibodies.

Reagents suitable for use in practice of the methods of the invention include an EML4-ALK fusion polypeptide-specific antibody and a TFG-ALK fusion polypeptide-specific antibody. A fusion-specific antibody of the invention is an isolated antibody or antibodies that specifically bind(s) an EML4-ALK fusion polypeptide of the invention (e.g. SEQ ID NO: 1) but does not substantially bind either wild type EML-4 or wild type ALK, or specifically bind(s) a TFG-ALK fusion polypeptide described herein (e.g. SEQ ID NO: 20) but does not substantially bind either wild type TFG or wild type ALK. Other suitable reagents include epitope-specific antibodies that specifically bind to an epitope in the extracellular domain of wild type ALK protein sequence (which domain is not present in the truncated, active ALK kinase disclosed herein), and are therefore capable of detecting the presence (or absence) of wild type ALK in a sample.

Human EML4-ALK or TFG-ALK fusion polypeptide-specific antibodies may also bind to highly homologous and equivalent epitopic peptide sequences in other mammalian species, for example murine or rabbit, and vice versa. Antibodies useful in practicing the methods of the invention include (a) monoclonal antibodies, (b) purified polyclonal antibodies that specifically bind to the target polypeptide (e.g. the fusion junction of EML4-ALK fusion polypeptide (see FIGS. 1A-B, bottom panel) or TFG-ALK fusion polypeptide (see FIG. 1C, bottom panel), (c) antibodies as described in (a)-(b) above that bind equivalent and highly homologous epitopes or phosphorylation sites in other non-human species (e.g. mouse, rat), and (d) fragments of (a)-(c) above that bind to the antigen (or more preferably the epitope) bound by the exemplary antibodies disclosed herein.

The term "antibody" or "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et a., *Molec. Immunol.* 26: 403-11 (1989); Morrison et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et a.) The antibodies may also be chemically constructed specific antibodies made according to the method disclosed in U.S. Pat. No. 4,676,980 (Segel et al.)

The preferred epitopic site of an EML4-ALK fusion polypeptide specific antibody of the invention is a peptide fragment consisting essentially of about 11 to 17 amino acids of a human EML4-ALK fusion polypeptide sequence (SEQ ID NOs: 1 and 18) which fragment encompasses the fusion junction (which occurs at residues 233-234 in the short variant fusion protein and residues 495-496 in the long variant fusion protein (see FIGS. 1A-B (bottom panel)). It will be appreciated that antibodies that specifically binding shorter or longer peptides/epitopes encompassing the fusion junction of an EML4-ALK fusion polypeptide are within the scope of the present invention.

Similarly, the preferred epitopic site of a TFG-ALK fusion polypeptide specific antibody useful in the practice of the disclosed methods is a peptide fragment consisting essentially of about 11 to 17 amino acids of the human TFG-ALK fusion polypeptide sequence (SEQ ID NO: 20), which fragment encompasses the fusion junction (which occurs at residues 137-138 (see FIG. 1C (bottom panel)).

The invention is not limited to use of antibodies, but includes equivalent molecules, such as protein binding domains or nucleic acid aptamers, which bind, in a fusion-protein or truncated-protein specific manner, to essentially the same epitope to which an EML4-ALK or TFG-ALK fusion polypeptide-specific antibody useful in the methods of the invention binds. See, e.g., Neuberger et al., *Nature* 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired fusion-protein specific epitope (e.g. the fusion junction of an ALK fusion protein described herein), collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czemik, *Methods In Enzymology,* 201: 264-283 (1991); Merrifield, J. Am. Chem. Soc. 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. *Nature* 265: 495-97 (1975); Kohler and Milstein, *Eur. J. Immunol.* 6:511 (1976); see also, CURRENT PROTOCOLS IN MOLECULAR BIOLOGY, Ausubel et al. Eds. (1989). Monoclonal antibodies so produced are highly specific, and improve the selectivity and specificity of assay methods provided by the invention. For example, a solution containing the appropriate antigen (e.g. a synthetic peptide comprising the fusion junction of EML4-ALK fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, K. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spire et al., *J. Immunol. Methods,* 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) that is a topological equivalent of the epitope (i.e., a "mimotope") that is complementary to a particular paratope (antigen binding site) of an antibody of interest. More generally, this method involves detecting or determining a sequence of monomers that is a topographical equivalent of a ligand that is complementary to the ligand binding site of a particular receptor of interest. Similarly, U.S. Pat. No. 5,480,971, Houghten et al. (1996) discloses linear $C_1$-C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and fusion protein specificity according to standard techniques. See, e.g. Czemik et al., *Methods in Enzymology,* 201: 264-283 (1991). For example, the antibodies may be screened against a peptide library by ELISA to ensure specificity for both the desired antigen and, if desired, for reactivity only with, e.g. an EML4-ALK fusion polypeptide of the invention and not with wild type EML-4 or wild type ALK. The antibodies may also be tested by Western blotting against cell preparations containing target protein to confirm reactivity with the only the desired target and to ensure no appreciable binding to other fusion proteins involving ALK. The production, screening, and use of fusion protein-specific antibodies is known to those of skill in the art, and has been described. See, e.g., U.S. Patent Publication No. 20050214301, Wetzel et al., Sep. 29, 2005.

Fusion polypeptide-specific antibodies useful in the methods of the invention may exhibit some limited cross-reactivity with similar fusion epitopes in other fusion proteins or with the epitopes in wild type EML-4, wild type TFG, and wild type ALK that form the fusion junction. This is not unexpected as most antibodies exhibit some degree of cross-reactivity, and anti-peptide antibodies will often cross-react with epitopes having high homology or identity to the immunizing peptide. See, e.g., Czemik, supra. Cross-reactivity with other fusion proteins is readily characterized by Western blotting alongside markers of known molecular weight. Amino acid sequences of cross-reacting proteins may be examined to identify sites highly homologous or identical to the EML4-ALK or TFG-ALK fusion polypeptide sequence to which the antibody binds. Undesirable cross-reactivity can be removed by negative selection using antibody purification on peptide columns (e.g. selecting out antibodies that bind either wild type EML-4 and/or wild type ALK).

EML4-ALK fusion polypeptide-specific antibodies of the invention (and TFG-ALK fusion polypeptide-specific antibodies) that are useful in practicing the methods disclosed herein are ideally specific for human fusion polypeptide, but are not limited only to binding the human species, per se. The invention includes the production and use of antibodies that also bind conserved and highly homologous or identical epitopes in other mammalian species (e.g. mouse, rat, monkey). Highly homologous or identical sequences in other species can readily be identified by standard sequence comparisons, such as using BLAST, with a human EML4-ALK fusion polypeptide sequence disclosed herein (SEQ ID NOs: 1 and 18) or a human TFG-ALK fusion polypeptide sequence disclosed herein (SEQ ID NO: 20).

Antibodies employed in the methods of the invention may be further characterized by, and validated for, use in a particular assay format, for example flow cytometry (FC), immunohistochemistry (IHC), and/or Immunocytochemistry (ICC). The use of ALK fusion polypeptide-specific antibodies in such methods is further described in Section F below. Antibodies may also be advantageously conjugated to fluorescent dyes (e.g. Alexa488, PE), or labels such as quantum dots, for use in multi-parametric analyses along with other signal transduction (phospho-AKT, phospho-Erk 1/2) and/or cell marker (cytokeratin) antibodies, as further described in Section F below.

In practicing the methods of the invention, the expression and/or activity of wild type EML-4, wild type TFG, and/or wild type ALK in a given biological sample may also be advantageously examined using antibodies (either phospho-specific or total) for these wild type proteins. For example, ALK total and phosphorylation-site specific antibodies are commercially available (see CELL SIGNALING TECHNOLOGY, INC., Beverly Mass., 2005/06 Catalogue, #'s 3341, 3342). Such antibodies may also be produced according to standard methods, as described above. The amino acid sequences of human EML-4, TFG, and ALK are published (see FIGS. 3A and 4A-4C, and referenced SwissProt Accession Nos.), as are the sequences of these proteins from other species.

Detection of wild type EML-4, TFG, and wild type ALK expression and/or activation, along with EML4-ALK and/or TFG-ALK fusion polypeptide expression, in a biological sample (e.g. a tumor sample) can provide information on whether the fusion protein alone is driving the tumor, or whether wild type ALK is also activated and driving the tumor. Such information is clinically useful in assessing whether targeting the fusion protein or the wild type protein(s), or both, or is likely to be most beneficial in inhibiting progression of the tumor, and in selecting an appropriate therapeutic or combination thereof. Antibodies specific for the wild type ALK kinase extracellular domain, which is not present in the truncated active ALK kinase disclosed herein, may be particularly useful for determining the presence/absence of the mutant ALK kinase.

It will be understood that more than one antibody may be used in the practice of the above-described methods. For example, one or more EML4-ALK fusion polypeptide-specific antibodies together with one or more antibodies specific for another kinase, receptor, or kinase substrate that is suspected of being, or potentially is, activated in a cancer in which EML4-ALK fusion polypeptide is expressed may be simultaneously employed to detect the activity of such other signaling molecules in a biological sample comprising cells from such cancer.

Those of skill in the art will appreciate that EML4-ALK fusion polypeptides of the present invention and the fusion junction epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331: 84-86 (1988)). Fusion proteins that have a disulfide-linked dimeric structure due to the IgG part can also be more efficient in binding and neutralizing other molecules than the monomeric EML4-ALK fusion polypeptide alone (Fountoulakis et al., *J Biochem* 270: 3958-3964 (1995)).

Heavy-Isotope Labeled Peptides (AQUA Peptides).

EML4-ALK or TFG-ALK fusion polypeptide-specific reagents useful in the practice of the disclosed methods may also comprise heavy-isotope labeled peptides suitable for the absolute quantification of expressed ALK fusion polypeptide or truncated ALK kinase polypeptide in a biological sample. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known sequence previously identified by the IAP-LC-MS/MS method within in a target protein. If the site is modified, one AQUA peptide incorporating the modified form of the particular residue within the site may be developed, and a second AQUA peptide incorporating the unmodified form of the residue developed. In this way, the two standards may be used to detect and quantify both the modified an unmodified forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and MS³ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or MS$^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

AQUA internal peptide standards (heavy-isotope labeled peptides) may desirably be produced, as described above, to detect any quantify any unique site (e.g. the fusion junction within a disclosed EML4-ALK fusion polypeptide) within a mutant ALK polypeptide of the invention. For example, an AQUA phosphopeptide may be prepared that corresponds to the fusion junction sequence of an EML4-ALK fusion polypeptide (see FIGS. 1A-B (bottom panel)) or that corresponds to the truncation point of either EML4, TFG, or ALK. Peptide standards for may be produced for the EML4-ALK or TFG-ALK fusion junction and such standards employed in the AQUA methodology to detect and quantify the fusion junction (i.e. the presence of EML4-ALK fusion polypeptide) in a biological sample.

For example, an exemplary AQUA peptide of the invention comprises the amino acid sequence INQVYR (see FIG. 1, bottom panel), which corresponds to the three amino acids immediately flanking each side of the fusion junction in EML4-ALK fusion polypeptide (see SEQ ID NO: 7). It will be appreciated that larger AQUA peptides comprising the fusion junction sequence (and additional residues downstream or upstream of it) may also be constructed. Similarly, a smaller AQUA peptide comprising less than all of the residues of such sequence (but still comprising the point of fusion junction itself) may alternatively be constructed. Such larger or shorter AQUA peptides are within the scope of the present invention, and the selection and production of preferred AQUA peptides may be carried out as described above (see Gygi et al, Gerber et al., supra.).

Nucleic Acid Probes.

Fusion-specific reagents provided by the invention also include nucleic acid probes and primers suitable for detection of an EML4-ALK polynucleotide or truncated ALK kinase polynucleotide, as described in detail in Section B above. Such probes desirable include, among others, breakpoint probes corresponding to both sides of the breakpoints in wild-type EML4 and/or wild-type ALK genes that produce the fusion. The specific use of such probes in assays such as fluorescence in-situ hybridization (FISH) or polymerase chain reaction (PCR) amplification is described in Section F below. Similar breakpoint probes may be prepared to detect the presence of TFG-ALK fusion polynucleotide (see FIG. 1C (SEQ ID NO: 21).

F. Diagnostic Applications & Assay Formats.

The methods of the invention may be carried out in a variety of different assay formats known to those of skill in the art.

Immunoassays.

Immunoassays useful in the practice of the methods of the invention may be homogenous immunoassays or heterogeneous immunoassays. In a homogeneous assay the immunological reaction usually involves a mutant ALK kinase polypeptide-specific reagent (e.g. an EML4-ALK fusion polypeptide-specific antibody), a labeled analyte, and the biological sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radio-isotopes, fluorescent dyes, enzymes, bacteriophages, coenzymes, and so forth. Semi-conductor nanocrystal labels, or "quantum dots", may also be advantageously employed, and their preparation and use has been well described. See generally, K. Barovsky, *Nanotech. Law & Bus.* 1(2): Article 14 (2004) and patents cited therein.

In a heterogeneous assay approach, the reagents are usually the biological sample, a mutant ALK kinase polypeptide-specific reagent (e.g., an EML4-ALK fusion-specific antibody), and suitable means for producing a detectable signal. Biological samples as further described below may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. EML4-ALK fusion polypeptide-specific monoclonal antibodies may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of EML4-ALK or TFG-ALK fusion polypeptide is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other ALK fusion polypeptide- or truncated ALK kinase polypeptide-binding reagents may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Cell-based assays, such flow cytometry (FC), immunohistochemistry (IHC), or immunofluorescence (IF) are particularly desirable in practicing the methods of the invention, since such assay formats are clinically-suitable, allow the detection of mutant ALK kinase polypeptide expression in vivo, and avoid the risk of artifact changes in activity resulting from manipulating cells obtained from, e.g. a tumor sample in order to obtain extracts. Accordingly, in some preferred embodiment, the methods of the invention are implemented in a flow-cytometry (FC), immuno-histochemistry (IHC), or immunofluorescence (IF) assay format.

Flow cytometry (FC) may be employed to determine the expression of mutant ALK kinase polypeptide in a mammalian tumor before, during, and after treatment with a drug targeted at inhibiting ALK kinase activity. For example, tumor cells from a bone marrow sample may be analyzed by flow cytometry for EML4-ALK or TFG-ALK fusion polypeptide expression and/or activation, as well as for markers identifying cancer cell types, etc., if so desired. Flow cytometry may be carried out according to standard methods. See, e.g. Chow et al., *Cytometry* (*Communications in Clinical Cytometry*) 46: 72-78 (2001). Briefly and by way of example, the following protocol for cytometric analysis may be employed: fixation of the cells with 2% paraformaldehyde for 10 minutes at 37° C. followed by permeabilization in 90% methanol for 30 minutes on ice. Cells may then be stained with the primary EML4-ALK or TFG-ALK fusion polypeptide-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed EML4-ALK or TFG-ALK fusion polypeptide in the tumor. Similar analysis after treatment of the tumor with an ALK-inhibiting therapeutic would reveal the responsiveness of an ALK fusion polypeptide-expressing tumor to the targeted inhibitor of ALK kinase.

Immunohistochemical (IHC) staining may be also employed to determine the expression and/or activation status of mutant ALK kinase polypeptide in a mammalian cancer (e.g. a solid tumor like NSCLC) before, during, and after treatment with a drug targeted at inhibiting ALK kinase activity. IHC may be carried out according to well-known techniques. See, e.g., ANTIBODIES: A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary anti-EML4-ALK or anti-TFG-ALK fusion polypeptide antibody and secondary antibody; and finally detecting using ABC avidin/biotin method according to manufacturer's instructions.

Immunofluorescence (IF) assays may be also employed to determine the expression and/or activation status of mutant ALK kinase polypeptide in a mammalian cancer before, during, and after treatment with a drug targeted at inhibiting ALK kinase activity. IF may be carried out according to well-known techniques. See, e.g., J. M. Polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody against EML4-ALK or TFG-ALK fusion polypeptide followed by a secondary antibody labeled with a fluorescent dye such as Alexa488 and analyzed with an epifluorescent microscope.

Antibodies employed in the above-described assays may be advantageously conjugated to fluorescent dyes (e.g. Alexa488, PE), or other labels, such as quantum dots, for use in multi-parametric analyses along with other signal transduction (e.g. EGFR, phospho-AKT, phospho-Erk 1/2) and/or cell marker (e.g. cytokeratin) antibodies.

A variety of other protocols, including enzyme-linked immunosorbent assay (ELISA), radio-immunoassay (RIA), and fluorescent-activated cell sorting (FACS), for measuring mutant ALK kinase polypeptide are known in the art and provide a basis for diagnosing altered or abnormal levels of EML4-ALK or TFG-ALK fusion polypeptide expression. Normal or standard values for these fusion polypeptide expression are established by combining body fluids or cell extracts taken from normal mammalian subjects, preferably human, with antibody to EML4-ALK or TFG-ALK fusion polypeptide under conditions suitable for complex formation. The amount of standard complex formation may be quantified by various methods, but preferably by photometric means. Quantities of EML4-ALK or TFG-ALK fusion polypeptide expressed in subject, control, and disease samples from biopsied tissues are compared with the standard values. Deviation between standard and subject values establishes the parameters for diagnosing disease.

Peptide & Nucleic Acid Assays.

Similarly, AQUA peptides for the detection/quantification of expressed mutant ALK kinase polypeptide in a biological sample comprising cells from a tumor may be prepared and used in standard AQUA assays, as described in detail in Section E above. Accordingly, in some preferred embodiments of the methods of the invention, the ALK fusion polypeptide-specific reagent comprises a heavy isotope labeled phosphopeptide (AQUA peptide) corresponding to a peptide sequence comprising the fusion junction of an EML4-ALK fusion polypeptide or TFG-ALK fusion polypeptide, as described above in Section E.

Mutant ALK polypeptide-specific reagents useful in practicing the methods of the invention may also be mRNA, oligonucleotide or DNA probes that can directly hybridize to, and detect, fusion or truncated polypeptide expression transcripts in a biological sample. Such probes are discussed in detail in Section B above. Briefly, and by way of example, formalin-fixed, paraffin-embedded patient samples may be probed with a fluorescein-labeled RNA probe followed by washes with formamide, SSC and PBS and analysis with a fluorescent microscope. Also preferred are FISH probes, including breakpoint probes, that allow the fluorescent detection of gene rearrangements, such as the EML4-ALK deletion mutations on chromosome 2 (see Example 6).

Polynucleotides encoding mutant ALK kinase polypeptide may also be used for diagnostic purposes. The polynucleotides which may be used include oligonucleotide sequences, antisense RNA and DNA molecules, and PNAs. The polynucleotides may be used to detect and quantitate gene expression in biopsied solid tumor tissues in which expression of EML4-ALK or TFG-ALK fusion polypeptide or truncated active ALK kinase polypeptide may be correlated with disease. For example, the diagnostic assay may be used to distinguish between absence, presence, and excess expression of EML4-ALK or TFG-ALK fusion polypeptide, and to monitor regulation of ALK fusion polypeptide levels during therapeutic intervention.

In one preferred embodiment, hybridization with PCR probes which are capable of detecting polynucleotide sequences, including genomic sequences, encoding an ALK fusion polypeptide or truncated ALK kinase polypeptide, or closely related molecules, may be used to identify nucleic acid sequences that encode mutant ALK polypeptide. The construction and use of such probes is described in Section B above. The specificity of the probe, whether it is made from a highly specific region, e.g., 10 unique nucleotides in the fusion junction, or a less specific region, e.g., the 3' coding region, and the stringency of the hybridization or amplification (maximal, high, intermediate, or low) will determine whether the probe identifies only naturally occurring sequences encoding mutant ALK polypeptide, alleles, or related sequences.

Probes may also be used for the detection of related sequences, and should preferably contain at least 50% of the nucleotides from any of the mutant ALK polypeptide encoding sequences. The hybridization probes of the subject invention may be DNA or RNA and derived from the nucleotide sequences of SEQ ID NOs: 2, 19, and 21, most preferably encompassing the fusion junction (see FIGS. 1A-C, bottom panel and SEQ ID NOs: 7, 24, and 26), or from genomic sequence including promoter, enhancer elements, and introns of the naturally occurring EML-4, TFG, and ALK polypeptides, as further described in Section B above.

For example, an EML4-ALK fusion polynucleotide of the invention may be used in Southern or northern analysis, dot blot, or other membrane-based technologies; in PCR technologies; or in dip stick, pin, ELISA or chip assays utilizing fluids or tissues from patient biopsies to detect altered ALK polypeptide expression. Such qualitative or quantitative methods are well known in the art. In a particular aspect, the nucleotide sequences encoding a mutant ALK polypeptide of the invention may be useful in assays that detect activation or induction of various cancers, including lung carcinomas. Mutant ALK polynucleotides may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding EML4-ALK fusion polypeptide or truncated ALK kinase polypeptide in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease characterized by expression of mutant ALK kinase polypeptide, a normal or standard profile for expression is established. This may be accomplished by combining body fluids or cell extracts taken from normal subjects, either animal or human, with a sequence, or a fragment thereof, which encodes EML4-ALK or TFG-ALK fusion polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for mutant ALK polynucleotides of the invention may involve the use of polymerase chain reaction (PCR), a preferred assay format that is standard to those of skill in the art. See, e.g., MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989). PCR oligomers may be chemically synthesized, generated enzymatically, or produced from a recombinant source. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of an ALK fusion polypeptide or truncated ALK kinase polypeptide include radiolabeling or biotinylating nucleotides, coamplification of a control nucleic acid, and standard curves onto which the experimental results are interpolated (Melby et al., *J. Immunol. Methods,* 159: 235-244 (1993); Duplaa et al. *Anal. Biochem.* 229-236 (1993)). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the mutant ALK polynucleotides of the invention, as well the adjacent genomic region proximal and distal to them, may be used to generate hybridization probes that are useful for mapping the naturally occurring genomic sequence. The sequences may be mapped to a particular chromosome or to a specific region of the chromosome using well-known techniques. Such techniques include fluorescence in-situ hybridization (FISH), FACS, or artificial chromosome constructions, such as yeast artificial chromosomes, bacterial artificial chromosomes, bacterial P1 constructions or single chromosome cDNA libraries, as reviewed in Price, C. M., *Blood Rev.* 7:127-134 (1993), and Trask, B. J., *Trends Genet.* 7:149-154 (1991).

In one preferred embodiment, FISH is employed (as described in Verma et al. HUMAN CHROMOSOMES: A MANUAL OF BASIC TECHNIQUES, Pergamon Press, New York, N.Y. (1988)) and may be correlated with other physical chromosome mapping techniques and genetic map data. Examples of genetic map data can be found in the 1994 Genome Issue of *Science* (265: 1981f). Correlation between the location of the gene encoding EML4-ALK or TFG-ALK fusion polypeptide or truncated active ALK kinase polypeptide on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals. Dual-color breakpoint FISH probes, for example, can be employed to detect the presence or absence of mutant EML-4, TFG, and/or ALK genes in a sample.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti et al., *Nature* 336: 577-580 (1988)), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

Other suitable methods for nucleic acid detection, such as minor groove-binding conjugated oligonucleotide probes (see, e.g. U.S. Pat. No. 6,951,930, "Hybridization-Triggered Fluorescent Detection of Nucleic Acids") are known to those of skill in the art.

Biological Samples.

Biological samples useful in the practice of the methods of the invention may be obtained from any mammal in which a cancer characterized by the expression of an EML4-ALK or TFG-ALK fusion polypeptide is present or developing. In one embodiment, the mammal is a human, and the human may be a candidate for an ALK-inhibiting therapeutic for the treatment of a cancer, e.g. NSCLC. The human candidate may be a patient currently being treated with, or considered for treatment with, a ALK kinase inhibitor, such as WHI-131 and/or WHI-154. In another embodiment, the mammal is large animal, such as a horse or cow, while in other embodiments, the mammal is a small animal, such as a dog or cat, all of which are known to develop cancers, including lung carcinomas.

Any biological sample comprising cells (or extracts of cells) from a mammalian cancer is suitable for use in the methods of the invention. In the case of EML-ALK fusion polypeptide, any cancer, whether solid or non-solid, will be suitable. In the case of TFG-ALK, solid tumors are within the scope of the methods of the invention. For example, the biological sample may comprise cells obtained from an effusion, such as a pleural effusion. Pleural effusions (liquid that forms outside the lung in the thoracic cavity and which contains cancerous cells) are known to form in many patients with advanced lung cancer (including NSCLC), and the presence of such effusion is predictive of a poor outcome and short survival time. Standard techniques for obtaining pleural effusion samples have been described and are well known in the art (see Sahn, *Clin Chest Med.* 3(2): 443-52 (1982)). Circulating tumor cells may also be obtained from serum using tumor markers, cytokeratin protein markers or other methods of negative selection as described (see Ma et al., *Anticancer Res.* 23(1A): 49-62 (2003)). Serum and bone marrow samples may be particularly preferred for patients with leukemia. For cancers involving solid tumors, such as sarcomas and carcinomas, the biological sample may comprise cells obtained from a tumor biopsy, which maybe be obtained according to standard clinical techniques. For example, aberrant expression of ALK has been observed in a spectrum of cancers including neuroblastomas and neuroectodermal cancer. See, e.g., Pulford et al., supra. The TFG-ALK translocation mutant, however, has only been described in lymphoma and not previously observed in solid tumors.

A biological sample may comprise cells (or cell extracts) from a cancer in which an ALK fusion polypeptide is expressed and/or activated but wild type ALK kinase is not. Alternatively, the sample may comprise cells from a cancer in which both the mutant ALK polypeptide and wild type ALK kinase are expressed and/or activated, or in which wild type ALK kinase and/or EML-4 and/or TFG are expressed and/or active, but mutant ALK polypeptide is not.

Cellular extracts of the foregoing biological samples may be prepared, either crude or partially (or entirely) purified, in accordance with standard techniques, and used in the methods of the invention. Alternatively, biological samples comprising whole cells may be utilized in preferred assay formats such as immunohistochemistry (IHC), flow cytometry (FC), immunofluorescence (IF), and fluorescence in situ hybridization (FISH) as further described above. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

In practicing the disclosed method for determining whether a compound inhibits progression of a tumor characterized by an EML4-ALK or TFG-ALK fusion gene and/or fusion polypeptide, biological samples comprising cells from mammalian bone marrow transplant models or xenografts may also be advantageously employed. Preferred xenografts (or transplant recipients) are small mammals, such as mice, harboring human tumors that express a mutant ALK kinase polypeptide. Xenografts harboring human tumors are well known in the art (see Kal, *Cancer Treat Res.* 72: 155-69 (1995)) and the production of mammalian xenografts harboring human tumors is well described (see Winograd et al., *In Vivo.* 1(1): 1-13 (1987)). Similarly the generation and use of bone marrow transplant models is well described (see, e.g., Schwaller, et a., *EMBO J.* 17: 5321-333 (1998); Kelly et al., *Blood* 99: 310-318 (2002)). By "cancer characterized by" an EML4-ALK or TFG-ALK fusion polynucleotide and/or fusion polypeptide is meant a cancer in which such mutant ALK gene and/or expressed polypeptide are present, as compared to a cancer in which such fusion gene and/or fusion polypeptide are not present.

In assessing mutant ALK polynucleotide presence or polypeptide expression in a biological sample comprising cells from a mammalian cancer tumor, a control sample representing a cell in which such translocation and/or fusion protein do not occur may desirably be employed for comparative purposes. Ideally, the control sample comprises cells from a subset of the particular cancer (e.g. NSCLC) that is representative of the subset in which the mutation (e.g. EML4-ALK deletion mutation) does not occur and/or the fusion polypeptide is not expressed. Comparing the level in the control sample versus the test biological sample thus identifies whether the mutant ALK polynucleotide and/or polypeptide is/are present. Alternatively, since EML4-ALK and/or TFG-ALK fusion polynucleotide and/or polypeptide may not be present in the majority of cancers, any tissue that similarly does not express such mutant ALK polypeptide (or harbor the mutant polynucleotide) may be employed as a control.

The methods described below will have valuable diagnostic utility for cancers characterized by mutant ALK polynucleotide and/or polypeptide, and treatment decisions pertaining to the same. For example, biological samples may be obtained from a subject that has not been previously diagnosed as having a cancer characterized by an EML4-ALK deletion mutation and/or fusion polypeptide, nor has yet undergone treatment for such cancer, and the method is employed to diagnostically identify a tumor in such subject as belonging to a subset of tumors (e.g. NSCLC) in which EML4-ALK fusion polynucleotide and/or polypeptide is present and/or expressed. The methods of the invention may also be employed to monitor the progression or inhibition of a mutant ALK kinase polypeptide-expressing cancer following treatment of a subject with a composition comprising an ALK kinase-inhibiting therapeutic or combination of therapeutics.

Such diagnostic assay may be carried out subsequent to or prior to preliminary evaluation or surgical surveillance procedures. The identification method of the invention may be advantageously employed as a diagnostic to identify patients having cancer, such as NSCLC, driven by the EML4-ALK and/or TFG-ALK fusion protein(s) or by truncated ALK kinase, which patients would be most likely to respond to therapeutics targeted at inhibiting ALK kinase activity, such as WHI-131 and/or WHI-154 or their analogues. The ability to select such patients would also be useful in the clinical evaluation of efficacy of future ALK-targeted therapeutics as well as in the future prescription of such drugs to patients.

Diagnostics.

The ability to selectively identify cancers in which an EML4-ALK and/or TFG-ALK fusion polynucleotide and/or fusion polypeptide is/are present enables important new methods for accurately identifying such tumors for diagnostic purposes, as well as obtaining information useful in determining whether such a tumor is likely to respond to a ALK-inhibiting therapeutic composition, or likely to be partially or wholly non-responsive to an inhibitor targeting a different kinase when administered as a single agent for the treatment of the cancer.

Accordingly, in one embodiment, the invention provides a method for detecting the presence of a mutant ALK polynucleotide and/or its encoded mutant ALK polypeptide in a biological sample from a mammalian cancer, said method comprising the steps of:

(a) obtaining a biological sample from a mammalian cancer; and (b) utilizing at least one reagent that detects a fusion polynucleotide, or its encoded fusion polypeptide, comprising part of ALK with part of a secondary protein to determine whether an ALK mutant polynucleotide and/or its encoded mutant ALK polypeptide is present in said biological sample.

In some preferred embodiments the cancer is a solid tumor sarcoma or carcinoma, while in one embodiment the carcinoma is a lung carcinoma, such as NSCLC. In another preferred embodiment the mutant ALK polypeptide is a fusion polypeptide comprising residues 1116-1383 of ALK (SEQ ID NO: 5) with a portion of said secondary protein. In another preferred embodiment, the secondary protein is selected from the group consisting of EML-4 (SEQ ID NO: 3) and TRK-Fused Gene (TFG) protein (SEQ ID NO: 22). In still another preferred embodiment, the fusion polypeptide comprises residues 1-222 or residues 1-495 of EML-4 (SEQ ID NO: 3) or residues 1-138 of TFG (SEQ ID NO: 22).

In other preferred embodiments, the fusion polynucleotide comprises an EML4-ALK fusion polynucleotide (SEQ ID NOs: 2 or 19) or a TFG-ALK fusion polynucleotide (SEQ ID NO: 21), while in still another embodiment the fusion polypeptide comprises an EML4-ALK fusion polypeptide (SEQ ID NOs: 1 or 18) or a TFG-ALK fusion polypeptide (SEQ ID NO: 20). In yet another preferred embodiment, the fusion polynucleotide is an EML4-ALK fusion polynucleotide or polypeptide described above.

In more preferred embodiments, the method employs a reagent that comprises an EML4-ALK fusion polynucleotide and/or at least one EML4-ALK fusion polypeptide-specific reagent (antibody or AQUA peptide), as described above. In some preferred embodiments, the reagent comprises an isolated reagent that specifically binds to or detects a TFG-ALK fusion polypeptide (SEQ ID NO: 20) or TFG-ALK fusion polynucleotide (SEQ ID NO: 21), but does not bind to or detect either wild type TFG or wild type ALK. In other preferred embodiments, the reagent is a polymerase chain reaction (PCR) probe or a fluorescence in situ hybridization (FISH) probe. Certain preferred embodiments employ a heavy isotope labeled (AQUA) peptide that comprises the amino acid sequence of the fusion junction of TFG-ALK fusion polypeptide or truncation point within wild-type ALK.

In some preferred embodiments, the diagnostic methods of the invention are implemented in a flow-cytometry (FC), immuno-histochemistry (IHC), or immuno-fluorescence (IF) assay format, as described above. In another preferred embodiment, the activity of the EML4-ALK or TFG-ALK fusion polypeptide is detected. In other preferred embodiments, the diagnostic methods of the invention are implemented in a fluorescence in situ hybridization (FISH) or polymerase chain reaction (PCR) assay format, as described above.

The invention further provides a method for determining whether a compound inhibits the progression of a cancer characterized by an EML4-ALK or TFG-ALK fusion polynucleotide and/or fusion polypeptide, said method comprising the step of determining whether said compound inhibits the expression and/or activity of said EML4-ALK or TFG-ALK fusion polypeptide in said cancer. In one preferred embodiment, inhibition of expression and/or activity of the ALK fusion polypeptide is determined using at least one reagent that detects an EML4-ALK fusion polynucleotide or polypeptide of the invention and/or a TFG-ALK fusion polynucleotide or polypeptide described herein. Compounds suitable for inhibition of ALK kinase activity are discussed in more detail in Section G below.

Mutant ALK polynucleotide probes and polypeptide-specific reagents useful in the practice of the methods of the invention are described in further detail in sections B and D above. In one preferred embodiment, the ALK fusion polypeptide-specific reagent comprises a fusion polypeptide-specific antibody. In another preferred embodiment, the fusion polypeptide-specific reagent comprises a heavy-isotope labeled phosphopeptide (AQUA peptide) corresponding to the fusion junction of an ALK fusion polypeptide (see FIGS. 1A-C(bottom panel)). In yet another preferred embodiment, the fusion polynucleotide-specific reagent comprises a FISH probe corresponding to the fusion junction of an ALK fusion gene and/or breakpoints of wild type EML4, TFG, or ALK genes.

The methods of the invention described above may also optionally comprise the step of determining the level of expression or activation of other kinases, such as wild type ALK and EGFR, or other downstream signaling molecules in said biological sample. Profiling both ALK fusion polypeptide expression/activation and expression/activation of other kinases and pathways in a given biological sample can provide valuable information on which kinase(s) and pathway(s) is/are driving the disease, and which therapeutic regime is therefore likely to be of most benefit.

Compound Screening.

The discovery of the novel EML4-ALK fusion polypeptides described herein also enables the development of new compounds that inhibit the activity of this mutant ALK protein, particularly its ALK kinase activity. Accordingly, the invention also provides, in part, a method for determining whether a compound inhibits the progression of a cancer characterized by an EML4-ALK fusion polynucleotide and/or fusion polypeptide, said method comprising the step of determining whether said compound inhibits the expression and/or activity of said EML4-ALK fusion polypeptide in said cancer. In one preferred embodiment, inhibition of expression and/or activity of the EML4-ALK fusion polypeptide or is determined using at least one reagent that detects a fusion polynucleotide or fusion polypeptide of the invention. Preferred reagents of the invention have been described above. Compounds suitable for the inhibition of ALK kinase activity are described in more detail in Section G below.

The compound may, for example, be a kinase inhibitor, such as a small molecule or antibody inhibitor. It may be a pan-kinase inhibitor with activity against several different kinases, or a kinase-specific inhibitor. ALK kinase-inhibiting compounds are discussed in further detail in Section G below.

Patient biological samples may be taken before and after treatment with the inhibitor and then analyzed, using methods described above, for the biological effect of the inhibitor on ALK kinase activity, including the phosphorylation of downstream substrate protein. Such a pharmacodynamic assay may be useful in determining the biologically active dose of the drug that may be preferable to a maximal tolerable dose. Such information would also be useful in submissions for drug approval by demonstrating the mechanism of drug action. Identifying compounds with such desired inhibitory characteristics is further described in Section G below.

G. Therapeutic Inhibition of Cancers.

In accordance with the present invention, it has now been shown that the progression of a mammalian solid tumor cancer (NSCLC) in which EML4-ALK fusion protein is expressed may be inhibited, in vivo, by inhibiting the activity of ALK kinase in such cancer. Similarly as described herein, the activity of a mammalian solid tumor cancer in which TFG-ALK fusion protein is expressed may be similarly inhibited, in vivo, by inhibiting ALK kinase activity in such cancer. ALK activity in cancers characterized by expression of a mutant ALK polypeptide may be inhibited by contacting the cancer (e.g. a tumor) with an ALK kinase-inhibiting therapeutic, such as a small-molecule kinase inhibitor like WHI-131 or WHI-154. As further described in Example 2 below, growth inhibition of ALK fusion protein-expressing tumors, for example, can be accomplished by inhibiting the fusion kinase using an exemplary type of ALK-inhibiting therapeutic, siRNA. Accordingly, the invention provides, in part, a method for inhibiting the progression of a cancer that expresses EML4-ALK fusion polypeptide or solid tumor that expresses TFG-ALK fusion polypeptide by inhibiting the expression and/or activity of the mutant ALK kinase in the cancer.

An ALK kinase-inhibiting therapeutic may be any composition comprising at least one compound, biological or chemical, which inhibits, directly or indirectly, the expression and/or activity of ALK kinase in vivo, including the exemplary classes of compounds described below. Such compounds include therapeutics that act directly on ALK kinase itself, or on proteins or molecules that modify the activity of ALK, or that act indirectly by inhibiting the expression of ALK. Such compositions also include compositions comprising only a single ALK kinase inhibiting compound, as well as compositions comprising multiple therapeutics (including those against other RTKs), which may also include a non-specific therapeutic agent like a chemotherapeutic agent or general transcription inhibitor.

Small-Molecule Inhibitors.

In some preferred embodiments, an ALK-inhibiting therapeutic useful in the practice of the methods of the invention is a targeted, small molecule inhibitor, such as WHI-131 and WHI-154, or their analogues. WHI-131 and WHI-154 are quinazoline-type small molecule targeted inhibitors of ALK, and their properties have been described. See Marzec et al., Lab. Invest. 85(12): 1544-54 (2005). These compounds have been shown to induce apoptosis and suppress proliferation in lymphoma cells. Other small molecule targeted inhibitors of kinases are well known in the art. For example, Gleevec® (STI-571, Imatinib), which specifically binds to and blocks the ATP-binding site of BCR-ABL fusion kinase (as well as other kinases) thereby preventing phosphorylation and activation of this enzyme, is commercially available and its properties are well known. See, e.g., Dewar et al., *Blood* 105(8): 3127-32 (2005). Other small-molecule inhibitors of ALK are presently under development by Novartis, Inc., and Cephalon, Inc.

Small molecule targeted inhibitors are a class of molecules that typically inhibit the activity of their target enzyme by specifically, and often irreversibly, binding to the catalytic site of the enzyme, and/or binding to an ATP-binding cleft or other binding site within the enzyme that prevents the enzyme from adopting a conformation necessary for its activity. Small molecule inhibitors may be rationally designed using X-ray crystallographic or computer modeling of ALK kinase three-dimensional structure, or may found by high throughput screening of compound libraries for inhibition of ALK. Such methods are well known in the art, and have been described. Specificity of ALK inhibition may be confirmed, for example, by examining the ability of such compound to inhibit ALK activity, but not other kinase activity, in a panel of kinases, and/or by examining the inhibition of ALK activity in a biological sample comprising lung carcinoma cells, as described above. Such screening methods are further described below.

Antibody Inhibitors.

ALK kinase-inhibiting therapeutics useful in the methods of the invention may also be targeted antibodies that specifically bind to critical catalytic or binding sites or domains required for ALK activity, and inhibit the kinase by blocking access of ligands, substrates or secondary molecules to ALK, and/or preventing the enzyme from adopting a conformation necessary for its activity. The production, screening, and therapeutic use of humanized target-specific antibodies have been well-described. See Merluzzi et al., *Adv Clin Path.* 4(2): 77-85 (2000). Commercial technologies and systems, such as Morphosys, Inc.'s Human Combinatorial Antibody Library (HuCAL®), for the high-throughput generation and screening of humanized target-specific inhibiting antibodies are available.

The production of various anti-receptor kinase targeted antibodies and their use to inhibit activity of the targeted receptor has been described. See, e.g. U.S. Patent Publication No. 20040202655, "Antibodies to IGF-I Receptor for the Treatment of Cancers," Oct. 14, 2004, Morton et al.; U.S. Patent Publication No. 20040086503, "Human anti-Epidermal Growth Factor Receptor Single-Chain Antibodies," Apr. 15, 2004, Raisch et al.; U.S. Patent Publication No. 20040033543, "Treatment of Renal Carcinoma Using Antibodies Against the EGFr," Feb. 19, 2004, Schwab et. al. Standardized methods for producing, and using, receptor tyrosine kinase activity-inhibiting antibodies are known in the art. See, e.g., European Patent No. EP1423428, "Antibodies that Block Receptor Tyrosine Kinase Activation, Methods of Screening for and Uses Thereof," Jun. 2, 2004, Borges et al.

Phage display approaches may also be employed to generate ALK-specific antibody inhibitors, and protocols for bacteriophage library construction and selection of recombinant antibodies are provided in the well-known reference text CURRENT PROTOCOLS IN IMMUNOLOGY, Colligan et al. (Eds.), John Wiley & Sons, Inc. (1992-2000), Chapter 17, Section 17.1. See also U.S. Pat. No. 6,319,690, Nov. 20, 2001, Little et al.; U.S. Pat. No. 6,300,064, Oct. 9, 2001, Knappik et al.; U.S. Pat. No. 5,840,479, Nov. 24, 1998, Little et al.; U.S. Patent Publication No. 20030219839, Nov. 27, 2003, Bowdish et al.

A library of antibody fragments displayed on the surface of bacteriophages may be produced (see, e.g. U.S. Pat. No. 6,300,064, Oct. 9, 2001, Knappik et al.) and screened for binding to a soluble dimeric form of a receptor protein tyrosine kinase (like ALK). An antibody fragment that binds to the soluble dimeric form of the RTK used for screening is identified as a candidate molecule for blocking constitutive activation of the target RTK in a cell. See European Patent No. EP1423428, Borges et al., supra.

ALK binding targeted antibodies identified in screening of antibody libraries as describe above may then be further screened for their ability to block the activity of ALK, both in vitro kinase assay and in vivo in cell lines and/or tumors. ALK inhibition may be confirmed, for example, by examining the ability of such antibody therapeutic to inhibit ALK kinase activity, but not other kinase activity, in a panel of kinases, and/or by examining the inhibition of ALK activity in a biological sample comprising cancer cells, as described above. Methods for screening such compounds for ALK kinase inhibition are further described above.

Indirect Inhibitors.

ALK-inhibiting compounds useful in the practice of the disclosed methods may also be compounds that indirectly inhibit ALK activity by inhibiting the activity of proteins or molecules other than ALK kinase itself. Such inhibiting therapeutics may be targeted inhibitors that modulate the activity of key regulatory kinases that phosphorylate or de-phosphorylate (and hence activate or deactivate) ALK itself, or interfere with binding of ligands. As with other receptor tyrosine kinases, ALK regulates downstream signaling through a network of adaptor proteins and downstream kinases, including STAT5 and AKT. As a result, induction of cell growth and survival by ALK activity may be inhibited by targeting these interacting or downstream proteins. Drugs currently in development that could be used in this manner include Wartmanin.

ALK kinase activity may also be indirectly inhibited by using a compound that inhibits the binding of an activating molecule necessary for ALK to adopt its active conformation. Similarly, for example, the production and use of anti-PDGF antibodies to down-regulate PDGF receptor tyrosine kinase has been described. See U.S. Patent Publication No. 20030219839, "Anti-PDGF Antibodies and Methods for Producing Engineered Antibodies," Bowdish et al.

Indirect inhibitors of ALK activity may be rationally designed using X-ray crystallographic or computer modeling of ALK three dimensional structure, or may found by high throughput screening of compound libraries for inhibition of key upstream regulatory enzymes and/or necessary binding molecules, which results in inhibition of ALK kinase activity. Such approaches are well known in the art, and have been described. ALK inhibition by such therapeutics may be confirmed, for example, by examining the ability of the compound to inhibit ALK activity, but not other kinase activity, in a panel of kinases, and/or by examining the inhibition of ALK activity in a biological sample comprising cancer cells, e.g. NSCLC cells, as described above. Methods for identifying compounds that inhibit a cancer characterized by an EML4-ALK or TFG-ALK fusion polynucleotide and/or fusion polypeptide are further described below.

Anti-Sense and/or Transcription Inhibitors.

ALK inhibiting therapeutics may also comprise anti-sense and/or transcription inhibiting compounds that inhibit ALK kinase activity by blocking transcription of the gene encoding ALK and/or the EML4-ALK or TFG-ALK fusion genes or truncated ALK genes. For example, the inhibition of various receptor kinases, including VEGFR, EGFR, and IGFR, and FGFR, by antisense therapeutics for the treatment of cancer has been described. See, e.g., U.S. Pat. Nos. 6,734,017; 6,710,174, 6,617,162; 6,340,674; 5,783,683; 5,610,288.

Antisense oligonucleotides may be designed, constructed, and employed as therapeutic agents against target genes in accordance with known techniques. See, e.g. Cohen, J., *Trends in Pharmacol. Sci.* 10(11): 435-437 (1989); Marcus-Sekura, *Anal. Biochem.* 172: 289-295 (1988); Weintraub, H., *Sci. AM.* pp. 40-46 (1990); Van Der Krol et al., *BioTechniques* 6(10): 958-976 (1988); Skorski et al., *Proc. Natl. Acaed. Sci. USA* (1994) 91: 4504-4508. Inhibition of human carcinoma growth in vivo using an antisense RNA inhibitor of EGFR has recently been described. See U.S. Patent Publication No. 20040047847, "Inhibition of Human Squamous Cell Carcinoma Growth In vivo by Epidermal Growth Factor Receptor Antisense RNA Transcribed from a Pol III Promoter," Mar. 11, 2004, He et al. Similarly, an ALK-inhibiting therapeutic comprising at least one antisense oligonucleotide against a mammalian ALK gene (see FIG. 4 (SEQ ID NO: 6)) or EML4-ALK or TFG-ALK fusion polynucleotide or truncated ALK polynucleotide (see FIGS. 2A-C(SEQ ID NOs: 2, 19, and 21)) may be prepared according to methods described above. Pharmaceutical compositions comprising ALK-inhibiting antisense compounds may be prepared and administered as further described below.

Small Interfering RNA.

Small interfering RNA molecule (siRNA) compositions, which inhibit translation, and hence activity, of ALK through the process of RNA interference, may also be desirably employed in the methods of the invention. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, "Composition and Method for Inhibiting Expression of a Target Gene," Feb. 26, 2004, Kreutzer et al.; U.S. Patent Publication No. 20020086356, "RNA Sequence-Specific Mediators of RNA Interference," Jun. 12, 2003, Tuschl et al.; U.S. Patent Publication 20040229266, "RNA Interference Mediating Small RNA Molecules," Nov. 18, 2004, Tuschl et. al.

For example, as presently shown (see Example 2), siRNA-mediated silencing of expression of the EML4-ALK fusion protein in a human NSCLC cell line expressing the fusion protein selectively inhibited the progression of the disease in those cells, but not in control cells that do not express the mutant ALK protein.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available. See, e.g. Promega, Inc. (promega.com); Dharmacon, Inc. (dharmacon.com). Detailed technical manuals on the design, construction, and use of dsRNA for RNAi are available. See, e.g. Dharmacon's "RNAi Technical Reference & Application Guide"; Promega's "RNAi: A Guide to Gene Silencing." ALK-inhibiting siRNA products are also commercially available, and may be suitably employed in the method of the invention. See, e.g. Dharmacon, Inc., Lafayette, Colo. (Cat Nos. M-003162-03, MU-003162-03, D-003162-07 thru -10 (siGENOME™ SMARTselection and SMARTpool® siRNAs).

It has recently been established that small dsRNA less than 49 nucleotides in length, and preferably 19-25 nucleotides, comprising at least one sequence that is substantially identical to part of a target mRNA sequence, and which dsRNA optimally has at least one overhang of 1-4 nucleotides at an end, are most effective in mediating RNAi in mammals. See U.S. Patent Publication No. 20040038921, Kreutzer et al., supra; U.S. Patent Publication No. 20040229266, Tuschl et al., supra. The construction of such dsRNA, and their use in pharmaceutical preparations to silence expression of a target protein, in vivo, are described in detail in such publications.

If the sequence of the gene to be targeted in a mammal is known, 21-23 nt RNAs, for example, can be produced and tested for their ability to mediate RNAi in a mammalian cell, such as a human or other primate cell. Those 21-23 nt RNA molecules shown to mediate RNAi can be tested, if desired, in an appropriate animal model to further assess their in vivo effectiveness. Target sites that are known, for example target sites determined to be effective target sites based on studies with other nucleic acid molecules, for example ribozymes or antisense, or those targets known to be associated with a disease or condition such as those sites containing mutations or deletions, can be used to design siRNA molecules targeting those sites as well.

Alternatively, the sequences of effective dsRNA can be rationally designed/predicted screening the target mRNA of interest for target sites, for example by using a computer folding algorithm. The target sequence can be parsed in silico into a list of all fragments or subsequences of a particular length, for example 23 nucleotide fragments, using a custom Perl script or commercial sequence analysis programs such as Oligo, MacVector, or the GCG Wisconsin Package.

Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using in vitro RNA cleavage assays, cell culture, or animal models. See, e.g., U.S. Patent Publication No. 20030170891, Sep. 11, 2003, McSwiggen J. An algorithm for identifying and selecting RNAi target sites has also recently been described. See U.S. Patent Publication No. 20040236517, "Selection of Target Sites for Antisense Attack of RNA," Nov. 25, 2004, Drlica et al.

Commonly used gene transfer techniques include calcium phosphate, DEAE-dextran, electroporation and microinjection and viral methods (Graham et al. (1973) *Virol.* 52: 456; McCutchan et al., (1968), *J. Natl. Cancer Inst.* 41: 351; Chu at al. (1987), *Nucl. Acids Res.* 15: 1311; Fraley at al. (1980), *J. Biol. Chem.* 255: 10431; Capecchi (1980), *Cell* 22: 479). DNA may also be introduced into cells using cationic liposomes (Feigner et al. (1987), *Proc. Natl. Acad. Sci USA* 84: 7413). Commercially available cationic lipid formulations include Tfx 50 (Promega) or Lipofectamin 200 (Life Technologies). Alternatively, viral vectors may be employed to deliver dsRNA to a cell and mediate RNAi. See U.S. Patent Publication No. 20040023390, "siRNA-mediated Gene Silencing with Viral Vectors," Feb. 4, 2004, Davidson et al.

Transfection and vector/expression systems for RNAi in mammalian cells are commercially available and have been well described. See, e.g. Dharmacon, Inc., DharmaFECT™ system; Promega, Inc., siSTRIKE™ U6 Hairpin system; see also Gou at al. (2003) *FEBS.* 548, 113-118; Sui, G. et al. A DNA vector-based RNAi technology to suppress gene expression in mammalian cells (2002) *Proc. Natl. Aced. Sci.* 99, 5515-5520; Yu et al. (2002) *Proc. Natl. Acad. Sci.* 99, 6047-6052; Paul, C. et al. (2002) *Nature Biotechnology* 19, 505-508; McManus at al. (2002) RNA 8, 842-850.

siRNA interference in a mammal using prepared dsRNA molecules may then be effected by administering a pharmaceutical preparation comprising the dsRNA to the mammal. The pharmaceutical composition is administered in a dosage sufficient to inhibit expression of the target gene. dsRNA can typically be administered at a dosage of less than 5 mg dsRNA per kilogram body weight per day, and is sufficient to inhibit or completely suppress expression of the target gene. In general a suitable dose of dsRNA will be in the range of 0.01 to 2.5 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. A pharmaceutical composition comprising the dsRNA is administered once daily, or in multiple sub-doses, for example, using sustained release formulations well known in the art. The preparation and administration of such pharmaceutical compositions may be carried out accordingly to standard techniques, as further described below.

Such dsRNA may then be used to inhibit ALK expression and activity in a cancer, by preparing a pharmaceutical preparation comprising a therapeutically-effective amount of such dsRNA, as described above, and administering the preparation to a human subject having a cancer expressing EML4-ALK or TFG-ALK fusion protein or truncated active ALK kinase, for example, via direct injection to the tumor. The similar inhibition of other receptor tyrosine kinases, such as VEGFR and EGFR using siRNA inhibitors has recently been described. See U.S. Patent Publication No. 20040209832, Oct. 21, 2004, McSwiggen et al.; U.S. Patent Publication No. 20030170891, Sep. 11, 2003, McSwiggen; U.S. Patent Publication No. 20040175703, Sep. 9, 2004, Kreutzer et al.

Therapeutic Compositions: Administration.

ALK kinase-inhibiting therapeutic compositions useful in the practice of the methods of the invention may be administered to a mammal by any means known in the art including, but not limited to oral or peritoneal routes, including intravenous, intramuscular, intraperitoneal, subcutaneous, transdermal, airway (aerosol), rectal, vaginal and topical (including buccal and sublingual) administration.

For oral administration, an ALK-inhibiting therapeutic will generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. The carrier may consist exclusively of an aqueous buffer ("exclusively" means no auxiliary agents or encapsulating substances are present which might affect or mediate uptake of the ALK-inhibiting therapeutic). Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

ALK kinase-inhibiting therapeutic compositions may also include encapsulated formulations to protect the therapeutic (e.g. a dsRNA compound) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Uposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075. An encapsulated formulation may comprise a viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

ALK-inhibiting compositions can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.*, 2, 139; DELIVERY STRATEGIES FOR ANTISENSE OLIGONUCLEOTIDE THERAPEUTICS, ed. Akbtar, 1995, Maurer et al., 1999, *Mol. Membr. Biol.*, 16, 129-140; Hofland and Huang, 1999, *Handb. Exp. Pharmacol.*, 137, 165-192; and Lee et al., 2000, ACS Symp. Ser., 752, 184-192. Belgelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

ALK-inhibiting therapeutics can be administered to a mammalian tumor by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (O'Hare and Normand, International PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, *Clin. Cancer Res.*, 5, 2330-2337 and Barry et al., International PCT Publication No. WO 99/31262.

Pharmaceutically acceptable formulations of ALK kinase-inhibitory therapeutics include salts of the above-described compounds, e.g., acid addition salts, for example, salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

Administration routes that lead to systemic absorption (i.e. systemic absorption or accumulation of drugs in the blood stream followed by distribution throughout the entire body), are desirable and include, without limitation: intravenous, subcutaneous, intraperitoneal, inhalation, oral, intrapulmonary and intramuscular. Each of these administration routes exposes the ALK-inhibiting therapeutic to an accessible diseased tissue or tumor. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, *Fundam. Clin. Pharmacol.*, 13, 16-26); biodegradable polymers, such as poly (DL-lactide-coglycolide) microspheres for sustained release delivery after intracerebral implantation (Emerich et al, 1999, *Cell Transplant* 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (*Prog Neuro-psychopharmacol Biol Psychiatry*, 23, 941-949, 1999). Other non-limiting examples of delivery strategies for the ALK-inhibiting compounds useful in the method of the invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

Therapeutic compositions comprising surface-modified liposomes containing poly (ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta,* 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Therapeutic compositions may include a pharmaceutically effective amount of the desired compounds in a pharmaceutically acceptable carrier or diluent. Acceptable carriers or diluents for therapeutic use are well known in the pharmaceutical art, and are described, for example, in REMINGTON'S PHARMACEUTICAL SCIENCES, Mack Publishing Co. (A. R. Gennaro, Ed. 1985). For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

An ALK-inhibiting therapeutic useful in the practice of the invention may comprise a single compound as described above, or a combination of multiple compounds, whether in the same class of inhibitor (i.e. antibody inhibitor), or in different classes (i.e antibody inhibitors and small-molecule inhibitors). Such combination of compounds may increase the overall therapeutic effect in inhibiting the progression of a fusion protein-expressing cancer. For example, the therapeutic composition may a small molecule inhibitor, such as WHI-131 and/or WHI-154 alone, or in combination with other inhibitors targeting ALK activity and/or other small molecule inhibitors. The therapeutic composition may also comprise one or more non-specific chemotherapeutic agent in addition to one or more targeted inhibitors. Such combinations have recently been shown to provide a synergistic tumor killing effect in many cancers. The effectiveness of such combinations in inhibiting ALK activity and tumor growth in vivo can be assessed as described below.

Identification of Mutant ALK Kinase-Inhibiting Compounds.

The invention also provides, in part, a method for determining whether a compound inhibits the progression of a cancer characterized by an EML4-ALK or TFG-ALK fusion polynucleotide and/or fusion polypeptide, by determining whether the compound inhibits the activity of EML4-ALK or TFG-ALK fusion polypeptide or truncated ALK kinase polypeptide in the cancer. In some preferred embodiments, inhibition of activity of ALK is determined by examining a biological sample comprising cells from bone marrow, blood, pleural effusion, or a tumor. In another preferred embodiment, inhibition of activity of ALK is determined using at least one mutant ALK polynucleotide or polypeptide-specific reagent of the invention.

The tested compound may be any type of therapeutic or composition as described above. Methods for assessing the efficacy of a compound, both in vitro and in vivo, are well established and known in the art. For example, a composition may be tested for ability to inhibit ALK in vitro using a cell or cell extract in which ALK is activated. A panel of compounds may be employed to test the specificity of the compound for ALK (as opposed to other targets, such as EGFR or PDGFR).

Another technique for drug screening which may be used provides for high throughput screening of compounds having suitable binding affinity to a protein of interest, as described in published PCT application WO84/03564. In this method, as applied to mutant ALK polypeptides, large numbers of different small test compounds are synthesized on a solid substrate, such as plastic pins or some other surface. The test compounds are reacted with mutant ALK polypeptide, or fragments thereof, and washed. Bound mutant polypeptide (e.g. EML4-ALK fusion polypeptide) is then detected by methods well known in the art. Purified mutant ALK polypeptide can also be coated directly onto plates for use in the aforementioned drug screening techniques. Alternatively, non-neutralizing antibodies can be used to capture the peptide and immobilize it on a solid support.

A compound found to be an effective inhibitor of ALK activity in vitro may then be examined for its ability to inhibit the progression of a cancer expressing EML4-ALK or TFG-ALK fusion polypeptide and/or truncated ALK kinase polypeptide, in vivo, using, for example, mammalian xenografts harboring human tumors, such as NSCLC. In this way, the effects of the drug may be observed in a biological setting most closely resembling a patient. The drug's ability to alter signaling in the cancerous cells or surrounding stromal cells may be determined by analysis with phosphorylation-specific antibodies. The drug's effectiveness in inducing cell death or inhibition of cell proliferation may also be observed by analysis with apoptosis specific markers such as cleaved caspase 3 and cleaved PARP. Similarly, mammalian bone marrow transplants (e.g. mice) harboring human leukemias that are driven by the mutant ALK protein may be employed. In this procedure, bone marrow cells known to be driven by mutant ALK kinase are transplanted in the mouse. The growth of the cancerous cells may be monitored. The mouse may then be treated with the drug, and the effect of the drug treatment on cancer phenotype or progression be externally observed. The mouse is then sacrificed and the transplanted bone marrow removed for analysis by, etc., IHC and Western blot.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The teachings of all references cited above and below are hereby incorporated herein by reference. The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Identification of ALK Kinase Activity in Solid Tumors by Global Phosphopeptide Profiling A. Profiling of Human NSCLC Cell Lines.

The global phosphorylation profile of kinase activation in 22 human NSCLC cell lines, including H2228, were examined using a recently described and powerful technique for the isolation and mass spectrometric characterization of modified peptides from complex mixtures (the "IAP" technique, see Rush et al., supra). The AP technique was performed using a phosphotyrosine-specific antibody (CELL SIGNALING TECHNOLOGY, INC., Beverly, Mass., 2003/04 Cat. #9411) to isolate, and subsequently characterize, phosphotyrosine-containing peptides from extracts of the NSCLC cell lines.

Specifically, the AP approach was employed go facilitate the identification of tyrosine kinases responsible for protein phosphorylation in each of the NSCLC cell lines. In particular, atypical or unusual kinase activity was considered.
Cell Culture.

All cell culture reagents were purchased from Invitrogen, Inc. A total of 41 human NSCLC cell lines were examined. Human NSCLC cell lines, H520, H838, H1437, H1563, H1568, H1792, H1944, H2170, H2172, H2228, H2347, A549, H441, H1703, H1373, and H358, were obtained from American Type Culture Collection, and cultured in RPMI 1640 medium with 10% FBS and adjusted to contain 2 mM L-glutamine, 1.5 g/L sodium bicarbonate, 4.5 g/L glucose, 10 mM HEPES, 1.0 mM sodium pyruvate, penicillin/streptomycin. An additional six human NSCLC cell lines, HCC78, Cal-12T, HCC366, HCC15, HCC44, and LOU-NH91, were purchased from DSMZ, and cultured in RPMI 1640 containing 10% FBS and penicillin/streptomycin. Cells were maintained in a 5% CO2 incubator at 37° C.

For the immunoaffinity precipitation and immunoblot experiments, cells were grown to 80% confluence and then starved in RPMI medium without FBS overnight before harvesting.

Phosphopeptide Immunoprecipitation.

100 million cells were lysed in urea lysis buffer (20 mM Hepes, pH 8.0, 9 M Urea, 1 mM sodium vanadate, 2.5 mM sodium pyrophosphate, 1 mM beta-glycerophosphate). The lysate was sonicated and cleared by centrifugation. Cleared lysate was reduced by DTT and alkylated with iodoacetamide, as described previously (see Rush et al., Nat. Biotechnol. 23(1): 94-101 (2005)). Samples were then diluted 4 times with 20 mM Hepes to reduce Urea concentration to 2M, and digested by trypsin overnight at room temperature with gentle shaking.

Digested peptides were crudely purified with Sep-Pak C18 columns, as previously described (see Rush et al., supra.). Elute was lyophilized and dried peptides were dissolved in 1.4 ml of MOPS IP buffer (50 mM MOPS/NaOH pH 7.2, 10 mM Na2PO4, 50 mM NaCl) and insoluble material removed by centrifugation. Immunoprecipitation was carried at 4° C. for overnight with 160 µg of Phospho-Tyrosine 100 antibody (Cell Signaling Technology) coupled to protein G agarose beads (Roche). The beads were then washed 3 times with 1 ml MOPS IP buffer and twice with 1 ml HPLC grade dH2O in the cold. Phosphopeptides were eluted from beads with 60 µl 0.1% TFA followed by a second elution with 40 µl 0.1% TFA and the fractions were pooled. The eluted peptides were concentrated using a ZipTip column (Millipore), and analyzed with LC-MS/MS. Mass spectra were collected with an LTQ ion trap mass spectrometer (ThermoFinnigan).

Analysis by LC-MS/MS Mass Spectrometry.

Peptides in the IP eluate (100 µl) were concentrated and separated from eluted antibody using Stop and Go extraction tips (StageTips) (see Rappsilber et al., Anal. Chem., 75(3): 663-70 (2003)). Peptides were eluted from the microcolumns with 1 µl of 60% MeCN, 0.1% TFA into 7.6 µl of 0.4% acetic acid/0.005% heptafluorobutyric acid (HFBA).

Each phosphopeptide sample was LC-MS analyzed in duplicate. A fused silica microcapillary column (125 µm×18 cm) was packed with C18 reverse-phase resin (Magic C18AQ, 5 µm particles, 200 A pore size, Michrom Bioresources, Auburn, Calif.). Samples (4 µL) were loaded onto this column with an autosampler (LC Packings Famos, San Francisco, Calif.) and eluted into the mass spectrometer by a 55-min linear gradient of 7 to 30% acetonitrile in 0.1% formic acid. The gradient was delivered at approximately abc nl/min using a binary HPLC pump (Agilent 1100, Palo Alto, Calif.) with an in-line flow splitter. Eluting peptide ions were mass analyzed with a hybrid linear ion trap-7 Tesla ion cyclotron resonance Fourier transform instrument (LTQ-FT, Thermo Finnigan, San Jose, Calif.).

A top-seven method was employed, whereby 7 data-dependent MS/MS scans in the linear ion trap were collected based on measurements made during the previous MS survey scan in the ICR cell, with the linear ion trap and the Fourier transform instrument operating concurrently. MS scans were performed at 375-1800 m/z with an automatic gain control (AGC) target of 8×106 and a mass resolution of 105. For MS/MS the AGC was 8×106, the dynamic exclusion time was 25 s, and singly-charged ions were rejected by charge-state screening.

Database Analysis & Assignments.

Peptide sequences were assigned to MS/MS spectra using TurboSequest software (v.27, rev.12) (ThermoFinnigan) and a composite forward/reverse IPI human protein database. Search parameters were: trypsin as protease; 1.08 Da precursor mass tolerance; static modification on cysteine (+57.02146, carboxamidomethylation); and dynamic modifications on serine, threonine and tyrosine (+79.96633 Da, phosphorylation), lysine (+8.01420, 13C615N2), arginine (+6.02013, 13C6) and methionine (+15.99491, oxidation). A target/decoy database approach was used to establish appropriate score-filtering criteria such that the estimated false-positive assignment rate was <1%. In addition to exceeding charge-dependent XCorr thresholds ($z=1$, XCorr≥1.5, for $z=2$, XCorr≥2.2, for $z=3$, XCorr≥3.3), assignments were required to contain phosphotyrosine, to have a mass accuracy of −5 to +25 ppm, and to contain either all-light or all-heavy lysine/arginine residues.

Assignments passing these criteria were further evaluated using a custom quantification program, Vista (Bakalarski et al., manuscript in preparation) to calculate peak areas and ultimately a relative abundance between heavy and light forms of each peptide. Identified peptides with signal-to-noise in the MS scan below 15 were not considered for quantification. For those peptides found only in one of the conditions the signal-to-noise ratio was used instead.

Searches were done against the NCBI human database released on Aug. 24, 2004 containing 27,175 proteins allowing oxidized methionine (M+16) and phosphorylation (Y+80) as dynamic modifications. All spectra supporting the final list of assigned sequences (not shown here) were reviewed by at least three scientists to establish their credibility.

The foregoing IAP analysis identified over 2000 non-redundant phosphotyrosine-containing peptides, over 1,500 phosphotyrosine sites, and more than 1,000 tyrosine phosphorylated proteins, the majority of which are novel, from the cell lines examined (data not shown). Receptor tyrosine kinases known to be involved in NSCLC signaling were observed to be tyrosine phosphorylated in many cell lines, such as EGFR, Her2, Her3, EphA2 and Met. High levels of EGFR phosphopeptides were observed in several cell lines including HCC827 and H3255, two cell lines known to express amplified levels of genetically activated forms of EGFR confirming the method identifies receptor tyrosine kinases known to be active in NSCLC cell lines.

Three cell lines expressed receptor tyrosine kinases not observed in other NSCLC cell lines. Large amounts of tyrosine phosphorylated peptides from Ros, ALK, and PDGFR alpha were observed in HCC78, H2228, and H1703 cell lines respectively. The NSCLC cell line H2228, which highly expresses ALK, was selected for further examination.

B. Profiling of Human NSCLC Tumor Samples.

The IAP technique, substantially as described in Part A above, was subsequently applied to examine global phospho-profiles of a panel of 154 human tumor samples from NSCLC patients. Tissues were obtained from the Second Xiangya Hospital, China.

Frozen tissue samples were cut into small pieces, homogenized in lysis buffer (20 mM HEPES pH 8.0, 9 M Urea, 1 mN sodium vanadate, supplemented with 2.5 mM sodium pyrophosphate, 1 mM b-glycerol-phosphate, 1 ml lysis buffer for 100 mg of frozen tissue) using a polytron for 2 times of 20 sec. each time. Homogenate was then briefly sonicated. Cleared lysate was reduced by DTT and alkylated with iodoacetamide, as described previously (see Rush et al., *Nat. Biotechnol.* 23(1): 94-101 (2005)). Samples were then diluted 4 times with 20 mM Hepes to reduce Urea concentration to 2M, and digested by trypsin overnight at room temperature with gentle shaking.

Digested peptides were crudely purified with Sep-Pak C18 columns, as previously described (see Rush et al., supra.). Elute was lyophilized and dried peptides were dissolved in 1.4 ml of MOPS IP buffer (50 mM MOPS/NaOH pH 7.2, 10 mM Na2PO4, 50 mM NaCl) and insoluble material removed by centrifugation. Immunoprecipitation was carried at 4° C. for overnight with 160 μg of Phospho-Tyrosine 100 antibody (Cell Signaling Technology) coupled to protein G agarose beads (Roche). The beads were then washed 3 times with 1 ml MOPS IP buffer and twice with 1 ml HPLC grade dH2O in the cold. Phosphopeptides were eluted from beads with 60 μl 0.1% TFA followed by a second elution with 40 μl 0.1% TFA and the fractions were pooled. The eluted peptides were concentrated using a ZipTip column (Millipore), and analyzed with LC-MS/MS. Mass spectra were collected with an LTQ ion trap mass spectrometer (ThermoFinnigan).

Phosphopeptide immunoprecipitation, followed by LC-MS/MS spectrometry analysis was then carried out as described above in Part A. Database searching and sequence assignments were made substantially as described above in Part A, but using the NCBI human database released on Aug. 24, 2004 containing 27,970 proteins.

The foregoing IAP analysis identified over 2000 non-redundant phosphotyrosine-containing peptides, over 1,500 phosphotyrosine sites, and more than 1,000 tyrosine phosphorylated proteins from the human tumor samples examined (data not shown). Receptor tyrosine kinases known to be involved in NSCLC signaling were again observed to be tyrosine phosphorylated in many tumors, such as EGFR, Her2, Her3, EphA2 and Met. High levels of EGFR phosphopeptides were again observed in several tumor samples confirming that the method identifies receptor tyrosine kinases known to be active in NSCLC cell lines.

Five patient samples expressed receptor tyrosine kinases not observed in other NSCLC cell lines and tumors. Large amounts of tyrosine-phosphorylated peptides from ALK were observed in patients CS010/11, CS045, and CS110. These three tumors, which highly express ALK, were selected for further examination.

EXAMPLE 2

Isolation & Sequencing of Three ALK Fusion Genes

A. Sequencing in Human NSCLC Cell Line.

Given the high phosphorylation level of ALK kinase detected in the NSCLC cell line H2228, 5' rapid amplification of cDNA ends on the sequence encoding the kinase domain of ALK was conducted in order to determine whether a chimeric ALK transcript was present.

Rapid Amplification of Complementary DNA Ends

RNeasy Mini Kit (Qiagen) was used to extract RNA from the H2228 cell line. DNA was extracted with the use of DNeasy Tissue Kit (Qiagen). Rapid amplification of cDNA ends was performed with the use of 5' RACE system (Invitrogen) with primers ALK-GSP1 for cDNA synthesis and ALK-GSP2 and ALK-GSP3 for a nested PCR reaction.

5' RACE

Figures 5A, 5B:
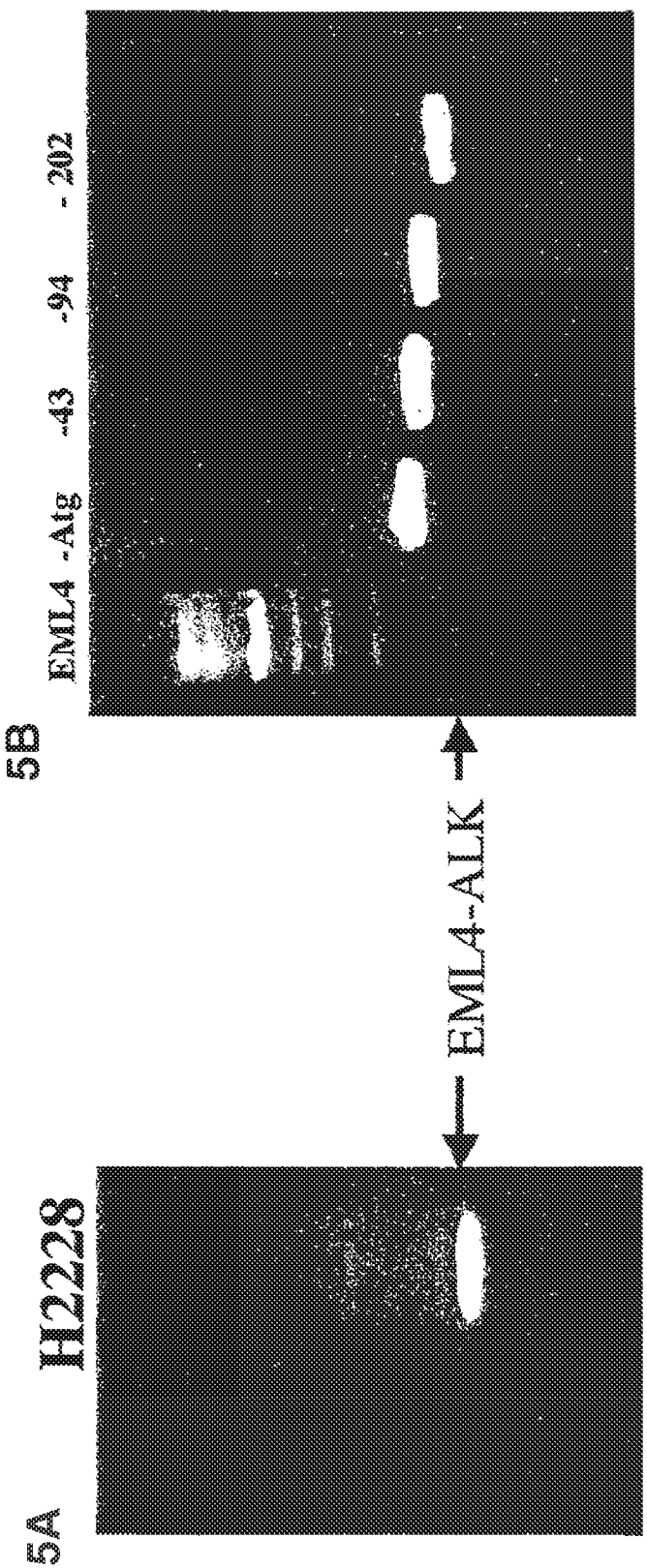

FIG. 5A shows the detection of the EML4-ALK fusion gene (short variant) by 5'RACE and the detection of the PCR amplification product after 2 rounds. The PCR product was purified with PCR purification kit (Qiagen) and sequenced using ALK-GSP3 an ABI 3130 capillary automatic DNA sequencer (Applied Biosystems). Sequence analysis of the resultant product revealed that the kinase domain and C-terminal of ALK was fused to the EML-4 gene N-terminus (see FIG. 1, panel B). The EML4-ALK fusion gene (short variant) was in-frame and fused the first 233 amino acids of EML-4 to the last 562 amino acids of ALK (see FIG. 1, panel B). EML-4 and ALK genes are both located on chromosome 2, thus the fusion gene was created by gene deletion between these two loci.

The following primers were used:

ALK-GSP1: 5'-GCAGTAGTTGGGGTTGTAGTC (SEQ ID NO: 9)

ALK-GSP2: 5'-GCGGAGCTTGCTCAGCTTGT (SEQ ID NO: 10)

ALK-GSP3: 5'-TGCAGCTCCTGGTGCTTCC (SEQ ID NO: 11)

PCR Assay

RT-PCR analysis was performed to confirm the N-terminus of EML-4 is intact in the fusion protein (see FIG. 5B). First-strand cDNA was synthesized from 2.5 mg of total RNA with the use of SuperScript™ III first-strand synthesis system (Invitrogen) with oligo $(dT)_{20}$. Then, the EML4-ALK fusion gene was amplified with the use of primer pairs EML-Atg and ALK-GSP3. The reciprocal fusion was detected with the use of primer pairs EML-4-43 and ALK-GSP3 and EML-4-94 and ALK-GSP3 and EML4-202 and ALK-GSP3. For genomic PCR, amplification of the fusion gene was performed with the use of Platinum Taq DNA polymerase high fidelity (Invitrogen) with primer pairs EML-4-atg and ALK-tga.

The following primers were used:

ALK-GSP3: 5'-TGCAGCTCCTGGTGCTTCC (SEQ ID NO: 12)

EML4-Atg: 5'-CGCAAGATGGACGGTTTGGC (SEQ ID NO: 13)

EML4-43: 5'-TGTTCAAGATCGCCTGTCAGCTCT (SEQ ID NO: 14)

EML4-94: 5'-TGAAATCACTGTGCTAAAGGCGGC (SEQ ID NO: 15)

EML4-202: 5'-AAGCCCTCGAGCAGTTATTCCCAT (SEQ ID NO: 16)

ALK-Tga: 5'-GAATTCCGCCGAGCTCAGGGCCCAG (SEQ ID NO: 17)

Of note, in the EML4-ALK fusion (short variant), the ALK moiety is fused to the EML-4 moiety at precisely the same point in ALK has been observed in other ALK fusions, such as the NPM-ALK fusion occurring in ALCL. The kinase domain of ALK in the H2228 cell line was further sequenced from genomic DNA and found to be wild type. Hence, the deletion mutation discovered in H2228 does not affect the ALK kinase domain. Further, wild type EML-4 is tyrosine phosphorylated only at a site that is not present in the EML4-ALK fusion protein (short variant), suggesting that the N-terminal coiled coil domain that is conserved in the fusion protein (see FIG. 1A) may function to dimerize and activate ALK, as well as to promote interaction with wild type ALK.

B. Sequencing in Human NSCLC Cell Line.

Similarly, given the high phosphorylation level of ALK kinase detected in the human NSCLC tumor samples from patients CS010/11, CS045, and CS110, 5' rapid amplification of cDNA ends on the sequence encoding the kinase domain of ALK was conducted in order to determine whether a chimeric ALK transcript was present in these tumors.

Rapid amplification of complementary DNA ends and 5' RACE was carried out, substantially as described above in Part A, with primers ALK-GSP1 for cDNA synthesis and ALK-GSP2 and ALK-GSP3 for a nested PCR reaction.

FIG. 5C shows the detection of the EML4-ALK fusion genes (both short and long variants) by 5'RACE in two patient samples, and the detection of the TFG-ALK fusion gene in one patient, and the detection of the PCR amplification product after 2 rounds. The PCR products were purified and sequenced substantially as described above in Part A. Sequence analysis of the resultant products revealed that the kinase domain and C-terminal of ALK were fused to the EML-4 gene N-terminus in two different variants (see FIGS. 1A-1B, panel B). The EML4-ALK fusion genes were in-frame and fused the first 233 amino acids (short variant) or first 495 amino acids (long variant) of EML-4 to the last 562 amino acids of ALK (see FIGS. 1A-1B, panel B). EML-4 and ALK genes are both located on chromosome 2, thus the fusion gene was created by gene deletion between these two loci. The observation of the fusion gene (short variant) in patient CS045 confirmed the finding of this mutant gene in the human cell line H2228.

The TFG-ALK fusion gene was also in-frame and fused the first 138 amino acids of TFG to the last 562 amino acids of ALK (see FIG. 1C, panel B). TFG and ALK genes are located on different chromosomes (chromosomes 6 and 2, respectively), thus the fusion gene was created by gene translocation between these two loci. Interestingly, the fusion of TPG to ALK occurred at exactly the same point in ALK as observed for the fusion of the two EML4-ALK variants, Indicating that truncation of ALK in solid tumors at this point may be a common occurrence.

The same primers were used as described in Part A above. RT-PCR analysis was performed, substantially as described in Part A above, to confirm the N-terminus of EML-4 and TFG are intact in the fusion proteins (see FIG. 6 (panel B)). Primer pairs for EML-4 and ALK were as described in Part A above.

The following primer pair was used for TFG:
TFG-FI: 5'-TTTGTTAATGGCCAGCCAAGACCC-3 (SEQ ID NO: 28)

Of note, in both EML4-ALK fusion variants, the ALK moiety is fused to the EML-4 moiety at precisely the same point in ALK has been observed in other ALK fusions, such as the NPM-ALK fusion occurring in ALCL. Further, wild type EML-4 is tyrosine phosphorylated only at a site that is not present in the EML4-ALK fusion proteins, suggesting that the N-terminal coiled coil domain that is conserved in the fusion proteins (see FIGS. 1A-1B) may function to dimerize and activate ALK, as well as to promote interaction with wild type ALK. Also of note, the fusion of the TG moiety to ALK also occurs at precisely the same point in ALK, and indeed the fusion of TFG to ALK at this point has been described in human lymphoma (see Hemandez et al. (2002), supra.), but has not previously been described in human solid tumors, such as NSCLC.

EXAMPLE 3

Growth Inhibition of ALK Fusion-Expressing Mammalian Solid Tumors Using siRNA

In order to confirm that the truncated/fusion forms of ALK are driving cell growth and survival in NSCLC cell line H2228 as well as NSCLC tumor samples from patients CS010/11, CS045, and CS110, the ability of siRNA (against ALK) to inhibit growth of these cells and tumors may be examined.

ALK SMARTpool siRNA duplexes (proprietary target sequences—data not shown) may be purchased, for example, from Dharmacon Research, Inc. (Lafayette, Colo.). A non-specific SMARTpool siRNA is used as a control. Cells are transfected with the siRNA via electroporation. Briefly, 2×10 cells (H2228) are pulsed once (20 ms; 275V, K562 20 ms; 285V) using a square-wave electroporator (BTX Genetronics, San Diego, Calif.), incubated at room temperature for 30 minutes and transferred to T150 flasks with 30 ml RPMI-1640/10% FBS.

The number of viable cells is determined with the Cell-Titer 96 AQ$_{ueous}$ One solution cell proliferation assay (Promega). IC$_{50}$ is calculated with the use of OriginPro 6.1 software (OriginLab). The percentage of apoptotic cells at 48 hours may be determined by flow cytometric analysis of Cleaved-Caspase-3 (Cell Signaling Technology).

Immunoblot analysis will reveal that the expression of ALK is specifically and significantly reduced at 72 hours following transfection of the siRNA into H2228 cells or tumor cells from patients CS010/11, CS045, and CS110. Down regulation of ALK is expected to result in strong inhibition of cell growth. Treatment with ALK siRNA is also expected to result in increased apoptosis of these solid tumor cells. These results will further indicate that the mutant/fused ALK kinases in the H2228 cell line and patient tumors are driving the proliferation and growth of these NSCLC cells, and that such growth and proliferation may be inhibited by using siRNA to inhibit ALK kinase expression and activity.

EXAMPLE 4

Growth Inhibition of ALK Fusion-Expressing Mammalian Solid Tumors Using WI-131 and/or WI-154

To further confirm that the mutant ALK fusion proteins are driving the growth and viability of the NSCLC cell line H2228 and NSCLC tumor cells from patients CS010/11, CS045, and CS110, the cells may be treated with a targeted inhibitor of ALK kinase, such as WI-131 and/or WI-154. WI-131 and W-154 are quinazoline-type small molecule inhibitors of ALK kinase, and their activity against the NPM-ALK fusion protein in T-cell lymphoma has been described. See Marzec et al., supra.

Briefly, NSCLC cells are cultured, and a cell growth inhibition assay is performed with CellTiter 96 AQueous One Solution Cell Proliferation Assay (Promega) according to manufacturer's suggestion. Briefly, 1000 to 5000 cells are seeded onto flat-bottomed 96-well plates and grown in complete medium with 10% FBS. After 24 hours, the cell medium is changed to 100 µl complete growth medium with 10% FBS containing various concentrations of the drug, and the cells are incubated for an additional 72 hours. Each drug concentration is applied to triplicate well of cells. At the end of the incubation, 20 µl of CellTiter 96 AQ$_{ueous}$ One solution is added to each well, and the plate was incubated for 1-4 hours. Absorbance is read at 490 nm using a Titan Multiskan Ascent microplate reader (Titertek Instrument). Growth inhibition may be expressed as mean±SD value of percentage of absorbance reading from treated cells versus untreated cells. The assay is repeated at least three times.

Such analysis is expected to confirm that the ALK fusion proteins (EML4-ALK (short and long variants), TFG-ALK) are driving growth and survival of a subset of human NSCLC tumors in which these mutant proteins are expressed, and that such cells may be inhibited by inhibiting the activity of the fusion ALK kinase using a targeted inhibitor, such as WI-131 and/or WI-154

EXAMPLE 5

ALK Fusion Proteins Drive Growth and Survival of Transformed Mammalian Cell Line In order to confirm that expression of one or more of the ALK fusion proteins can transform normal cells into a cancerous phenotype, 3T# cells may be transformed with the cDNA constructs described above (Example 2), which express the EML4-ALK (short and long variants) or TFG-ALK fusion proteins, respectively.

Briefly, cells are maintained in RPMI-1640 medium (Invitrogen) with 10% fetal bovine serum (FBS) (Sigma) and 1.0 ng/ml IL-3 (R&D Systems). Production of retroviral supernatant and transduction is carried out as previously described. See Schwaller et al., *Embo J.* 17(18): 5321-33 (1998). 3T3 cells are transduced with retroviral supernatant containing the MSCV-Neo/EML4-ALK (or TFG-ALK) vector and selected for G418 (1 mg/ml). The ability of transformed cells to grow on soft agar is then accessed by plating transduced cells after the cells are washed three times in PBS. If desired, for dose response curves, cells are treated with siRNA against ALK as described above (see Example 3), and the number of viable cells is determined with the CellTiter 96 AQ$_{ueous}$ One solution cell proliferation assay (Promega). IC$_{50}$ may be calculated with the use of OriginPro 6.1 software (OriginLab). The percentage of apoptotic cells at 48 hours may be determined by flow cytometric analysis of Cleaved-Caspase-3 using an antibody specific for this target (Cell Signaling Technology). Such an analysis would show that the expression of EML4-ALK fusion protein (short or long variant) or TFG-ALK fusion protein can transform the 3T3 cells and confirm survival and growth on soft agar when these cells are driven by the ALK fusion protein, and further that inhibition of ALK expression in the transformed cells leads to decreased viability and increased apoptosis.

EXAMPLE 6

Detection of EML4-ALK Fusion Protein Expression in Human Solid Tumors Using FISH Assay The presence of the EML4-ALK fusion protein (short variant) in human NSCLC tumor samples was detected using a fluorescence in situ hybridization (FISH) assay, as previously described. See, e.g., Verma et al. HUMAN CHROMOSOMES: A MANUAL OF BASIC TECHNIQUES, Pergamon Press, New York, N.Y. (1988). Over 200 paraffin-embedded human NSCLC tumor samples were examined.

An ALK dual color, break-apart rearrangement probe was obtained from Vysis (Vysis, Dowers Grove, Ill., USA) and used according to the manufacturer's instructions with the following modifications. In brief, paraffin embedded tissue sections were re-hydrated and subjected to microwave antigen retrieval in 0.01M Citrate buffer (pH 6.0) for 11 minutes. Sections were digested with Protease (4 mg/ml Pepsin, 2000-3000U/mg) for 25 minutes at 37° C., dehydrated and hybridized with the FISH probe set at 37° C. for 18 hours. After washing, 4',6-diamidino-2-phenylindole (DAPI; mg/ml) in Vectashield mounting medium (Vector Laboratories, Burlingame, Calif.) was applied for nuclear counterstaining.

The ALK rearrangement probe contains two differently labeled probes on opposite sides of the breakpoint of the ALK gene (at nucleotide 3171) in the wild type sequence (SEQ ID NO: 6). When hybridized, the native ALK region will appear as an orange/green fusion signal, while rearrangement at this locus (as occurs in the EML4-ALK deletion mutants) will result in separate orange and green signals. See FIG. 6.

The FISH analysis revealed a relatively low incidence of this short variant EML4-ALK mutation in the sample population studied (one out of 229 samples). However, given the high incidence of NSCLC worldwide (over 151,00 new cases in the U.S. annually, alone), there are expected to be a significant number of patients that harbor this mutant ALK, which patients may benefit from an ALK-inhibiting therapeutic regime.

EXAMPLE 7

Detection of ALK Fusion Protein Expression in Human Solid Tumors Using PCR Assay The presence of one or more ALK fusion proteins in a human solid tumor sample may be also be detected using either genomic or reverse transcriptase (RT) polymerase chain reaction (PCR), previously described. See, e.g., Cools et al., *N. Engl. J. Med.* 348: 1201-1214 (2003). Briefly and by way of example, solid tumor samples may be obtained from a patient having, e.g. NSCLC, using standard techniques. PCR probes against truncated ALK kinase or EML4-ALK fusion protein (short or long variant) or TFG-ALK fusion protein are constructed. RNeasy Mini Kit (Qiagen) may be used to extract RNA from tumor samples. DNA may be extracted with the use of DNeasy Tissue Kit (Qiagen). For RT-PCR, first-strand cDNA is synthesized from, e.g., 2.5 µg of total RNA with the use, for example, of SuperScript™ III first-strand synthesis system (Invitrogen) with oligo (dT)$_{20}$.

Then, the ALK fusion gene is amplified with the use of primer pairs, e.g. EML4-202 and ALK-GSP3 (see Example 2 above). For genomic PCR, amplification of the fusion gene may be performed with the use of Platinum Taq DNA polymerase high fidelity (Invitrogen) with primer pairs, e.g. EML4-202 and ALK-GSP3 (see Example 2, above). Such an analysis will identify a patient having a solid tumor characterized by expression of the truncated ALK kinase (and/or EML4-ALK fusion protein(s) or TFG-ALK fusion protein), which patient is a candidate for treatment using an ALK-inhibiting therapeutic, such as WHI-131 and/or WHI154.

What is claimed is:

1. A method for treating a human subject having a non-small cell lung carcinoma (NSCLC) that expresses a human Echinoderm Microtubule-Associated Protein-Like 4 (EML4)-Anaplastic Lymphoma Kinase (ALK) fusion polypeptide, comprising
administering to the human subject a small molecule that
a) binds to the ATP-binding cleft and b) directly inhibits the kinase activity of the EML4-ALK fusion polypeptide, in an amount effective to treat the NSCLC, wherein i) the EML4-ALK fusion polypeptide comprises an amino acid sequence that is at least 95% identical to an amino acid sequence comprising EML4 amino acid residues 1-222 of SEQ ID NO: 3 and ALK amino acid residues 1116-1383 of SEQ ID NO: 5 and ii) the EML4 amino acid residues are amino-terminal to the ALK amino acid residues.

2. The method of claim 1, wherein the amino acid sequence of the EML4-ALK fusion polypeptide comprises EML4 amino acid residues 1-222 of SEQ ID NO: 3.

3. The method of claim 1, wherein the amino acid sequence of the EML4-ALK fusion polypeptide comprises ALK amino acid residues 1116-1383 of SEQ ID NO: 5.

4. The method of claim 1, wherein the amino acid sequence of the EML4-ALK fusion polypeptide comprises EML4 amino acid residues 1-222 of SEQ ID NO: 3 and the ALK amino acid residues 1116-1383 of SEQ ID NO: 5.

5. The method of claim 1, wherein the EML4-ALK fusion polypeptide comprises an amino acid sequence that is at least 97% identical to an amino acid sequence comprising EML4 amino acid residues 1-222 of SEQ ID NO: 3 and ALK amino acid residues 1116-1383 of SEQ ID NO: 5.

6. The method of claim 5, wherein the amino acid sequence of the EML4-ALK fusion polypeptide comprises EML4 amino acid residues 1-222 of SEQ ID NO: 3.

7. The method of claim 5, wherein the amino acid sequence of the EML4-ALK fusion polypeptide comprises ALK amino acid residues 1116-1383 of SEQ ID NO: 5.

8. The method of claim 1, wherein the EML4-ALK fusion polypeptide comprises an amino acid sequence that is at least 98% identical to an amino acid sequence comprising EML4 amino acid residues 1-222 of SEQ ID NO: 3 and ALK amino acid residues 1116-1383 of SEQ ID NO: 5.

9. The method of claim 8, wherein the amino acid sequence of the EML4-ALK fusion polypeptide comprises EML4 amino acid residues 1-222 of SEQ ID NO: 3.

10. The method of claim 8, wherein the amino acid sequence of the EML4-ALK fusion polypeptide comprises ALK amino acid residues 1116-1383 of SEQ ID NO: 5.

11. The method of claim 1, wherein the EML4-ALK fusion polypeptide comprises an amino acid sequence that is at least 99% identical to an amino acid sequence comprising EML4 amino acid residues 1-222 of SEQ ID NO: 3 and ALK amino acid residues 1116-1383 of SEQ ID NO: 5.

12. The method of claim 11, wherein the amino acid sequence of the EML4-ALK fusion polypeptide comprises EML4 amino acid residues 1-222 of SEQ ID NO: 3.

13. The method of claim 11, wherein the amino acid sequence of the EML4-ALK fusion polypeptide comprises ALK amino acid residues 1116-1383 of SEQ ID NO: 5.

14. A method for treating a human subject having a non-small cell lung carcinoma (NSCLC) that expresses a human Echinoderm Microtubule-Associated Protein-Like 4 (EML4)-Anaplastic Lymphoma Kinase (ALK) fusion polypeptide, wherein the EML4-ALK fusion polypeptide comprises an amino acid sequence that is at least 95% identical to the amino acid sequence of SEQ ID NO: 1, the method comprising
administering to the human subject a small molecule that
a) binds to the ATP-binding cleft and b) directly inhibits the kinase activity of the EML4-ALK fusion polypeptide, in an amount effective to treat the NSCLC.

15. The method of claim 14, wherein the EML4-ALK fusion polypeptide comprises an amino acid sequence that is at least 96% identical to the amino acid sequence of SEQ ID NO: 1.

16. The method of claim 14, wherein the EML4-ALK fusion polypeptide comprises an amino acid sequence that is at least 97% identical to the amino acid sequence of SEQ ID NO: 1.

17. The method of claim 1, wherein the EML4-ALK fusion polypeptide comprises an amino acid sequence that is at least 98% identical to the amino acid sequence of SEQ ID NO: 1.

18. The method of claim 14, wherein the EML4-ALK fusion polypeptide comprises an amino acid sequence that is at least 99% identical to the amino acid sequence of SEQ ID NO: 1.

19. The method of claim 14, wherein the EML4-ALK fusion polypeptide consists of an amino acid sequence that is at least 99% identical to the amino acid sequence of SEQ ID NO: 1.

20. The method of claim 14, wherein the EML4-ALK fusion polypeptide comprises the amino acid sequence of SEQ ID NO: 1.

21. The method of claim 14, wherein the EML4-ALK fusion polypeptide consists of the amino acid sequence of SEQ ID NO: 1.

22. A method for treating a human subject having a non-small cell lung carcinoma (NSCLC) that expresses a human Echinoderm Microtubule-Associated Protein-Like 4 (EML4)-Anaplastic Lymphoma Kinase (ALK) fusion polypeptide, wherein the EML4-ALK fusion polypeptide comprises an amino acid sequence that is at least 95% identical to the amino acid sequence of SEQ ID NO: 18, the method comprising
administering to the human subject a small molecule that
a) binds to the ATP-binding cleft and b) directly inhibits the kinase activity of the EML4-ALK fusion polypeptide, in an amount effective to treat the NSCLC.

23. The method of claim 22, wherein the EML4-ALK fusion polypeptide comprises an amino acid sequence that is at least 96% identical to the amino acid sequence of SEQ ID NO: 18.

24. The method of claim 22, wherein the EML4-ALK fusion polypeptide comprises an amino acid sequence that is at least 97% identical to the amino acid sequence of SEQ ID NO: 18.

25. The method of claim 22, wherein the EML4-ALK fusion polypeptide comprises an amino acid sequence that is at least 98% identical to the amino acid sequence of SEQ ID NO: 18.

26. The method of claim 22, wherein the EML4-ALK fusion polypeptide comprises an amino acid sequence that is at least 99% identical to the amino acid sequence of SEQ ID NO: 18.

27. The method of claim 22, wherein the EML4-ALK fusion polypeptide consists of an amino acid sequence that is at least 99% identical to the amino acid sequence of SEQ ID NO: 18.

28. The method of claim 22, wherein the EML4-ALK fusion polypeptide comprises the amino acid sequence of SEQ ID NO: 18.

29. The method of claim 22, wherein the EML4-ALK fusion polypeptide consists of the amino acid sequence of SEQ ID NO: 18.

* * * * *

SEQUENCE LISTING

<160> NUMBER OF SEQ ID NOS: 30

<210> SEQ ID NO 1
<211> LENGTH: 796
<212> TYPE: PRT
<213> ORGANISM: Homo sapiens

<400> SEQUENCE: 1

```
Met Asp Gly Phe Ala Gly Ser Leu Asp Asp Ser Ile Ser Ala Ala Ser
 1               5                  10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Ala Lys
    210                 215                 220

Met Ser Thr Arg Glu Lys Asn Ser Gln Val Tyr Arg Arg Lys His Gln
225                 230                 235                 240

Glu Leu Gln Ala Met Gln Met Glu Leu Gln Ser Pro Glu Tyr Lys Leu
                245                 250                 255

Ser Lys Leu Arg Thr Ser Thr Ile Met Thr Asp Tyr Asn Pro Asn Tyr
            260                 265                 270

Cys Phe Ala Gly Lys Thr Ser Ser Ile Ser Asp Leu Lys Glu Val Pro
        275                 280                 285

Arg Lys Asn Ile Thr Leu Ile Arg Gly Leu Gly His Gly Ala Phe Gly
    290                 295                 300

Glu Val Tyr Glu Gly Gln Val Ser Gly Met Pro Asn Asp Pro Ser Pro
305                 310                 315                 320

Leu Gln Val Ala Val Lys Thr Leu Pro Glu Val Cys Ser Glu Gln Asp
                325                 330                 335

Glu Leu Asp Phe Leu Met Glu Ala Leu Ile Ile Ser Lys Phe Asn His
            340                 345                 350

Gln Asn Ile Val Arg Cys Ile Gly Val Ser Leu Gln Ser Leu Pro Arg
        355                 360                 365
```

-continued

```
Phe Ile Leu Leu Glu Leu Met Ala Gly Gly Asp Leu Lys Ser Phe Leu
    370                 375                 380

Arg Glu Thr Arg Pro Arg Pro Ser Gln Pro Ser Ser Leu Ala Met Leu
385                 390                 395                 400

Asp Leu Leu His Val Ala Arg Asp Ile Ala Cys Gly Cys Gln Tyr Leu
                405                 410                 415

Glu Glu Asn His Phe Ile His Arg Asp Ile Ala Ala Arg Asn Cys Leu
                420                 425                 430

Leu Thr Cys Pro Gly Pro Gly Arg Val Ala Lys Ile Gly Asp Phe Gly
            435                 440                 445

Met Ala Arg Asp Ile Tyr Arg Ala Ser Tyr Tyr Arg Lys Gly Gly Cys
450                 455                 460

Ala Met Leu Pro Val Lys Trp Met Pro Glu Ala Phe Met Glu Gly
465                 470                 475                 480

Ile Phe Thr Ser Lys Thr Asp Thr Trp Ser Phe Gly Val Leu Leu Trp
                485                 490                 495

Glu Ile Phe Ser Leu Gly Tyr Met Pro Tyr Pro Ser Lys Ser Asn Gln
                500                 505                 510

Glu Val Leu Glu Phe Val Thr Ser Gly Gly Arg Met Asp Pro Pro Lys
            515                 520                 525

Asn Cys Pro Gly Pro Val Tyr Arg Ile Met Thr Gln Cys Trp Gln His
530                 535                 540

Gln Pro Glu Asp Arg Pro Asn Phe Ala Ile Ile Leu Glu Arg Ile Glu
545                 550                 555                 560

Tyr Cys Thr Gln Asp Pro Asp Val Ile Asn Thr Ala Leu Pro Ile Glu
                565                 570                 575

Tyr Gly Pro Leu Val Glu Glu Glu Lys Val Pro Val Arg Pro Lys
                580                 585                 590

Asp Pro Glu Gly Val Pro Pro Leu Leu Val Ser Gln Gln Ala Lys Arg
            595                 600                 605

Glu Glu Glu Arg Ser Pro Ala Ala Pro Pro Pro Leu Pro Thr Thr Ser
            610                 615                 620

Ser Gly Lys Ala Ala Lys Lys Pro Thr Ala Ala Glu Val Ser Val Arg
625                 630                 635                 640

Val Pro Arg Gly Pro Ala Val Glu Gly Gly His Val Asn Met Ala Phe
                645                 650                 655

Ser Gln Ser Asn Pro Pro Ser Glu Leu His Lys Val His Gly Ser Arg
                660                 665                 670

Asn Lys Pro Thr Ser Leu Trp Asn Pro Thr Tyr Gly Ser Trp Phe Thr
            675                 680                 685

Glu Lys Pro Thr Lys Lys Asn Asn Pro Ile Ala Lys Lys Glu Pro His
690                 695                 700

Asp Arg Gly Asn Leu Gly Leu Glu Gly Ser Cys Thr Val Pro Pro Asn
705                 710                 715                 720

Val Ala Thr Gly Arg Leu Pro Gly Ala Ser Leu Leu Leu Glu Pro Ser
                725                 730                 735

Ser Leu Thr Ala Asn Met Lys Glu Val Pro Leu Phe Arg Leu Arg His
                740                 745                 750

Phe Pro Cys Gly Asn Val Asn Tyr Gly Tyr Gln Gln Gln Gly Leu Pro
            755                 760                 765

Leu Glu Ala Ala Thr Ala Pro Gly Ala Gly His Ile Glu Asp Thr Ile
770                 775                 780

Leu Lys Ser Lys Asn Ser Met Asn Gln Pro Gly Pro
```

<210> SEQ ID NO 2
<211> LENGTH: 2391
<212> TYPE: DNA
<213> ORGANISM: Homo sapiens

<400> SEQUENCE: 2

| | | | | | | |
|---|---|---|---|---|---|---|
| atggacggtt | tcgccggcag | tctcgatgat | agtatttctg | ctgcaagtac | ttctgatgtt | 60 |
| caagatcgcc | tgtcagctct | tgagtcacga | gttcagcaac | aagaagatga | aatcactgtg | 120 |
| ctaaaggcgg | ctttggctga | tgttttgagg | cgtcttgcaa | tctctgaaga | tcatgtggcc | 180 |
| tcagtgaaaa | aatcagtctc | aagtaaaggc | caaccaagcc | ctcgagcagt | tattcccatg | 240 |
| tcctgtataa | ccaatggaag | tggtgcaaac | agaaaaccaa | gtcataccag | tgctgtctca | 300 |
| attgcaggaa | aagaaactct | ttcatctgct | gctaaaagtg | gtacagaaaa | aaagaaagaa | 360 |
| aaaccacaag | acagagaga | aaaaaagag | gaatctcatt | ctaatgatca | aagtccacaa | 420 |
| attcgagcat | caccttctcc | ccagccctct | tcacaacctc | tccaaataca | cagacaaact | 480 |
| ccagaaagca | agaatgctac | tcccaccaaa | agcataaaac | gaccatcacc | agctgaaaag | 540 |
| tcacataatt | cttgggaaaa | ttcagatgat | agccgtaata | aattgtcgaa | ataccttca | 600 |
| acacccaaat | taataccaaa | agttaccaaa | actgcagaca | agcataaaga | tgtcatcatc | 660 |
| aaccaagcaa | aaatgtcaac | tcgcgaaaaa | aacagccaag | tgtaccgccg | aagcaccag | 720 |
| gagctgcaag | ccatgcagat | ggagctgcag | agccctgagt | acaagctgag | caagctccgc | 780 |
| acctcgacca | tcatgaccga | ctacaacccc | aactactgct | tgctggcaa | gacctcctcc | 840 |
| atcagtgacc | tgaaggaggt | gccgcggaaa | acatcaccc | tcattcgggg | tctgggccat | 900 |
| ggcgcctttg | ggaggtgta | tgaaggcag | gtgtccggaa | tgcccaacga | cccaagcccc | 960 |
| ctgcaagtgg | ctgtgaagac | gctgcctgaa | gtgtgctctg | aacaggacga | actggatttc | 1020 |
| ctcatggaag | ccctgatcat | cagcaaattc | aaccaccaga | acattgttcg | ctgcattggg | 1080 |
| gtgagcctgc | aatccctgcc | ccggttcatc | ctgctggagc | tcatggcggg | gggagacctc | 1140 |
| aagtccttcc | tccgagagac | ccgccctcgc | ccgagccagc | cctcctccct | ggccatgctg | 1200 |
| gaccttctgc | acgtggctcg | ggacattgcc | tgtggctgtc | agtatttgga | ggaaaaccac | 1260 |
| ttcatccacc | gagacattgc | tgccagaaac | tgcctcttga | cctgtccagg | ccctggaaga | 1320 |
| gtggccaaga | ttggagactt | cgggatggcc | cgagacatct | acagggcgag | ctactataga | 1380 |
| aagggaggct | gtgccatgct | gccagttaag | tggatgcccc | cagaggcctt | catgaagga | 1440 |
| atattcactt | ctaaaacaga | cacatggtcc | tttggagtgc | tgctatggga | aatcttttct | 1500 |
| cttggatata | tgccataccc | cagcaaaagc | aaccaggaag | ttctggagtt | tgtcaccagt | 1560 |
| ggaggccgga | tggacccacc | caagaactgc | cctgggcctg | tataccggat | aatgactcag | 1620 |
| tgctggcaac | atcagcctga | agacaggccc | aactttgcca | tcattttgga | gaggattgaa | 1680 |
| tactgcaccc | aggacccgga | tgtaatcaac | accgctttgc | cgatagaata | tggtccactt | 1740 |
| gtggaagagg | aagagaaagt | gcctgtgagg | cccaaggacc | ctgagggggt | tcctcctctc | 1800 |
| ctggtctctc | aacaggcaaa | acgggaggag | gagcgcagcc | cagctgcccc | accacctctg | 1860 |
| cctaccacct | cctctggcaa | ggctgcaaag | aaacccacag | ctgcagaggt | ctctgttcga | 1920 |
| gtccctagag | ggcggccgt | ggaagggga | cacgtgaata | tggcattctc | tcagtccaac | 1980 |
| cctccttcgg | agttgcacaa | ggtccacgga | tccagaaaca | gcccaccag | cttgtggaac | 2040 |
| ccaacgtacg | gctcctggtt | tacagagaaa | cccaccaaaa | agaataatcc | tatagcaaag | 2100 |

```
aaggagccac acgacagggg taacctgggg ctggagggaa gctgtactgt cccacctaac    2160
gttgcaactg ggagacttcc gggggcctca ctgctcctag agccctcttc gctgactgcc    2220
aatatgaagg aggtacctct gttcaggcta cgtcacttcc cttgtgggaa tgtcaattac    2280
ggctaccagc aacagggctt gcccttagaa gccgctactg ccctggagc tggtcattac     2340 gaggatacca ttctgaaaag caagaatagc atgaaccagc tgggccctg a              2391

<210> SEQ ID NO 3
<211> LENGTH: 981
<212> TYPE: PRT
<213> ORGANISM: Homo sapiens

<400> SEQUENCE: 3
```

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
                20                  25                  30

Gln Gln Glu Asp Glu Ile Thr Val Leu Lys Ala Ala Leu Ala Asp Val
            35                  40                  45

Leu Arg Arg Leu Ala Ile Ser Glu Asp His Val Ala Ser Val Lys Lys
50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
                100                 105                 110

Ser Gly Thr Glu Lys Lys Lys Glu Lys Pro Gln Gly Gln Arg Glu Lys
            115                 120                 125

Lys Glu Glu Ser His Ser Asn Asp Gln Ser Pro Gln Ile Arg Ala Ser
130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
                180                 185                 190

Asn Lys Leu Ser Lys Ile Pro Ser Thr Pro Lys Leu Ile Pro Lys Val
            195                 200                 205

Thr Lys Thr Ala Asp Lys His Lys Asp Val Ile Ile Asn Gln Glu Gly
            210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
                260                 265                 270

Arg Ala Asn Val Tyr Leu Leu Pro Thr Gly Glu Ile Val Tyr Phe Ile
            275                 280                 285

Ala Ser Val Val Val Leu Phe Asn Tyr Glu Glu Arg Thr Gln Arg His
            290                 295                 300

Tyr Leu Gly His Thr Asp Cys Val Lys Cys Leu Ala Ile His Pro Asp
305                 310                 315                 320

-continued

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
                340                 345                 350

Thr Leu Gln Ile Ile Gly Leu Gly Thr Phe Glu Arg Gly Val Gly Cys
                355                 360                 365

Leu Asp Phe Ser Lys Ala Asp Ser Gly Val His Leu Cys Val Ile Asp
                370                 375                 380

Asp Ser Asn Glu His Met Leu Thr Val Trp Asp Gln Lys Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
                420                 425                 430

Ile Phe Phe Trp Thr Trp Ser Gly Asn Ser Leu Thr Arg Lys Gln Gly
                435                 440                 445

Ile Phe Gly Lys Tyr Glu Lys Pro Lys Phe Val Gln Cys Leu Ala Phe
                450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
                485                 490                 495

Gly Val Tyr Gln Ile Ser Lys Gln Ile Lys Ala His Asp Gly Ser Val
                500                 505                 510

Phe Thr Leu Cys Gln Met Arg Asn Gly Met Leu Leu Thr Gly Gly Gly
                515                 520                 525

Lys Asp Arg Lys Ile Ile Leu Trp Asp His Asp Leu Asn Pro Glu Arg
                530                 535                 540

Glu Ile Glu Val Pro Asp Gln Tyr Gly Thr Ile Arg Ala Val Ala Glu
545                 550                 555                 560

Gly Lys Ala Asp Gln Phe Leu Val Gly Thr Ser Arg Asn Phe Ile Leu
                565                 570                 575

Arg Gly Thr Phe Asn Asp Gly Phe Gln Ile Glu Val Gln Gly His Thr
                580                 585                 590

Asp Glu Leu Trp Gly Leu Ala Thr His Pro Phe Lys Asp Leu Leu Leu
                595                 600                 605

Thr Cys Ala Gln Asp Arg Gln Val Cys Leu Trp Asn Ser Met Glu His
                610                 615                 620

Arg Leu Glu Trp Thr Arg Leu Val Asp Glu Pro Gly His Cys Ala Asp
625                 630                 635                 640

Phe His Pro Ser Gly Thr Val Val Ala Ile Gly Thr His Ser Gly Arg
                645                 650                 655

Trp Phe Val Leu Asp Ala Glu Thr Arg Asp Leu Val Ser Ile His Thr
                660                 665                 670

Asp Gly Asn Glu Gln Leu Ser Val Met Arg Tyr Ser Ile Asp Gly Thr
                675                 680                 685

Phe Leu Ala Val Gly Ser His Asp Asn Phe Ile Tyr Leu Tyr Val Val
                690                 695                 700

Ser Glu Asn Gly Arg Lys Tyr Ser Arg Tyr Gly Arg Cys Thr Gly His
705                 710                 715                 720

Ser Ser Tyr Ile Thr His Leu Asp Trp Ser Pro Asp Asn Lys Tyr Ile
                725                 730                 735

Met Ser Asn Ser Gly Asp Tyr Glu Ile Leu Tyr Trp Asp Ile Pro Asn

```
                    740              745              750
Gly Cys Lys Leu Ile Arg Asn Arg Ser Asp Cys Lys Asp Ile Asp Trp
            755                  760                  765

Thr Thr Tyr Thr Cys Val Leu Gly Phe Gln Val Phe Gly Val Trp Pro
        770                  775                  780

Glu Gly Ser Asp Gly Thr Asp Ile Asn Ala Leu Val Arg Ser His Asn
785                  790                  795                  800

Arg Lys Val Ile Ala Val Ala Asp Asp Phe Cys Lys Val His Leu Phe
                805                  810                  815

Gln Tyr Pro Cys Ser Lys Ala Lys Ala Pro Ser His Lys Tyr Ser Ala
            820                  825                  830

His Ser Ser His Val Thr Asn Val Ser Phe Thr His Asn Asp Ser His
        835                  840                  845

Leu Ile Ser Thr Gly Gly Lys Asp Met Ser Ile Ile Gln Trp Lys Leu
    850                  855                  860

Val Glu Lys Leu Ser Leu Pro Gln Asn Glu Thr Val Ala Asp Thr Thr
865                  870                  875                  880

Leu Thr Lys Ala Pro Val Ser Ser Thr Glu Ser Val Ile Gln Ser Asn
                885                  890                  895

Thr Pro Thr Pro Pro Ser Gln Pro Leu Asn Glu Thr Ala Glu Glu
            900                  905                  910

Glu Ser Arg Ile Ser Ser Ser Pro Thr Leu Leu Glu Asn Ser Leu Glu
        915                  920                  925

Gln Thr Val Glu Pro Ser Glu Asp His Ser Glu Glu Glu Ser Glu Glu
    930                  935                  940

Gly Ser Gly Asp Leu Gly Glu Pro Leu Tyr Glu Glu Pro Cys Asn Glu
945                  950                  955                  960

Ile Ser Lys Glu Gln Ala Lys Ala Thr Leu Leu Glu Asp Gln Gln Asp
                965                  970                  975

Pro Ser Pro Ser Ser
            980

<210> SEQ ID NO 4
<211> LENGTH: 5301
<212> TYPE: DNA
<213> ORGANISM: Homo sapiens

<400> SEQUENCE: 4
atggacggtt tcgccggcag tctcgatgat agtatttctg ctgcaagtac ttctgatgtt     60
caagatcgcc tgtcagctct tgagtcacga gttcagcaac aagaagatga aatcactgtg    120
ctaaaggcgg ctttggctga tgttttgagg cgtcttgcaa tctctgaaga tcatgtggcc    180
tcagtgaaaa aatcagtctc aagtaaaggc aaccaagcc tcgagcagt tattcccatg     240 tcctgtataa ccaatggaag tggtgcaaac agaaaaccaa gtcataccag tgctgtctca    300
attgcaggaa agaaactct ttcatctgct gctaaaagtg gtacagaaaa aaagaaagaa    360
aaaccacaag gacagagaga aaaaaaagag gaatctcatt ctaatgatca agtccacaa    420 attcgagcat caccttctcc ccagccctct tcacaacctc tccaaataca cagacaaact    480
ccagaaagca gaatgctac tcccaccaaa agcataaaac gaccatcacc agctgaaaag    540
tcacataatt cttgggaaaa ttcagatgat agccgtaata aattgtcgaa ataccttca    600 acacccaaat taataccaaa agttaccaaa actgcagaca agcataaaga tgtcatcatc    660
aaccaagaag gagaatatat taaaatgtttt atgcgcggtc ggccaattac catgttcatt    720
```

```
ccttccgatg ttgacaacta tgatgacatc agaacggaac tgcctcctga gaagctcaaa    780
ctggagtggg catatggtta tcgaggaaag gactgtagag ctaatgttta ccttcttccg    840
accgggaaaa tagtttattt cattgcatca gtagtagtac tatttaatta tgaggagaga    900
actcagcgac actacctggg ccatacagac tgtgtgaaat gccttgctat acatcctgac    960
aaaattagga ttgcaactgg acagatagct ggcgtggata agatggaag gcctctacaa    1020 ccccacgtca gagtgtggga ttctgttact ctatccacac tgcagattat tggacttggc    1080
acttttgagc gtggagtagg atgcctggat ttttcaaaag cagattcagg tgttcattta    1140
tgtgttattg atgactccaa tgagcatatg cttactgtat gggactggca gaagaaagca    1200
aaaggagcag aaataaagac aacaaatgaa gttgttttgg ctgtggagtt tcacccaaca    1260
gatgcaaata ccataattac atgcggtaaa tctcatattt tcttctggac ctggagcggc    1320
aattcactaa caagaaaaca gggaattttt gggaaatatg aaaagccaaa atttgtgcag    1380
tgtttagcat tcttgggaa tggagatgtt cttactggag actcaggtgg agtcatgctt    1440
atatggagca aaactactgt agagcccaca cctgggaaag gacctaaagg tgtatatcaa    1500
atcagcaaac aaatcaaagc tcatgatggc agtgtgttca cactttgtca gatgagaaat    1560
gggatgttat aactggagg agggaaagac agaaaaataa ttctgtggga tcatgatctg    1620
aatcctgaaa gagaaataga ggttcctgat cagtatggca caatcagagc tgtagcagaa    1680
ggaaaggcag atcaatttt agtaggcaca tcacgaaact ttattttacg aggaacattt    1740
aatgatggct ccaaataga agtacagggt catacagatg agctttgggg tcttgccaca    1800
catcccttca aagatttgct cttgacatgt gctcaggaca ggcaggtgtg cctgtggaac    1860
tcaatggaac acaggctgga atggaccagg ctggtagatg aaccaggaca ctgtgcagat    1920
tttcatccaa gtggcacagt ggtggccata ggaacgcact caggcaggtg gtttgttctg    1980
gatgcagaaa ccagagatct agtttctatc cacacagacg ggaatgaaca gctctctgtg    2040
atgcgctact caatagatgg taccttcctg gctgtaggat ctcatgacaa ctttatttac    2100
ctctatgtag tctctgaaaa tggaagaaaa tatagcagat atggaaggtg cactggacat    2160
tccagctaca tcacacacct tgactggtcc ccagacaaca agtatataat gtctaactcg    2220
ggagactatg aaatattgta ctgggacatt ccaaatggct gcaaactaat caggaatcga    2280
tcggattgta aggacattga ttggacgaca tatacctgtg tgctaggatt tcaagtattt    2340
ggtgtctggc cagaaggatc tgatgggaca gatatcaatg cactggtgcg atcccacaat    2400
agaaaggtga tagctgttgc cgatgacttt tgtaaagtcc atctgtttca gtatccctgc    2460
tccaaagcaa aggctcccag tcacaagtac agtgcccaca gcagccatgt caccaatgtc    2520
agttttactc acaatgacag tcacctgata tcaactggtg aaaagacat gagcatcatt    2580 cagtggaaac ttgtggaaaa gttatctttg cctcagaatg agactgtagc ggatactact    2640
ctaaccaaag cccccgtctc ttccactgaa agtgtcatcc aatctaatac tcccacaccg    2700
cctccttctc agcccttaaa tgagacagct gaagaggaaa gtagaataag cagttctccc    2760
acacttctgg agaacagcct ggaacaaact gtgggccaag tgaagaccac agcgaggagg    2820
agagtgaaga gggcagcgga gaccttggtg agcctcttta tgaagagcca tgcaacgaga    2880
taagcaagga gcaggccaaa gccacccttc tggaggacca gcaagaccct tcgccctcgt    2940
cctaacaccc tggcttcagt gcaactcttt tccttcagct gcatgtgatt ttgtgataaa    3000
gttcaggtaa caggatgggc agtgatggag aatcactgtt gattgagatt ttggtttcca    3060
tgtgatttgt tttcttcaat agtcttattt tcagtctctc aaatacagcc aacttaaagt    3120
```

```
tttagtttgg tgtttattga aaattaacca aacttaatac taggagaaga ctgaatcatt   3180
aatgatgtct cacaaattac tgtgtaccta agtggtgtga tgtaaatact ggaaacaaaa   3240
acagcagttg cattgatttt gaaaacaaac ccccttgtta tctgaacatg ttttcttcag   3300
gaacaaccag aggtatcaca aacactgtta ctcatctact ggctcagact gtactacttt   3360
tttttttttt tttcctgaaa aagaaaccag aaaaaaatgt actcttactg agatacccctc  3420 tcaccccaaa tgtgtaatgg aaaattttta attaagaaaa acttcagttt tgccaagtgc   3480
aatggtgttg ccttctttaa aaaatgccgt tttcttacac taccagtgga tgtccagaca   3540
tgctcttagt ctactagaga ggtgctgcct tttctaagtc ataatgagga acagtcccctt  3600 aatttcttgt gtgcaactct gttttatcct agaactaaga gagcattggt ttgttaaaga   3660
gctttcaatg tatattaaaa ccttcaatac tcagaaatga tggattcctc caaggagtcc   3720
tttactagcc taaacattct caaatgtttg agattcaagt gaatggaagg aaaaccacat   3780
gcctttaaaa ctaaactgta ataattacct ggctaatttc agctaagcct tcatcataat   3840
ttgttccctc agtaatagga gaaatataaa tacagtaagt ttagattatt gaattggtgc   3900
ttgaaattta ttggttttgt tgtaatttta tacagattat atgagggata agatactcat   3960
caaattgcaa attctttttt ttacagaagt gtgggtaaca gtcacagcag ttttttttac   4020
caacagcata cttaacagac ttgctgtgta gcagttttt tctggtggag ttgctgtaag    4080
tcttgtaagt ctaatgtggc tatcctactc ttttgggcaa tgcatgtatt atgcattgga   4140
aaggtatttt ttttaagttc tgttggctag ctatggtttt cagtacattt cctactttaa   4200
gagtaattac tgacaaatat gtatttccta tatgtttata ctttgattat aaaaaagtat   4260
tttgttttga ttttttaact tgctgcattg ttttgatact ttctattttt ttggtcaaat   4320
catgtttaga aactttggat gagttaagaa gtcttaagta tgcaggcgtt tacgtgattg   4380
tgccattcca aagtgcatca gaactgtcat tcccttctaa tatcttctca ggagtaaatac  4440 aaatcaggta tttcatcatc atttggtaat atgaaaactc cagtgaactc ccaaggacat   4500
ttacaacatt tatattcaca cgctgtatgg aagggtgtgg gtgtgtgtga aggggcgagt   4560
ggagacactg tgtgtatctc tagataagaa gatatgcacc acgttgaaaa tactcagtgt   4620
agatctctat gtgtataggt atctgtatat cttttccttt tgtttacaact gttaaaaaac   4680 ctcaaaatag ttctcttcaa aagaagagag attccaagca acccatcttt cttcagtatg   4740
tatgttctgt acatacttat cggagcgcgc cagtaagtat caggcatata tatctgtctg   4800
ttagcaatga ttattacatc atcagatcag catgtgctat actccctgca agaaatatac   4860
tgacatgaac aggcagttct tggagaagaa agagcatttc tttaagtacc tggggaatac   4920
agctctcagt gatcagcagg gagtttattt gaggacatca gtcacctttg gggttgccat   4980
gtacaatgag atttataatc atgatactct tcggtggtag tttcaaaaga cactactaat   5040
acgcaggaag cgtccagcta tttaatgctg caactactg tttaatggtc agttaaatct    5100
gtgataatgg ttggaagtgg gtggggttat gaaattgtag atgttttag aaaaacttgt    5160 gaatgaaaat gaatccaagt gtttcatgtg aagatgttga gccattgcta tcatgcattc   5220
ctgtctcatg gcagaaaatt ttgaagatta aaaaataaaa taatcaaaat gtttcctctt   5280
tctaaaaaaa aaaaaaaaaa a                                             5301

<210> SEQ ID NO 5
<211> LENGTH: 1590
<212> TYPE: PRT
```

<213> ORGANISM: Homo sapiens

<400> SEQUENCE: 5

```
Met Gly Ala Ile Gly Leu Leu Trp Leu Leu Pro Leu Leu Leu Ser Thr
 1               5                  10                  15

Ala Ala Val Gly Ser Gly Met Gly Thr Gly Gln Arg Ala Gly Ser Pro
            20                  25                  30

Ala Ala Gly Ser Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
 50                  55                  60

Arg Val Tyr Ala Arg Asp Leu Leu Leu Pro Pro Ser Ser Ser Glu Leu
 65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
370                 375                 380

Gly Trp Thr Val Leu Gln Gly Arg Ile Gly Arg Pro Asp Asn Pro Phe
385                 390                 395                 400
```

-continued

Arg Val Ala Leu Glu Tyr Ile Ser Ser Gly Asn Arg Ser Leu Ser Ala
                405                 410                 415
Val Asp Phe Phe Ala Leu Lys Asn Cys Ser Glu Gly Thr Ser Pro Gly
            420                 425                 430
Ser Lys Met Ala Leu Gln Ser Ser Phe Thr Cys Trp Asn Gly Thr Val
            435                 440                 445
Leu Gln Asn Phe Glu Asp Gly Phe Cys Gly Trp Thr Gln Gly Thr Leu
450                 455                 460
Ser Pro His Thr Pro Gln Trp Gln Val Arg Thr Leu Lys Asp Ala Arg
465                 470                 475                 480
Phe Gln Asp His Gln Asp His Ala Leu Leu Ser Thr Thr Asp Val
                485                 490                 495
Pro Ala Ser Glu Ser Ala Thr Val Thr Ser Ala Thr Phe Pro Ala Pro
            500                 505                 510
Ile Lys Ser Ser Pro Cys Glu Leu Arg Met Ser Trp Leu Ile Arg Gly
            515                 520                 525
Val Leu Arg Gly Asn Val Ser Leu Val Leu Val Glu Asn Lys Thr Gly
            530                 535                 540
Lys Glu Gln Gly Arg Met Val Trp His Val Ala Ala Tyr Glu Gly Leu
545                 550                 555                 560
Ser Leu Trp Gln Trp Met Val Leu Pro Leu Leu Asp Val Ser Asp Arg
                565                 570                 575
Phe Trp Leu Gln Met Val Ala Trp Trp Gly Gln Gly Ser Arg Ala Ile
                580                 585                 590
Val Ala Phe Asp Asn Ile Ser Ile Ser Leu Asp Cys Tyr Leu Thr Ile
            595                 600                 605
Ser Gly Glu Asp Lys Ile Leu Gln Asn Thr Ala Pro Lys Ser Arg Asn
610                 615                 620
Leu Phe Glu Arg Asn Pro Asn Lys Glu Leu Lys Pro Gly Glu Asn Ser
625                 630                 635                 640
Pro Arg Gln Thr Pro Ile Phe Asp Pro Thr Val His Trp Leu Phe Thr
                645                 650                 655
Thr Cys Gly Ala Ser Gly Pro His Gly Pro Thr Gln Ala Gln Cys Asn
            660                 665                 670
Asn Ala Tyr Gln Asn Ser Asn Leu Ser Val Glu Val Gly Ser Glu Gly
            675                 680                 685
Pro Leu Lys Gly Ile Gln Ile Trp Lys Val Pro Ala Thr Asp Thr Tyr
            690                 695                 700
Ser Ile Ser Gly Tyr Gly Ala Ala Gly Gly Lys Gly Gly Lys Asn Thr
705                 710                 715                 720
Met Met Arg Ser His Gly Val Ser Val Leu Gly Ile Phe Asn Leu Glu
                725                 730                 735
Lys Asp Asp Met Leu Tyr Ile Leu Val Gly Gln Gln Gly Glu Asp Ala
                740                 745                 750
Cys Pro Ser Thr Asn Gln Leu Ile Gln Lys Val Cys Ile Gly Glu Asn
            755                 760                 765
Asn Val Ile Glu Glu Ile Arg Val Asn Arg Ser Val His Glu Trp
            770                 775                 780
Ala Gly Gly Gly Gly Gly Gly Gly Ala Thr Tyr Val Phe Lys Met
785                 790                 795                 800
Lys Asp Gly Val Pro Val Pro Leu Ile Ile Ala Ala Gly Gly Gly
                805                 810                 815
Arg Ala Tyr Gly Ala Lys Thr Asp Thr Phe His Pro Glu Arg Leu Glu

```
                820                 825                 830
Asn Asn Ser Ser Val Leu Gly Leu Asn Gly Asn Ser Gly Ala Ala Gly
            835                 840                 845

Gly Gly Gly Gly Trp Asn Asp Asn Thr Ser Leu Leu Trp Ala Gly Lys
            850                 855                 860

Ser Leu Gln Glu Gly Ala Thr Gly Gly His Ser Cys Pro Gln Ala Met
865                 870                 875                 880

Lys Lys Trp Gly Trp Glu Thr Arg Gly Phe Gly Gly Gly Gly
                885                 890                 895

Gly Cys Ser Ser Gly Gly Gly Gly Gly Tyr Ile Gly Gly Asn Ala
            900                 905                 910

Ala Ser Asn Asn Asp Pro Glu Met Asp Gly Glu Asp Gly Val Ser Phe
            915                 920                 925

Ile Ser Pro Leu Gly Ile Leu Tyr Thr Pro Ala Leu Lys Val Met Glu
            930                 935                 940

Gly His Gly Glu Val Asn Ile Lys His Tyr Leu Asn Cys Ser His Cys
945                 950                 955                 960

Glu Val Asp Glu Cys His Met Asp Pro Glu Ser His Lys Val Ile Cys
            965                 970                 975

Phe Cys Asp His Gly Thr Val Leu Ala Glu Asp Gly Val Ser Cys Ile
            980                 985                 990

Val Ser Pro Thr Pro Glu Pro His Leu Pro Leu Ser Leu Ile Leu Ser
            995                 1000                1005

Val Val Thr Ser Ala Leu Val Ala Ala Leu Val Leu Ala Phe Ser Gly
        1010                1015                1020

Ile Met Ile Val Tyr Arg Arg Lys His Gln Glu Leu Gln Ala Met Gln
1025                1030                1035                1040

Met Glu Leu Gln Ser Pro Glu Tyr Lys Leu Ser Lys Leu Arg Thr Ser
                1045                1050                1055

Thr Ile Met Thr Asp Tyr Asn Pro Asn Tyr Cys Phe Ala Gly Lys Thr
            1060                1065                1070

Ser Ser Ile Ser Asp Leu Lys Glu Val Pro Arg Lys Asn Ile Thr Leu
        1075                1080                1085

Ile Arg Gly Leu Gly His Gly Ala Phe Gly Glu Val Tyr Glu Gly Gln
        1090                1095                1100

Val Ser Gly Met Pro Asn Asp Pro Ser Pro Leu Gln Val Ala Val Lys
1105                1110                1115                1120

Thr Leu Pro Glu Val Cys Ser Glu Gln Asp Glu Leu Asp Phe Leu Met
            1125                1130                1135

Glu Ala Leu Ile Ile Ser Lys Phe Asn His Gln Asn Ile Val Arg Cys
            1140                1145                1150

Ile Gly Val Ser Leu Gln Ser Leu Pro Arg Phe Ile Leu Leu Glu Leu
        1155                1160                1165

Met Ala Gly Gly Asp Leu Lys Ser Phe Leu Arg Glu Thr Arg Pro Arg
            1170                1175                1180

Pro Ser Gln Pro Ser Ser Leu Ala Met Leu Asp Leu Leu His Val Ala
1185                1190                1195                1200

Arg Asp Ile Ala Cys Gly Cys Gln Tyr Leu Glu Glu Asn His Phe Ile
            1205                1210                1215

His Arg Asp Ile Ala Ala Arg Asn Cys Leu Leu Thr Cys Pro Gly Pro
            1220                1225                1230

Gly Arg Val Ala Lys Ile Gly Asp Phe Gly Met Ala Arg Asp Ile Tyr
        1235                1240                1245
```

```
Arg Ala Ser Tyr Tyr Arg Lys Gly Gly Cys Ala Met Leu Pro Val Lys
    1250                1255                1260

Trp Met Pro Pro Glu Ala Phe Met Glu Gly Ile Phe Thr Ser Lys Thr
1265                1270                1275                1280

Asp Thr Trp Ser Phe Gly Val Leu Leu Trp Glu Ile Phe Ser Leu Gly
                1285                1290                1295

Tyr Met Pro Tyr Pro Ser Lys Ser Asn Gln Glu Val Leu Glu Phe Val
            1300                1305                1310

Thr Ser Gly Gly Arg Met Asp Pro Pro Lys Asn Cys Pro Gly Pro Val
        1315                1320                1325

Tyr Arg Ile Met Thr Gln Cys Trp Gln His Gln Pro Glu Asp Arg Pro
    1330                1335                1340

Asn Phe Ala Ile Ile Leu Glu Arg Ile Glu Tyr Cys Thr Gln Asp Pro
1345                1350                1355                1360

Asp Val Ile Asn Thr Ala Leu Pro Ile Glu Tyr Gly Pro Leu Val Glu
                1365                1370                1375

Glu Glu Glu Lys Val Pro Val Arg Pro Lys Asp Pro Glu Gly Val Pro
            1380                1385                1390

Pro Leu Leu Val Ser Gln Gln Ala Lys Arg Glu Glu Glu Arg Ser Pro
        1395                1400                1405

Ala Ala Pro Pro Pro Leu Pro Thr Thr Ser Ser Gly Lys Ala Ala Lys
    1410                1415                1420

Lys Pro Thr Ala Ala Glu Val Ser Val Arg Val Pro Arg Gly Pro Ala
1425                1430                1435                1440

Val Glu Gly Gly His Val Asn Met Ala Phe Ser Gln Ser Asn Pro Pro
                1445                1450                1455

Ser Glu Leu His Lys Val His Gly Ser Arg Asn Lys Pro Thr Ser Leu
            1460                1465                1470

Trp Asn Pro Thr Tyr Gly Ser Trp Phe Thr Glu Lys Pro Thr Lys Lys
        1475                1480                1485

Asn Asn Pro Ile Ala Lys Lys Glu Pro His Asp Arg Gly Asn Leu Gly
    1490                1495                1500

Leu Glu Gly Ser Cys Thr Val Pro Pro Asn Val Ala Thr Gly Arg Leu
1505                1510                1515                1520

Pro Gly Ala Ser Leu Leu Leu Glu Pro Ser Ser Leu Thr Ala Asn Met
                1525                1530                1535

Lys Glu Val Pro Leu Phe Arg Leu Arg His Phe Pro Cys Gly Asn Val
            1540                1545                1550

Asn Tyr Gly Tyr Gln Gln Gln Gly Leu Pro Leu Glu Ala Ala Thr Ala
        1555                1560                1565

Pro Gly Ala Gly His Tyr Glu Asp Thr Ile Leu Lys Ser Lys Asn Ser
    1570                1575                1580

Met Asn Gln Pro Gly Pro
1585                1590

<210> SEQ ID NO 6
<211> LENGTH: 5293
<212> TYPE: DNA
<213> ORGANISM: Homo sapiens

<400> SEQUENCE: 6
agagacttgc gcgcacgcac agtcctctgg agatcaggtg aaggagccg ctgggtacca      60 aggactgttc agagcctctt cccatctcgg ggagagcgaa gggtgaggct gggcccggag    120
```

```
agcagtgtaa acggcctcct ccggcgggat gggagccatc gggctcctgt ggctgctgcc      180
gctgctgctt tccacggcag ctgtgggctc cgggatgggg accggccagc gcgcgggctc      240
cccagctgcg gggccgccgc tgcagccccg ggagccactc agctactcgc gcctgcagag      300
gaagagtctg gcagttgact tcgtggtgcc ctcgctcttc cgtgtctacg cccgggacct      360
actgctgcca ccatcctcct cggagctgaa ggctggcagg cccgaggccc gcggctcgct      420
agctctggac tgcgccccgc tgctcaggtt gctggggccg cgccggggg tctcctggac       480 cgccggttca ccagccccgg cagaggcccg gacgctgtcc agggtgctga agggcggctc      540
cgtgcgcaag ctccggcgtg ccaagcagtt ggtgctggag ctgggcgagg aggcgatctt      600
ggagggttgc gtcgggcccc ccggggaggc ggctgtgggg ctgctccagt tcaatctcag      660
cgagctgttc agttggtgga ttcgccaagg cgaagggcga ctgaggatcc gcctgatgcc      720
cgagaagaag gcgtcggaag tgggcagaga gggaaggctg tccgcggcaa ttcgcgcctc      780
ccagccccgc cttctcttcc agatcttcgg gactggtcat agctccttgg aatcaccaac      840
aaacatgcct tctccttctc ctgattattt tacatggaat ctcacctgga taatgaaaga      900
ctccttccct ttcctgtctc atcgcagccg atatggtctg gagtgcagct ttgacttccc      960
ctgtgagctg gagtattccc ctccactgca tgacctcagg aaccagagct ggtcctggcg     1020
ccgcatcccc tccgaggagg cctcccagat ggacttgctg gatgggcctg ggcagagcg     1080 ttctaaggag atgcccagag gctcctttct ccttctcaac acctcagctg actccaagca     1140
caccatcctg agtccgtgga tgaggagcag cagtgagcac tgcacactgg ccgtctcggt     1200
gcacaggcac ctgcagccct ctggaaggta cattgcccag ctgctgcccc acaacgaggc     1260
tgcaagagag atcctcctga tgcccactcc agggaagcat ggttggacag tgctccaggg     1320
aagaatcggc cgtccagaca acccatttcg agtggccctg aatacatct ccagtggaaa      1380 ccgcagcttg tctgcagtgg acttctttgc cctgaagaac tgcagtgaag aacatccccc     1440
aggctccaag atgcccctgc agagctcctt cacttgttgg aatgggacag tcctccagct     1500
tgggcaggcc tgtgacttcc accaggactg tgcccaggga aagatgaga gccagatgtg      1560 ccggaaactg cctgtggggt tttactgcaa ctttgaagat ggcttctgtg gctgacccca    1620
aggcacactg tcaccccaca ctcctcagtg gcaggtcagg accctaaagg atgcccggtt     1680
ccaggaccac caagaccatg ctctattgct cagtaccact gatgtccccg cttctgaaag     1740
tgctacagtg accagtgcta cgtttcctgc accgatcaag agctctccat gtgagctccg     1800
aatgtcctgg ctcattcgtg gagtcttgag gggaaacgtg tccttggtgc tagtggagaa     1860
caaaaccggg aaggagcaag gcaggatggt ctggcatgtc gccgcctatg aaggcttgag    1920
cctgtggcag tggatggtgt tgcctctcct cgatgtgtct gacaggttct ggctgcagat    1980
ggtcgcatgg tgggacaag gatccagagc catcgtggct tttgacaata tctccatcag     2040
cctggactgc tacctcacca ttagcggaga ggacaagatc ctgcagaata cagcacccaa    2100
atcaagaaac ctgtttgaga gaaacccaaa caaggagctg aaacccgggg aaaattcacc    2160
aagacagacc cccatctttg accctacagt tcattggctg ttcaccacat gtggggccag    2220
cgggccccat ggccccaccc aggcacagtg caacaacgcc taccagaact ccaacctgag     2280
cgtggaggtg gggagcgagg gcccctgaa aggcatccag atctggaagg tgccagccac    2340
cgacacctac agcatctcgg gctacgagc tgctggcggg aaaggcggga agaacaccat     2400
gatgcggtcc cacggcgtgt ctgtgctggg catcttcaac ctggagaagg atgacatgct    2460
gtacatcctg gttgggcagc agggagagga cgcctgcccc agtacaaacc agttaatcca     2520
```

```
gaaagtctgc attggagaga acaatgtgat agaagaagaa atccgtgtga acagaagcgt   2580
gcatgagtgg gcaggaggcg gaggaggagg gggtggagcc acctacgtat ttaagatgaa   2640
ggatggagtg ccggtgcccc tgatcattgc agccggaggt ggtggcaggg cctacggggc   2700
caagacagac acgttccacc cagagagact ggagaataac tcctcggttc tagggctaaa   2760
cggcaattcc ggagccgcag gtggtggagg tggctggaat gataacactt ccttgctctg   2820
ggccggaaaa tctttgcagg agggtgccac cggaggacat tcctgccccc aggccatgaa   2880
gaagtggggg tgggagacaa gagggggttt cggaggggt ggaggggggt gctcctcagg    2940
tggaggaggc ggaggatata taggcggcaa tgcagcctca acaatgacc ccgaaatgga    3000
tggggaagat ggggtttcct tcatcagtcc actgggcatc ctgtacaccc cagctttaaa   3060
agtgatggaa ggccacgggg aagtgaatat taagcattat ctaaactgca gtcactgtga   3120
ggtagacgaa tgtcacatgg accctgaaag ccacaaggtc atctgcttct gtgaccacgg   3180
gacggtgctg gctgaggatg gcgtctcctg cattgtgtca cccacccgg agccacacct    3240
gccactctcg ctgatcctct ctgtggtgac ctctgccctc gtggccgccc tggtcctggc   3300
tttctccggc atcatgattg tgtaccgccg gaagcaccag gagctgcaag ccatgcagat   3360
ggagctgcag agccctgagt acaagctgag caagctccgc acctcgacca tcatgaccga   3420
ctacaacccc aactactgct ttgctggcaa gacctcctcc atcagtgacc tgaaggaggt   3480
gccgcggaaa acatcacccc tcattcgggg tctgggccat ggcgcctttg gggaggtgta   3540
tgaaggccag gtgtccggaa tgcccaacga cccaagcccc ctgcaagtgg ctgtgaagac   3600
gctgcctgaa gtgtgctctg aacaggacga actggatttc ctcatggaag ccctgatcat   3660
cagcaaattc aaccaccaga acattgttcg ctgcattggg gtgagcctgc aatccctgcc   3720
ccggttcatc ctgctggagc tcatggcggg gggagacctc aagtccttcc tccgagagac   3780
ccgcccccgc ccgagccagc cctcctccct ggccatgctg gaccttctgc acgtggctcg   3840
ggacattgcc tgtggctgtc agtatttgga ggaaaaccac ttcatccacc gagacattgc   3900
tgccagaaac tgcctcttga cctgtccagg ccctggaaga gtggccaaga ttggagactt   3960
cgggatggcc cgagacatct acaggcgagc tactataga aagggaggct gtgccatgct    4020
gccagttaag tggatgcccc cagaggcctt catggaagga atattcactt ctaaaacaga   4080
cacatggtcc tttggagtgc tgctatggga aatcttttct cttggatata tgccataccc   4140
cagcaaaagc aaccaggaag ttctggagtt tgtcaccagt ggaggccgga tggacccacc   4200
caagaactgc cctgggcctg tataccggat aatgactcag tgctggcaac atcagcctga   4260
agacaggccc aactttgcca tcattttgga gaggattgaa tactgcaccc aggacccgga   4320
tgtaatcaac accgctttgc cgatagaata tggtccactt gtggaagagg aagagaaagt   4380
gcctgtgagg cccaaggacc ctgaggggt tcctcctctc ctggtctctc aacaggcaaa    4440
acgggaggag gagcgcagcc cagctgcccc accacctctg cctaccacct cctctggcaa   4500
ggctgcaaag aaacccacag ctgcagaggt ctctgttcga gtccctagag ggccggccgt   4560
ggaaggggga cacgtgaata tggcattctc tcagtccaac cctccttcgg agttgcacag   4620
ggtccacgga tccagaaata gcccaccag cttgtgaac ccaacgtacg gctcctggtt    4680
tacagagaaa cccaccaaaa agaataatcc tatagcaaag aaggagccac acgagagggg   4740
taacctgggg ctgagggaa gctgtactgt cccacctaac gttgcaactg ggagacttcc   4800
gggggcctca ctgctcctag agccctcttc gctgactgcc aatatgaagg aggtacctct   4860
```

```
gttcaggcta cgtcacttcc cttgtgggaa tgtcaattac ggctaccagc aacagggctt    4920
gcccttagaa gccgctactg cccctggagc tggtcattac gaggatacca ttctgaaaag    4980
caagaatagc atgaaccagc ctgggccctg agctcggtcg cacactcact tctcttcctt    5040
gggatcccta agaccgtgga ggagagagag gcaatcaatg gctcctttca caaaccagag    5100
accaaatgtc acgttttgtt ttgtgccaac ctattttgaa gtaccaccaa aaaagctgta    5160
ttttgaaaat gctttagaaa ggttttgagc atgggttcat cctattcttt cgaaagaaga    5220
aaatatcata aaaatgagtg ataaatacaa ggccagatgt ggttgcataa ggtttttatg    5280
catgtttgtt gta                                                       5293
```

<210> SEQ ID NO 7
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(87)

<400> SEQUENCE: 7

```
gca gac aag cat aaa gat gtc atc atc aac caa gca aaa atg tca act    48
Ala Asp Lys His Lys Asp Val Ile Ile Asn Gln Ala Lys Met Ser Thr
 1               5                  10                  15 cgc gaa aaa aac agc caa gtg tac cgc cgg aag cac cag                87
Arg Glu Lys Asn Ser Gln Val Tyr Arg Arg Lys His Gln
             20                  25
```

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ala Asp Lys His Lys Asp Val Ile Ile Asn Gln Ala Lys Met Ser Thr
 1               5                  10                  15

Arg Glu Lys Asn Ser Gln Val Tyr Arg Arg Lys His Gln
             20                  25
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gcagtagttg gggttgtagt c                                              21
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcggagcttg ctcagcttgt                                           20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgcagctcct ggtgcttcc                                            19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcagctcct ggtgcttcc                                            19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgcaagatgg acggtttggc                                           20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgttcaagat cgcctgtcag ctct                                      24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgaaatcact gtgctaaagg cggc                                      24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagccctcga gcagttattc ccat                                      24

-continued

```
<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaattccgcc gagctcaggg cccag                                              25

<210> SEQ ID NO 18
<211> LENGTH: 1059
<212> TYPE: PRT
<213> ORGANISM: Homo sapiens

<400> SEQUENCE: 18
```

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Leu Ala Asp Val
        35                  40                  45

Leu Arg Arg Leu Ala Ile Ser Glu Asp His Val Ala Ser Val Lys Lys
50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
    210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Val Leu Phe Asn Tyr Glu Glu Arg Thr Gln Arg His
    290                 295                 300

```
Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
            325                 330                 335

Arg Pro Leu Gln Pro His Val Arg Val Trp Asp Ser Val Thr Leu Ser
        340                 345                 350

Thr Leu Gln Ile Ile Gly Leu Gly Thr Phe Glu Arg Gly Val Gly Cys
    355                 360                 365

Leu Asp Phe Ser Lys Ala Asp Ser Gly Val His Leu Cys Ile Ile Asp
370                 375                 380

Asp Ser Asn Glu His Met Leu Thr Val Trp Asp Trp Gln Lys Lys Ala
385                 390                 395                 400

Lys Gly Ala Glu Ile Lys Thr Thr Asn Glu Val Val Leu Ala Val Glu
            405                 410                 415

Phe His Pro Thr Asp Ala Asn Thr Ile Ile Thr Cys Gly Lys Ser His
        420                 425                 430

Ile Phe Phe Trp Thr Trp Ser Gly Asn Ser Leu Thr Arg Lys Gln Gly
    435                 440                 445

Ile Phe Gly Lys Tyr Glu Lys Pro Lys Phe Val Gln Cys Leu Ala Phe
450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
            485                 490                 495

Val Tyr Arg Arg Lys His Gln Glu Leu Gln Ala Met Gln Met Glu Leu
        500                 505                 510

Gln Ser Pro Glu Tyr Lys Leu Ser Lys Leu Arg Thr Ser Thr Ile Met
    515                 520                 525

Thr Asp Tyr Asn Pro Asn Tyr Cys Phe Ala Gly Lys Thr Ser Ser Ile
530                 535                 540

Ser Asp Leu Lys Glu Val Pro Arg Lys Asn Ile Thr Leu Ile Arg Gly
545                 550                 555                 560

Leu Gly His Gly Ala Phe Gly Glu Val Tyr Glu Gly Gln Val Ser Gly
            565                 570                 575

Met Pro Asn Asp Pro Ser Pro Leu Gln Val Ala Val Lys Thr Leu Pro
        580                 585                 590

Glu Val Cys Ser Glu Gln Asp Glu Leu Asp Phe Leu Met Glu Ala Leu
    595                 600                 605

Ile Ile Ser Lys Phe Asn His Gln Asn Ile Val Arg Cys Ile Gly Val
610                 615                 620

Ser Leu Gln Ser Leu Pro Arg Phe Ile Leu Leu Glu Leu Met Ala Gly
625                 630                 635                 640

Gly Asp Leu Lys Ser Phe Leu Arg Glu Thr Arg Pro Arg Pro Ser Gln
            645                 650                 655

Pro Ser Ser Leu Ala Met Leu Asp Leu Leu His Val Ala Arg Asp Ile
        660                 665                 670

Ala Cys Gly Cys Gln Tyr Leu Glu Glu Asn His Phe Ile His Arg Asp
    675                 680                 685

Ile Ala Ala Arg Asn Cys Leu Leu Thr Cys Pro Gly Pro Gly Arg Val
690                 695                 700

Ala Lys Ile Gly Asp Phe Gly Met Ala Arg Asp Ile Tyr Arg Ala Ser
705                 710                 715                 720

Tyr Tyr Arg Lys Gly Gly Cys Ala Met Leu Pro Val Lys Trp Met Pro
```

```
                        725                 730                 735
Pro Glu Ala Phe Met Glu Gly Ile Phe Thr Ser Lys Thr Asp Thr Trp
                740                 745                 750
Ser Phe Gly Val Leu Leu Trp Glu Ile Phe Ser Leu Gly Tyr Met Pro
            755                 760                 765
Tyr Pro Ser Lys Ser Asn Gln Glu Val Leu Glu Phe Val Thr Ser Gly
        770                 775                 780
Gly Arg Met Asp Pro Pro Lys Asn Cys Pro Gly Pro Val Tyr Arg Ile
785                 790                 795                 800
Met Thr Gln Cys Trp Gln His Gln Pro Glu Asp Arg Pro Asn Phe Ala
                805                 810                 815
Ile Ile Leu Glu Arg Ile Glu Tyr Cys Thr Gln Asp Pro Asp Val Ile
                820                 825                 830
Asn Thr Ala Leu Pro Ile Glu Tyr Gly Pro Leu Val Glu Glu Glu Glu
                835                 840                 845
Lys Val Pro Val Arg Pro Lys Asp Pro Glu Gly Val Pro Pro Leu Leu
        850                 855                 860
Val Ser Gln Gln Ala Lys Arg Glu Glu Glu Arg Ser Pro Ala Ala Pro
865                 870                 875                 880
Pro Pro Leu Pro Thr Thr Ser Ser Gly Lys Ala Ala Lys Lys Pro Thr
                        885                 890                 895
Ala Ala Glu Ile Ser Val Arg Val Pro Arg Gly Pro Ala Val Glu Gly
                900                 905                 910
Gly His Val Asn Met Ala Phe Ser Gln Ser Asn Pro Pro Ser Glu Leu
            915                 920                 925
His Lys Val His Gly Ser Arg Asn Lys Pro Thr Ser Leu Trp Asn Pro
        930                 935                 940
Thr Tyr Gly Ser Trp Phe Thr Glu Lys Pro Thr Lys Lys Asn Asn Pro
945                 950                 955                 960
Ile Ala Lys Lys Glu Pro His Asp Arg Gly Asn Leu Gly Leu Glu Gly
                965                 970                 975
Ser Cys Thr Val Pro Pro Asn Val Ala Thr Gly Arg Leu Pro Gly Ala
                980                 985                 990
Ser Leu Leu Leu Glu Pro Ser Ser Leu Thr Ala Asn Met Lys Glu Val
            995                 1000                1005
Pro Leu Phe Arg Leu Arg His Phe Pro Cys Gly Asn Val Asn Tyr Gly
        1010                1015                1020
Tyr Gln Gln Gln Gly Leu Pro Leu Glu Ala Ala Thr Ala Pro Gly Ala
1025                1030                1035                1040
Gly His Tyr Glu Asp Thr Ile Leu Lys Ser Lys Asn Ser Met Asn Gln
                1045                1050                1055
Pro Gly Pro

<210> SEQ ID NO 19
<211> LENGTH: 3180
<212> TYPE: DNA
<213> ORGANISM: Homo sapiens

<400> SEQUENCE: 19
atggacggtt tcgccggcag tctcgatgat agtatttctg ctgcaagtac ttctgatgtt      60
caagatcgcc tgtcagctct tgagtcacga gttcagcaac aagaagatga aatcactgtg     120
ctaaaggcgg ctttggctga tgttttgagg cgtcttgcaa tctctgaaga tcatgtggcc     180
tcagtgaaaa aatcagtctc aagtaaaggc caaccaagcc ctcgagcagt tattcccatg     240
```

```
tcctgtataa ccaatggaag tggtgcaaac agaaaaccaa gtcataccag tgctgtctca    300
attgcaggaa aagaaactct ttcatctgct gctaaaagtg gtacagaaaa aagaaagaa    360
aaaccacaag gacagagaga aaaaaaagag gaatctcatt ctaatgatca aagtccacaa    420
attcgagcat caccttctcc ccagccctct tcacaacctc tccaaataca cagacaaact    480
ccagaaagca agaatgctac tcccaccaaa agcataaaac gaccatcacc agctgaaaag    540
tcacataatt cttgggaaaa ttcagatgat agccgtaata aattgtcgaa ataccttca     600
acacccaaat taataccaaa agttaccaaa actgcagaca agcataaaga tgtcatcatc    660
aaccaagaag gagaatatat taaaatgttt atgcgcggtc ggccaattac catgttcatt    720
ccttccgatg ttgacaacta tgatgacatc agaacggaac tgcctcctga agctcaaa     780
ctggagtggg catatggtta tcgaggaaag gactgtagag ctaatgttta ccttcttccg    840
accggggaaa tagtttattt cattgcatca gtagtagtac tatttaatta tgaggagaga    900
actcagcgac actacctggg ccatacagac tgtgtgaaat gccttgctat acatcctgac    960
aaaattagga ttgcaactgg acagatagct ggcgtggata agatggaag gcctctacaa    1020
ccccacgtca gagtgtggga ttctgttact ctatccacac tgcagattat tggacttggc    1080
acttttgagc gtggagtagg atgcctggat ttttcaaaag cagattcagg tgttcattta    1140
tgtattattg atgactccaa tgagcatatg cttactgtat gggactggca gaagaaagca    1200
aaaggagcag aaataaagac aacaaatgaa gttgttttgg ctgtggagtt tcacccaaca    1260
gatgcaaata ccataattac atgcggtaaa tctcatattt tcttctggac ctggagcggc    1320
aattcactaa caagaaaaca gggaattttt gggaaatatg aaaagccaaa atttgtgcag    1380
tgtttagcat tcttggggaa tggagatgtt cttactggag actcaggtgg agtcatgctt    1440
atatggagca aaactactgt agagcccaca cctgggaaag gacctaaagt gtaccgccgg    1500
aagcaccagg agctgcaagc catgcagatg gagctgcaga gccctgagta caagctgagc    1560
aagctccgca cctcgaccat catgaccgac tacaacccca actactgctt tgctggcaag    1620
acctcctcca tcagtgacct gaaggaggtg ccgcggaaaa acatcaccct cattcggggt    1680
ctgggccatg gcgcctttgg ggaggtgtat gaaggccagg tgtccggaat gcccaacgac    1740
ccaagccccc tgcaagtggc tgtgaagacg ctgcctgaag tgtgctctga acaggacgaa    1800
ctggatttcc tcatggaagc cctgatcatc agcaaattca accaccagaa cattgttcgc    1860
tgcattgggg tgagcctgca atccctgccc cggttcatcc tgctggagct catggcgggg    1920
ggagacctca gtcccttcct ccgagagacc cgccctcgcc cgagccagcc ctcctccctg    1980
gccatgctgg accttctgca cgtggctcgg gacattgcct gtggctgtca gtatttggag    2040
gaaaaccact tcatccaccg agacattgct gccagaaact gcctcttgac ctgtccaggc    2100
cctggaagag tggccaagat tggagacttc gggatggccc gagacatcta cagggcgagc    2160
tactatagaa agggaggctg tgccatgctg ccagttaagt ggatgccccc agaggccttc    2220
atggaaggaa tattcacttc taaaacagac acatggtcct ttggagtgct gctatgggaa    2280
atcttttctc ttggatatat gccataccccc agcaaaagca accaggaagt tctggagttt    2340
gtcaccagtg gaggccggat ggacccaccc aagaactgcc ctgggcctgt ataccggata    2400
atgactcagt gctggcaaca tcagcctgaa gacaggccca ctttgccat cattttggag    2460
aggattgaat actgcaccca ggacccggat gtaatcaaca ccgctttgcc gatagaatat    2520
ggtccacttg tggaagagga agagaaagtg cctgtgaggc ccaaggaccc tgagggggtt    2580
```

-continued

```
cctcctctcc tggtctctca acaggcaaaa cgggaggagg agcgcagccc agctgcccca   2640
ccacctctgc ctaccacctc ctctggcaag gctgcaaaga aacccacagc tgcagagatc   2700
tctgttcgag tccctagagg gccggccgtg aaggggggac acgtgaatat ggcattctct   2760
cagtccaacc ctccttcgga gttgcacaag gtccacggat ccagaaacaa gcccaccagc   2820
ttgtggaacc caacgtacgg ctcctggttt acagagaaac ccaccaaaaa gaataatcct   2880
atagcaaaga aggagccaca cgacaggggt aacctgggc tggagggaag ctgtactgtc    2940
ccacctaacg ttgcaactgg gagacttccg ggggcctcac tgctcctaga gccctcttcg   3000
ctgactgcca atatgaagga ggtacctctg ttcaggctac gtcacttccc ttgtgggaat   3060
gtcaattacg gctaccagca acagggcttg cccttagaag ccgctactgc ccctggagct   3120
ggtcattacg aggataccat tctgaaaagc aagaatagca tgaaccagcc tgggccctga   3180
```

<210> SEQ ID NO 20
<211> LENGTH: 701
<212> TYPE: PRT
<213> ORGANISM: Homo sapiens

<400> SEQUENCE: 20

```
Met Asn Gly Gln Leu Asp Leu Ser Gly Lys Leu Ile Ile Lys Ala Gln
 1               5                  10                  15

Leu Gly Glu Asp Ile Arg Arg Ile Pro Ile His Asn Glu Asp Ile Thr
             20                  25                  30

Tyr Asp Glu Leu Val Leu Met Met Gln Arg Val Phe Arg Gly Lys Leu
         35                  40                  45

Leu Ser Asn Asp Glu Val Thr Ile Lys Tyr Lys Asp Glu Asp Gly Asp
     50                  55                  60

Leu Ile Thr Ile Phe Asp Ser Ser Asp Leu Ser Phe Ala Ile Gln Cys
 65                  70                  75                  80

Ser Arg Ile Leu Lys Leu Thr Leu Phe Val Asn Gly Gln Pro Arg Pro
                 85                  90                  95

Leu Glu Ser Ser Gln Val Lys Tyr Leu Arg Arg Glu Leu Ile Glu Leu
            100                 105                 110

Arg Asn Lys Val Asn Arg Leu Leu Asp Ser Leu Glu Pro Pro Gly Glu
        115                 120                 125

Pro Gly Pro Ser Thr Asn Ile Pro Glu Asn Val Tyr Arg Arg Lys His
    130                 135                 140

Gln Glu Leu Gln Ala Met Gln Met Glu Leu Gln Ser Pro Glu Tyr Lys
145                 150                 155                 160

Leu Ser Lys Leu Arg Thr Ser Thr Ile Met Thr Asp Tyr Asn Pro Asn
                165                 170                 175

Tyr Cys Phe Ala Gly Lys Thr Ser Ser Ile Ser Asp Leu Lys Glu Val
            180                 185                 190

Pro Arg Lys Asn Ile Thr Leu Ile Arg Gly Leu Gly His Gly Ala Phe
        195                 200                 205

Gly Glu Val Tyr Glu Gly Gln Val Ser Gly Met Pro Asn Asp Pro Ser
    210                 215                 220

Pro Leu Gln Val Ala Val Lys Thr Leu Pro Glu Val Cys Ser Glu Gln
225                 230                 235                 240

Asp Glu Leu Asp Phe Leu Met Glu Ala Leu Ile Ile Ser Lys Phe Asn
                245                 250                 255

His Gln Asn Ile Val Arg Cys Ile Gly Val Ser Leu Gln Ser Leu Pro
            260                 265                 270
```

-continued

```
Arg Phe Ile Leu Leu Glu Leu Met Ala Gly Gly Asp Leu Lys Ser Phe
            275                 280                 285

Leu Arg Glu Thr Arg Pro Arg Pro Ser Gln Pro Ser Ser Leu Ala Met
290                 295                 300

Leu Asp Leu Leu His Val Ala Arg Asp Ile Ala Cys Gly Cys Gln Tyr
305                 310                 315                 320

Leu Glu Glu Asn His Phe Ile His Arg Asp Ile Ala Ala Arg Asn Cys
                325                 330                 335

Leu Leu Thr Cys Pro Gly Pro Gly Arg Val Ala Lys Ile Gly Asp Phe
                340                 345                 350

Gly Met Ala Arg Asp Ile Tyr Arg Ala Ser Tyr Tyr Arg Lys Gly Gly
            355                 360                 365

Cys Ala Met Leu Pro Val Lys Trp Met Pro Pro Glu Ala Phe Met Glu
370                 375                 380

Gly Ile Phe Thr Ser Lys Thr Asp Thr Trp Ser Phe Gly Val Leu Leu
385                 390                 395                 400

Trp Glu Ile Phe Ser Leu Gly Tyr Met Pro Tyr Pro Ser Lys Ser Asn
                405                 410                 415

Gln Glu Val Leu Glu Phe Val Thr Ser Gly Gly Arg Met Asp Pro Pro
                420                 425                 430

Lys Asn Cys Pro Gly Pro Val Tyr Arg Ile Met Thr Gln Cys Trp Gln
                435                 440                 445

His Gln Pro Glu Asp Arg Pro Asn Phe Ala Ile Ile Leu Glu Arg Ile
            450                 455                 460

Glu Tyr Cys Thr Gln Asp Pro Asp Val Ile Asn Thr Ala Leu Pro Ile
465                 470                 475                 480

Glu Tyr Gly Pro Leu Val Glu Glu Glu Lys Val Pro Val Arg Pro
                485                 490                 495

Lys Asp Pro Glu Gly Val Pro Leu Leu Val Ser Gln Gln Ala Lys
                500                 505                 510

Arg Glu Glu Glu Arg Ser Pro Ala Ala Pro Pro Pro Leu Pro Thr Thr
            515                 520                 525

Ser Ser Gly Lys Ala Ala Lys Lys Pro Thr Ala Ala Glu Ile Ser Val
530                 535                 540

Arg Val Pro Arg Gly Pro Ala Val Glu Gly Gly His Val Asn Met Ala
545                 550                 555                 560

Phe Ser Gln Ser Asn Pro Pro Ser Glu Leu His Lys Val His Gly Ser
                565                 570                 575

Arg Asn Lys Pro Thr Ser Leu Trp Asn Pro Thr Tyr Gly Ser Trp Phe
                580                 585                 590

Thr Glu Lys Pro Thr Lys Lys Asn Asn Pro Ile Ala Lys Lys Glu Pro
            595                 600                 605

His Asp Arg Gly Asn Leu Gly Leu Glu Gly Ser Cys Thr Val Pro Pro
610                 615                 620

Asn Val Ala Thr Gly Arg Leu Pro Gly Ala Ser Leu Leu Leu Glu Pro
625                 630                 635                 640

Ser Ser Leu Thr Ala Asn Met Lys Glu Val Pro Leu Phe Arg Leu Arg
                645                 650                 655

His Phe Pro Cys Gly Asn Val Asn Tyr Gly Tyr Gln Gln Gln Gly Leu
                660                 665                 670

Pro Leu Glu Ala Ala Thr Ala Pro Gly Ala Gly His Tyr Glu Asp Thr
            675                 680                 685

Ile Leu Lys Ser Lys Asn Ser Met Asn Gln Pro Gly Pro
```

<210> SEQ ID NO 21
<211> LENGTH: 2106
<212> TYPE: DNA
<213> ORGANISM: Homo sapiens

<400> SEQUENCE: 21

```
atgaacggac agttggatct aagtgggaag ctaatcatca aagctcaact tggggaggat      60
attcggcgaa ttcctattca taatgaagat attacttatg atgaattagt gctaatgatg     120
caacgagttt tcagaggaaa acttctgagt aatgatgaag taacaataaa gtataaagat     180
gaagatggag atcttataac aattttttgat agttctgacc tttcctttgc aattcagtgc     240
agtaggatac tgaaactgac attatttgtt aatggccagc caagacccct gaatcaagt     300
caggtgaaat atctccgtcg agaactgata gaacttcgaa ataaagtgaa tcgtttattg     360
gatagcttgg aaccacctgg agaaccagga ccttccacca atattcctga aaatgtgtac     420
cgccggaagc caggagct gcaagccatg cagatgagc tgcagagccc tgagtacaag     480
ctgagcaagc tccgcacctc gaccatcatg accgactaca accccaacta ctgctttgct     540
ggcaagacct cctccatcag tgacctgaag gaggtgccgc ggaaaaacat caccctcatt     600
cggggtctgg ccatggcgc ctttggggag gtgtatgaag ccaggtgtc cggaatgccc     660
aacgacccaa gcccctgca gtggctgtg aagacgctgc tgaagtgtg ctctgaacag     720
gacgaactgg atttcctcat ggaagccctg atcatcagca aattcaacca ccagaacatt     780
gttcgctgca ttggggtgag cctgcaatcc ctgccccgt tcatcctgct ggagctcatg     840
gcggggggag acctcaagtc cttcctccga gagaccccgcc ctcgcccgag ccagccctcc     900
tccctggcca tgctggacct tctgcacgtg gctcgggaca ttgcctgtgg ctgtcagtat     960
ttggaggaaa accacttcat ccaccgagac attgctgcca gaaactgcct cttgacctgt    1020
ccaggccctg gaagagtggc caagattgga gacttcggga tggcccgaga catctacagg    1080
gcgagctact atagaaaggg gaggctgtgcc atgctgccag ttaagtggat gccccagag    1140
gccttcatgg aaggaatatt cacttctaaa acagacacat ggtcctttgg agtgctgcta    1200
tgggaaatct tttctcttgg atatatgcca taccccagca aaagcaacca ggaagttctg    1260
gagtttgtca ccagtggagg ccggatggac ccacccaaga actgccctgg cctgtatac    1320
cggataatga ctcagtgctg gcaacatcag cctgaagaca ggcccaactt tgccatcatt    1380
ttggagagga ttgaatactg cacccaggac ccggatgtaa tcaacaccgc tttgccgata    1440
gaatatggtc cacttgtgga agaggaagag aaagtgcctg tgaggcccaa ggaccctgag    1500
gggttcctc ctctcctggt ctctcaacag gcaaaacggg aggaggagcg cagcccagct    1560
gccccaccac ctctgcctac cacctcctct ggcaaggctg caaagaaacc cacagctgca    1620
gagatctctg ttcgagtccc tagagggccg gccgtggaag ggggacacgt gaatatggca    1680
ttctctcagt ccaacccctcc ttcggagttg cacaaggtcc acggatccag aaacaagccc    1740
accagcttgt ggaacccaac gtacggctcc tggtttacag agaaacccac caaaaagaat    1800
aatcctatag caaagaagga gccacacgac agggtaacc tggggctgga gggaagctgt    1860
actgtcccac ctaacgttgc aactgggaga cttccgggg cctcactgct cctagagccc    1920
tcttcgctga ctgccaatat gaaggaggta cctctgttca ggctacgtca cttcccttgt    1980
gggaatgtca attcggcta ccagcaacag ggcttgccct tagaagccgc tactgcccct    2040
ggagctggtc attacgagga taccattctg aaaagcaaga atagcatgaa ccagcctggg    2100
``` ccctga                                                                  2106

<210> SEQ ID NO 22
<211> LENGTH: 400
<212> TYPE: PRT
<213> ORGANISM: Homo sapiens

<400> SEQUENCE: 22

Met Asn Gly Gln Leu Asp Leu Ser Gly Lys Leu Ile Val Lys Ala Gln
1               5                   10                  15

Leu Gly Glu Asp Ile Arg Arg Ile Pro Ile His Asn Glu Asp Ile Thr
            20                  25                  30

Tyr Asp Glu Leu Val Leu Met Met Gln Arg Val Phe Arg Gly Lys Leu
        35                  40                  45

Leu Ser Asn Asp Glu Val Thr Ile Lys Tyr Lys Asp Glu Asp Gly Asp
    50                  55                  60

Leu Ile Thr Ile Phe Asp Ser Ser Asp Leu Ser Phe Ala Ile Gln Cys
65                  70                  75                  80

Ser Arg Ile Leu Lys Leu Thr Leu Phe Val Asn Gly Gln Pro Arg Pro
                85                  90                  95

Leu Glu Ser Ser Gln Val Lys Tyr Leu Arg Arg Glu Leu Ile Glu Leu
            100                 105                 110

Arg Asn Lys Val Asn Arg Leu Leu Asp Ser Leu Glu Pro Pro Gly Glu
        115                 120                 125

Pro Gly Pro Ser Thr Asn Ile Pro Glu Asn Asp Thr Val Asp Gly Arg
    130                 135                 140

Glu Glu Lys Ser Ala Ser Asp Ser Ser Gly Lys Gln Ser Thr Gln Val
145                 150                 155                 160

Met Ala Ala Ser Met Ser Ala Phe Asp Pro Leu Lys Asn Gln Asp Glu
                165                 170                 175

Ile Asn Lys Asn Val Met Ser Ala Phe Gly Leu Thr Asp Asp Gln Val
            180                 185                 190

Ser Gly Pro Pro Ser Ala Pro Ala Glu Asp Arg Ser Gly Thr Pro Asp
        195                 200                 205

Ser Ile Ala Ser Ser Ser Ser Ala Ala His Pro Pro Gly Val Gln Pro
    210                 215                 220

Gln Gln Pro Pro Tyr Thr Gly Ala Gln Thr Gln Ala Gly Gln Ile Glu
225                 230                 235                 240

Gly Gln Met Tyr Gln Gln Tyr Gln Gln Gln Ala Gly Tyr Gly Ala Gln
                245                 250                 255

Gln Pro Gln Ala Pro Pro Gln Gln Pro Gln Gln Tyr Gly Ile Gln Tyr
            260                 265                 270

Ser Ala Ser Tyr Ser Gln Gln Thr Gly Pro Gln Gln Pro Gln Gln Phe
        275                 280                 285

Gln Gly Tyr Gly Gln Gln Pro Thr Ser Gln Ala Pro Ala Pro Ala Phe
    290                 295                 300

Ser Gly Gln Pro Gln Gln Leu Pro Ala Gln Pro Gln Gln Tyr Gln
305                 310                 315                 320

Ala Ser Asn Tyr Pro Ala Gln Thr Tyr Thr Ala Gln Thr Ser Gln Pro
                325                 330                 335

Thr Asn Tyr Thr Val Ala Pro Ala Ser Gln Pro Gly Met Ala Pro Ser
            340                 345                 350

Gln Pro Gly Ala Tyr Gln Pro Arg Pro Gly Phe Thr Ser Leu Pro Gly
        355                 360                 365

```
Ser Thr Met Thr Pro Pro Ser Gly Pro Asn Pro Tyr Ala Arg Asn
    370                 375                 380

Arg Pro Pro Phe Gly Gln Gly Tyr Thr Gln Pro Gly Pro Gly Tyr Arg
385                 390                 395                 400
```

<210> SEQ ID NO 23
<211> LENGTH: 1648
<212> TYPE: DNA
<213> ORGANISM: Homo sapiens

<400> SEQUENCE: 23

```
atgaacggac agttggatct aagtgggaag ctaatcatca aagctcaact tggggaggat      60
attcggcgaa ttcctattca taatgaagat attacttatg atgaattagt gctaatgatg     120
caacgagttt tcagaggaaa acttctgagt aatgatgaag taacaataaa gtataaagat     180
gaagatggag atcttataac aatttttgat agttctgacc tttcctttgc aattcagtgc     240
agtaggatac tgaaactgac attatttgtt aatggccagc caagacccct tgaatcaagt     300
caggtgaaat atctccgtcg agaactgata gaacttcgaa ataaagtgaa tcgtttattg     360
gatagcttgg aaccacctgg agaaccagga ccttccacca atattcctga aaatgatact     420
gtggatggta gggaagaaaa gtctgcttct gattcttctg aaaacagtc tactcaggtt     480
atggcagcaa gtatgtctgc ttttgatcct ttaaaaaacc aagatgaaat caataaaaat     540
gttatgtcag cgtttggctt aacagatgat caggtttcag ggccacccag tgctcctgca     600
gaagatcgtt caggaacacc cgacagcatt gcttcctcct cctcagcagc tcacccacca     660
ggcgttcagc cacagcagcc accatataca ggagctcaga ctcaagcagg tcagattgaa     720
ggtcagatgt accaacagta ccagcaacag gccggctatg tgcacagca gccgcaggct     780
ccacctcagc agcctcaaca gtatggtatt cagtattcag caagctatag tcagcagact     840
ggacctcaac aacctcagca gttccaggga tatggccagc aaccaacttc ccaggcacca     900
gctcctgcct tttctggtca gcctcaacaa ctgcctgctc agccgccaca gcagtaccag     960
gcgagcaatt atcctgcaca aacttacact gcccaaactt ctcagcctac taattatact    1020
gtggctcctg cctctcaacc tggaatggct ccaagccaac tggggccta tcaaccaaga    1080
ccaggttttta cttcacttcc tggaagtacc atgacccctc ctccaagtgg gcctaatcct    1140
tatgcgcgta accgtcctcc ctttggtcag ggctataccc aacctggacc tggttatcga    1200
taaggaggct cctctacacc aattaatgta gctgctagct attggcctcc caaaagactc    1260
cagtactatt ttaatttgta ttgaagaagt tcagaaattt aaaagcagag cattttttat    1320
gatatcattg ttggtgttaa ttgaaagtat aatttgctgg aacacaaaga ccaaaatgaa    1380
agttttttcc tccctgctta aaaatgtagc agcttcttag ttactttgga acactactct    1440
tacatgtata aagtgattga cttgactttc tagcttccct tgtccggagg atattaaaat    1500
gctagggtga ggtttagcca tcttacttgg cttttactat taacatgatg tactaaagta    1560
gagccctttg agaatacaag atattatgta taaaatgtaa cactgatgat aggttaataa    1620
agatgattga atccattaaa aaaaaaa                                        1648
```

<210> SEQ ID NO 24

<400> SEQUENCE: 24

000

-continued

```
<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Trp Ser Lys Thr Thr Val Glu Pro Thr Pro Gly Lys Gly Pro Lys
1               5                   10                  15

Val Tyr Arg Arg Lys His Gln Glu Leu Gln Ala Met Gln Met Glu Leu
            20                  25                  30

Gln Ser Pro Glu Tyr Lys Leu
        35

<210> SEQ ID NO 26

<400> SEQUENCE: 26

000

<210> SEQ ID NO 27
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ser Leu Glu Pro Pro Gly Glu Pro Gly Pro Ser Thr Asn Ile Pro
1               5                   10                  15

Glu Asn Val Tyr Arg Arg Lys His Gln Glu Leu Gln Ala Met Gln Met
            20                  25                  30

Glu Leu Gln Ser Pro Glu Tyr Lys Leu
        35                  40

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tttgttaatg gccagccaag accc                                      24

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tttttttttt tttttttttt                                           20

<210> SEQ ID NO 30
<211> LENGTH: 7
<212> TYPE: PRT
<213> ORGANISM: Artificial Sequence
<220> FEATURE:
<223> OTHER INFORMATION: Synthetic Peptide
```

```
<400> SEQUENCE: 30

Val Tyr Arg Arg Lys His Gln
 1               5
```